US012685851B2

(12) United States Patent
    Abrams et al.

(10) Patent No.: US 12,685,851 B2
(45) Date of Patent: Jul. 21, 2026

(54) FLUID CATHETER DEVICE FOR RECORDING BRAIN STATE

(71) Applicant: Biogen MA Inc., Cambridge, MA (US)

(72) Inventors: Daniel J. Abrams, Denver, CO (US); Matias Maturana, Melbourne (AU)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 17/380,415

(22) Filed: Jul. 20, 2021

(65) Prior Publication Data

US 2022/0016404 A1    Jan. 20, 2022

Related U.S. Application Data

(60) Provisional application No. 63/053,864, filed on Jul. 20, 2020.

(51) Int. Cl.
    *A61M 27/00*    (2006.01)
    *A61B 5/00*    (2006.01)
    (Continued)

(52) U.S. Cl.
    CPC ........... *A61M 27/006* (2013.01); *A61B 5/293* (2021.01); *A61B 5/6852* (2013.01);
    (Continued)

(58) Field of Classification Search
    CPC ............ A61M 27/006; A61M 25/0026; A61M 39/0247; A61M 2039/0273;
    (Continued)

(56) References Cited

U.S. PATENT DOCUMENTS

| | | | |
|---|---|---|---|
| 1,456,469 A | 5/1923 | Schwidetzky |
| 2,609,818 A | 9/1952 | Parrine |
| | (Continued) | | |

FOREIGN PATENT DOCUMENTS

| | | | |
|---|---|---|---|
| CA | 3098311 A1 | 11/2019 |
| DE | 3127882 A1 | 2/1983 |
| | (Continued) | |

OTHER PUBLICATIONS

Abrams et al., "Implantable Cranial Medical Device," Cerebral Therapeutics, Inc., U.S. Appl. No. 63/052,284, filed Jul. 15, 2020, 77 pages.

(Continued)

*Primary Examiner* — Adam Marcetich
(74) *Attorney, Agent, or Firm* — Finnegan, Henderson, Farabow, Garrett & Dunner LLP

(57) ABSTRACT

A device or system for delivering fluid to or removing fluid from a CSF-containing space of a brain and for recording electrical activity from white or grey matter in the brain includes a catheter including a proximal end, a distal end portion, a first lumen extending from the proximal end to the distal end portion, and one or more electrodes positioned relative to the catheter a distance from a distal end of the catheter, such that the one or more electrodes would be placed in contact with white or grey matter of the brain if the distal end of the catheter were positioned in the CSF-containing space. The catheter may include the electrodes or a lead adjacent the catheter may include the electrodes.

33 Claims, 18 Drawing Sheets

(51) Int. Cl.
    *A61B 5/293*        (2021.01)
    *A61M 25/00*      (2006.01)
    *A61M 39/02*      (2006.01)

(52) U.S. Cl.
    CPC .......... *A61B 5/6864* (2013.01); *A61B 5/6868*
        (2013.01); *A61M 25/0026* (2013.01); *A61M*
        *39/0247* (2013.01); *A61M 2039/0273*
        (2013.01); *A61M 2039/0276* (2013.01)

(58) Field of Classification Search
    CPC .. A61M 2039/0276; A61M 2202/0464; A61M
        2210/0687; A61B 5/293; A61B 5/6852;
        A61B 5/6864; A61B 5/6868; A61B
        5/0538; A61B 5/0031; A61B 5/0006;
        A61B 5/291; A61B 5/369; A61N 1/0529;
        A61N 1/0531; A61N 1/0534; A61N
        1/0536; A61N 1/0539
    See application file for complete search history.

(56)          References Cited

U.S. PATENT DOCUMENTS

| | | | |
|---|---|---|---|
| 3,040,743 A | 6/1962 | Knut | |
| 3,506,006 A | 4/1970 | Lange, Jr. | |
| 3,563,373 A | 2/1971 | Paulson | |
| 3,640,269 A | 2/1972 | Delgado | |
| 3,888,249 A | 6/1975 | Spencer | |
| 3,892,237 A | 7/1975 | Steiner | |
| 4,281,666 A * | 8/1981 | Cosman | A61B 5/0002 |
| | | | 600/561 |
| 4,281,667 A * | 8/1981 | Cosman | A61B 5/0031 |
| | | | 600/561 |
| 4,464,168 A | 8/1984 | Redmond et al. | |
| 4,500,311 A | 2/1985 | Redmond et al. | |
| 4,583,968 A | 4/1986 | Mahurkar | |
| 4,677,985 A | 7/1987 | Bro et al. | |
| 4,723,556 A | 2/1988 | Sussman | |
| 4,732,850 A | 3/1988 | Brown et al. | |
| 4,767,410 A | 8/1988 | Moden et al. | |
| 4,779,763 A | 10/1988 | Klawitter | |
| 4,861,335 A | 8/1989 | Reynolds | |
| 4,883,101 A | 11/1989 | Strong | |
| 4,904,241 A | 2/1990 | Bark | |
| 4,946,778 A | 8/1990 | Ladner et al. | |
| 4,958,622 A | 9/1990 | Selenke | |
| 5,067,948 A | 11/1991 | Haber et al. | |
| 5,197,951 A | 3/1993 | Mahurkar | |
| 5,225,539 A | 7/1993 | Winter | |
| 5,334,163 A | 8/1994 | Sinnett | |
| 5,377,864 A | 1/1995 | Blechl et al. | |
| 5,522,807 A | 6/1996 | Luther | |
| 5,648,237 A | 7/1997 | Carter | |
| 5,704,352 A * | 1/1998 | Tremblay | A61B 5/01 |
| | | | 600/300 |
| 5,720,720 A | 2/1998 | Laske et al. | |
| 5,736,137 A | 4/1998 | Anderson et al. | |
| 5,810,789 A | 9/1998 | Powers et al. | |
| 5,823,961 A | 10/1998 | Fields et al. | |
| 5,897,528 A | 4/1999 | Schultz | |
| 5,902,331 A * | 5/1999 | Bonner | A61N 1/056 |
| | | | 600/585 |
| 6,001,806 A | 12/1999 | Hilbert et al. | |
| 6,006,124 A | 12/1999 | Fischell et al. | |
| 6,013,051 A | 1/2000 | Nelson | |
| 6,018,036 A | 1/2000 | Mosmann et al. | |
| 6,086,555 A * | 7/2000 | Eliasen | A61M 39/0208 |
| | | | 604/93.01 |
| 6,113,578 A | 9/2000 | Brown | |
| 6,248,080 B1 * | 6/2001 | Miesel | A61B 5/0215 |
| | | | 600/311 |
| 6,248,126 B1 * | 6/2001 | Lesser | A61F 7/12 |
| | | | 607/113 |
| 6,293,922 B1 | 9/2001 | Haase | |

| | | | |
|---|---|---|---|
| 6,324,433 B1 | 11/2001 | Errico | |
| 6,451,977 B1 | 9/2002 | de Sauvage et al. | |
| 6,458,943 B1 | 10/2002 | Byrne | |
| 6,475,987 B1 | 11/2002 | Shu | |
| 6,482,185 B1 | 11/2002 | Hartmann | |
| 6,562,023 B1 * | 5/2003 | Marrs | A61M 39/0208 |
| | | | 604/536 |
| 6,573,099 B2 | 6/2003 | Graham | |
| 6,595,979 B1 | 7/2003 | Epstein et al. | |
| 6,632,927 B2 | 10/2003 | Adair et al. | |
| 6,720,138 B2 | 4/2004 | Sharma et al. | |
| 6,753,139 B1 | 6/2004 | Baulcombe et al. | |
| 7,056,704 B2 | 6/2006 | Tuschl et al. | |
| 7,083,785 B2 | 8/2006 | Browning et al. | |
| 7,112,421 B2 | 9/2006 | Ambrose et al. | |
| 7,161,488 B2 | 1/2007 | Frasch | |
| 7,195,616 B2 | 3/2007 | Diller et al. | |
| 7,359,765 B2 | 4/2008 | Varvarelis et al. | |
| 7,371,388 B1 | 5/2008 | Ruben et al. | |
| 7,618,409 B2 | 11/2009 | Hochman | |
| 7,670,327 B2 | 3/2010 | Kucharczyk et al. | |
| 7,883,502 B2 | 2/2011 | Powers et al. | |
| 7,917,222 B1 * | 3/2011 | Osorio | A61N 1/0539 |
| | | | 607/45 |
| 7,922,695 B2 | 4/2011 | Wiegel et al. | |
| 8,066,681 B1 | 11/2011 | Hall et al. | |
| 8,277,425 B2 | 10/2012 | Girard et al. | |
| 8,409,133 B2 | 4/2013 | Pesach et al. | |
| 8,543,222 B1 * | 9/2013 | Sochor | A61B 90/11 |
| | | | 607/116 |
| 8,556,866 B2 | 10/2013 | Krulevitch et al. | |
| 8,744,544 B2 | 6/2014 | Najafi et al. | |
| 8,808,234 B2 | 8/2014 | Vogelbaum et al. | |
| 8,827,964 B2 | 9/2014 | Boyd et al. | |
| 8,979,822 B2 | 3/2015 | Vogelbaum et al. | |
| 9,913,960 B2 | 3/2018 | Blanchard et al. | |
| 10,506,988 B2 | 12/2019 | Karoly et al. | |
| 10,716,921 B2 | 7/2020 | Purdy | |
| 10,967,172 B1 | 4/2021 | Shire et al. | |
| 11,504,516 B2 | 11/2022 | Otto | |
| 11,534,592 B2 | 12/2022 | Singh et al. | |
| 12,097,029 B1 | 9/2024 | Shanechi | |
| 2002/0004643 A1 | 1/2002 | Carmel et al. | |
| 2002/0052563 A1 * | 5/2002 | Penn | A61M 27/006 |
| | | | 600/561 |
| 2002/0086356 A1 | 7/2002 | Tuschl et al. | |
| 2003/0012783 A1 | 1/2003 | Kindsvogel | |
| 2003/0069623 A1 * | 4/2003 | Stypulkowski | A61N 1/0551 |
| | | | 607/117 |
| 2003/0097051 A1 * | 5/2003 | Kolberg | A61N 1/056 |
| | | | 600/381 |
| 2003/0097082 A1 * | 5/2003 | Purdy | A61M 25/0662 |
| | | | 604/93.01 |
| 2003/0108923 A1 | 6/2003 | Tuschl et al. | |
| 2003/0135148 A1 | 7/2003 | Dextradeur et al. | |
| 2003/0204075 A9 | 10/2003 | Wang | |
| 2003/0216714 A1 | 11/2003 | Gill | |
| 2003/0228691 A1 | 12/2003 | Lewis et al. | |
| 2004/0002677 A1 | 1/2004 | Gentsler | |
| 2004/0053411 A1 | 3/2004 | Cullen et al. | |
| 2004/0069044 A1 | 4/2004 | Lavi et al. | |
| 2004/0073196 A1 | 4/2004 | Adams et al. | |
| 2004/0082984 A1 * | 4/2004 | Osorio | A61B 5/4094 |
| | | | 607/116 |
| 2004/0086884 A1 | 5/2004 | Beach et al. | |
| 2004/0102412 A1 | 5/2004 | Broschat et al. | |
| 2004/0106566 A1 | 6/2004 | Lin et al. | |
| 2004/0112411 A1 | 6/2004 | Boykin et al. | |
| 2004/0152112 A1 | 8/2004 | Croce et al. | |
| 2004/0171037 A1 | 9/2004 | Li et al. | |
| 2004/0171983 A1 | 9/2004 | Sparks et al. | |
| 2004/0175732 A1 | 9/2004 | Rana | |
| 2004/0210951 A1 | 10/2004 | Baulcombe et al. | |
| 2004/0215162 A1 | 10/2004 | Putz | |
| 2004/0221337 A1 | 11/2004 | Baulcombe et al. | |
| 2004/0229266 A1 | 11/2004 | Tuschl et al. | |
| 2004/0253604 A1 | 12/2004 | Lin et al. | |
| 2004/0259247 A1 | 12/2004 | Tuschl et al. | |

(56) References Cited

U.S. PATENT DOCUMENTS

| | | |
|---|---|---|
| 2004/0259248 A1 | 12/2004 | Tuschl et al. |
| 2004/0268441 A1 | 12/2004 | Vance et al. |
| 2005/0004219 A1 | 1/2005 | Hildebrand et al. |
| 2005/0004639 A1* | 1/2005 | Erickson ............. A61N 1/0551 |
| | | 607/122 |
| 2005/0026278 A1 | 2/2005 | Tuschl et al. |
| 2005/0037988 A1 | 2/2005 | Zamore et al. |
| 2005/0038371 A1 | 2/2005 | Reich et al. |
| 2005/0059005 A1 | 3/2005 | Tuschl et al. |
| 2005/0059011 A1 | 3/2005 | Sin et al. |
| 2005/0070458 A1 | 3/2005 | John |
| 2005/0074788 A1 | 4/2005 | Dahlberg et al. |
| 2005/0075492 A1 | 4/2005 | Chen et al. |
| 2005/0079614 A1 | 4/2005 | Reinhart et al. |
| 2005/0137578 A1 | 6/2005 | Heruth et al. |
| 2005/0159697 A1* | 7/2005 | Dextradeur ......... A61M 27/006 |
| | | 604/8 |
| 2005/0163775 A1 | 7/2005 | Chan et al. |
| 2005/0209332 A1 | 9/2005 | Kuppuswamy et al. |
| 2005/0228315 A1* | 10/2005 | Ayad ...................... A61B 5/293 |
| | | 600/587 |
| 2005/0245906 A1 | 11/2005 | Makower et al. |
| 2006/0004317 A1* | 1/2006 | Mauge ................ A61M 27/006 |
| | | 604/8 |
| 2006/0067933 A1 | 3/2006 | Gross et al. |
| 2006/0073146 A1 | 4/2006 | Ashkenazi et al. |
| 2006/0079834 A1 | 4/2006 | Tennican et al. |
| 2006/0084055 A1 | 4/2006 | Gaiger et al. |
| 2006/0084929 A1 | 4/2006 | Eliasen |
| 2006/0122677 A1* | 6/2006 | Vardiman ............ A61N 1/0534 |
| | | 607/116 |
| 2006/0160889 A1 | 7/2006 | Veeneman et al. |
| 2006/0286093 A1 | 12/2006 | Gross et al. |
| 2007/0073228 A1 | 3/2007 | Mernoe et al. |
| 2007/0078438 A1 | 4/2007 | Okada |
| 2007/0083063 A1 | 4/2007 | Nelson et al. |
| 2007/0086979 A1 | 4/2007 | Chevrier et al. |
| 2007/0123758 A1 | 5/2007 | Miesel et al. |
| 2007/0185017 A1 | 8/2007 | Aggarwal et al. |
| 2007/0197957 A1 | 8/2007 | Hunter et al. |
| 2007/0255237 A1 | 11/2007 | Lobl et al. |
| 2007/0260375 A1 | 11/2007 | Hilton |
| 2008/0027346 A1 | 1/2008 | Litt et al. |
| 2008/0039774 A1 | 2/2008 | Zawacki et al. |
| 2008/0058476 A1 | 3/2008 | Whiteker et al. |
| 2008/0132980 A1* | 6/2008 | Gerber ................ A61N 1/0534 |
| | | 607/116 |
| 2008/0132981 A1* | 6/2008 | Gerber ................ A61N 1/0534 |
| | | 607/116 |
| 2008/0147006 A1 | 6/2008 | Brunnberg et al. |
| 2008/0262374 A1 | 10/2008 | Gerber et al. |
| 2009/0030480 A1 | 1/2009 | Durand et al. |
| 2009/0069267 A1 | 3/2009 | Abrams et al. |
| 2009/0069742 A1 | 3/2009 | Larsen |
| 2009/0112327 A1 | 4/2009 | Lane et al. |
| 2009/0131850 A1 | 5/2009 | Geiger |
| 2009/0131857 A1 | 5/2009 | Geiger |
| 2009/0137944 A1 | 5/2009 | Haarala et al. |
| 2009/0203983 A1 | 8/2009 | Carlton et al. |
| 2009/0228066 A1 | 9/2009 | Hirata et al. |
| 2010/0036477 A1* | 2/2010 | Bronson ................ A61F 2/954 |
| | | 623/1.11 |
| 2010/0089167 A1 | 4/2010 | Trieu et al. |
| 2010/0145162 A1* | 6/2010 | Devauchelle .......... A61N 1/375 |
| | | 600/300 |
| 2010/0145176 A1 | 6/2010 | Himes |
| 2010/0158869 A1 | 6/2010 | Kaemmerer |
| 2010/0168532 A1 | 7/2010 | Waziri et al. |
| 2010/0210958 A1* | 8/2010 | Manwaring .......... A61B 5/4076 |
| | | 600/561 |
| 2010/0241088 A1 | 9/2010 | Ranalletta et al. |
| 2010/0280335 A1 | 11/2010 | Carlson et al. |
| 2010/0286585 A1* | 11/2010 | DiMauro ................ A61P 25/00 |
| | | 604/8 |
| 2010/0305492 A1 | 12/2010 | Lad et al. |
| 2011/0009821 A1 | 1/2011 | Jespersen et al. |
| 2011/0009933 A1* | 1/2011 | Barker ................ A61N 1/0551 |
| | | 607/116 |
| 2011/0033463 A1 | 2/2011 | Thakker et al. |
| 2011/0066072 A1 | 3/2011 | Kawoos et al. |
| 2011/0092921 A1 | 4/2011 | Beling et al. |
| 2011/0172633 A1 | 7/2011 | Ali et al. |
| 2011/0201944 A1 | 8/2011 | Higgins et al. |
| 2011/0257596 A1 | 10/2011 | Gaudet |
| 2011/0264033 A1 | 10/2011 | Jensen et al. |
| 2011/0270095 A1* | 11/2011 | Bukhman .............. A61B 5/349 |
| | | 607/45 |
| 2011/0270230 A1 | 11/2011 | Sage et al. |
| 2011/0275930 A1 | 11/2011 | Jho et al. |
| 2012/0015336 A1 | 1/2012 | Mach |
| 2012/0087869 A1 | 4/2012 | Thakker et al. |
| 2012/0245529 A1 | 9/2012 | Hummen et al. |
| 2012/0290225 A1 | 11/2012 | Julian et al. |
| 2012/0296271 A1* | 11/2012 | Yomtov ................ G16H 20/17 |
| | | 604/93.01 |
| 2012/0296404 A1* | 11/2012 | Carpentier ............. A61B 5/293 |
| | | 607/116 |
| 2012/0302959 A1* | 11/2012 | Fielder .............. A61M 5/14276 |
| | | 604/151 |
| 2012/0310140 A1 | 12/2012 | Kramer et al. |
| 2013/0204229 A1 | 8/2013 | Olson et al. |
| 2013/0253266 A1 | 9/2013 | Dextradeur et al. |
| 2013/0267928 A1 | 10/2013 | Imran et al. |
| 2013/0324945 A1* | 12/2013 | Sabin ................ A61M 39/0247 |
| | | 604/257 |
| 2014/0012209 A1 | 1/2014 | Sansoucy |
| 2014/0074060 A1 | 3/2014 | Imran |
| 2014/0081347 A1 | 3/2014 | Nelson et al. |
| 2014/0148780 A1* | 5/2014 | Putz ...................... A61B 5/293 |
| | | 604/524 |
| 2014/0194825 A1 | 7/2014 | Nielsen et al. |
| 2014/0207074 A1 | 7/2014 | Nielsen |
| 2014/0236259 A1* | 8/2014 | Colantonio .......... A61N 1/0551 |
| | | 607/46 |
| 2014/0249410 A1 | 9/2014 | Uber, III et al. |
| 2014/0257168 A1 | 9/2014 | Gill |
| 2014/0276416 A1* | 9/2014 | Nelson .............. A61M 39/0247 |
| | | 604/174 |
| 2014/0276473 A1 | 9/2014 | Beling et al. |
| 2015/0038901 A1 | 2/2015 | Lampropoulos et al. |
| 2015/0202373 A1 | 7/2015 | Creaturo |
| 2015/0209505 A1 | 7/2015 | Hanson et al. |
| 2015/0230724 A1 | 8/2015 | Waziri et al. |
| 2015/0238685 A1 | 8/2015 | Elias et al. |
| 2015/0297874 A1 | 10/2015 | East et al. |
| 2015/0306302 A1 | 10/2015 | Marsden et al. |
| 2015/0367067 A1 | 12/2015 | Minaie et al. |
| 2016/0122282 A1 | 5/2016 | Kandula |
| 2016/0213312 A1 | 7/2016 | Singh et al. |
| 2016/0374901 A9 | 12/2016 | Rodriguez et al. |
| 2017/0007621 A1 | 1/2017 | Wotton et al. |
| 2017/0173267 A1 | 6/2017 | Ashmead et al. |
| 2017/0325685 A1 | 11/2017 | Shachar et al. |
| 2017/0365101 A1 | 12/2017 | Samec et al. |
| 2018/0028746 A1 | 2/2018 | Abrams et al. |
| 2018/0028824 A1 | 2/2018 | Pivonka et al. |
| 2018/0104459 A1 | 4/2018 | Anand et al. |
| 2018/0107798 A1 | 4/2018 | Hu |
| 2018/0107998 A1 | 4/2018 | Pederson |
| 2018/0140810 A1 | 5/2018 | Cataltepe |
| 2018/0193562 A1 | 7/2018 | Gibson et al. |
| 2018/0256892 A1* | 9/2018 | Wong ...................... A61N 1/06 |
| 2018/0263752 A1 | 9/2018 | Pinchuk et al. |
| 2019/0030322 A1 | 1/2019 | Schulte et al. |
| 2019/0082990 A1 | 3/2019 | Poltorak |
| 2019/0105019 A1 | 4/2019 | Pagoulatos et al. |
| 2019/0151239 A1* | 5/2019 | Abrams ................ A61P 25/08 |
| 2019/0167964 A1* | 6/2019 | Lewis .............. A61M 39/0247 |
| 2019/0218334 A1 | 7/2019 | Delaney, Jr. et al. |
| 2019/0246989 A1 | 8/2019 | Genov et al. |
| 2019/0282802 A1 | 9/2019 | Malinowski |
| 2019/0321106 A1 | 10/2019 | Bergman et al. |

(56) References Cited

U.S. PATENT DOCUMENTS

| | | | | | |
|---|---|---|---|---|---|
| 2019/0351209 | A1 | 11/2019 | Butziger et al. | | |
| 2020/0061337 | A1 | 2/2020 | Singh et al. | | |
| 2020/0069254 | A1* | 3/2020 | Lange | | A61B 5/293 |
| 2020/0086538 | A1 | 3/2020 | Funaoka | | |
| 2020/0170542 | A1* | 6/2020 | Waziri | | A61B 5/065 |
| 2020/0338325 | A1 | 10/2020 | Shachar et al. | | |
| 2020/0375492 | A1* | 12/2020 | Govari | | A61B 5/369 |
| 2021/0077714 | A1 | 3/2021 | Bodner | | |
| 2021/0100990 | A1 | 4/2021 | Yoo et al. | | |
| 2021/0205623 | A1 | 7/2021 | Peterson et al. | | |
| 2021/0252266 | A1* | 8/2021 | Otto | | A61M 5/14276 |
| 2021/0260280 | A1 | 8/2021 | Gordon et al. | | |
| 2021/0327029 | A1 | 10/2021 | Chen et al. | | |
| 2021/0338992 | A1 | 11/2021 | Bertrand | | |
| 2021/0386982 | A1 | 12/2021 | Lad et al. | | |
| 2021/0397970 | A1 | 12/2021 | Cherian et al. | | |
| 2022/0016338 | A1 | 1/2022 | Abrams et al. | | |
| 2022/0016402 | A1 | 1/2022 | Abrams et al. | | |
| 2022/0016404 | A1 | 1/2022 | Abrams et al. | | |
| 2022/0022800 | A1 | 1/2022 | Abrams et al. | | |
| 2022/0249190 | A1 | 8/2022 | Kelly et al. | | |
| 2022/0331567 | A1 | 10/2022 | Abrams | | |
| 2023/0148923 | A1 | 5/2023 | Abrams et al. | | |
| 2023/0200707 | A1 | 6/2023 | Abrams et al. | | |
| 2023/0277840 | A1 | 9/2023 | Abrams et al. | | |
| 2024/0021313 | A1 | 1/2024 | Alkaitis et al. | | |

FOREIGN PATENT DOCUMENTS

| | | | | | |
|---|---|---|---|---|---|
| DE | 102013002763 | A1 | 8/2014 | | |
| EP | 0904119 | A1 | 3/1999 | | |
| EP | 0995460 | A2 | 4/2000 | | |
| EP | 1281758 | A2 | 2/2003 | | |
| EP | 1391219 | A2 | 2/2004 | | |
| EP | 1391219 | A3 | 5/2004 | | |
| EP | 1798243 | A2 | 6/2007 | | |
| EP | 3028727 | A1 | 6/2016 | | |
| JP | 2004533997 | A | 11/2004 | | |
| JP | 2007309746 | A | 11/2007 | | |
| KR | 102054445 | B1 | 12/2019 | | |
| WO | 9406690 | A1 | 3/1994 | | |
| WO | 9427587 | A2 | 12/1994 | | |
| WO | 96033761 | A1 | 10/1996 | | |
| WO | 0040716 | A2 | 7/2000 | | |
| WO | 0068378 | A1 | 11/2000 | | |
| WO | 0160397 | A1 | 8/2001 | | |
| WO | 0168836 | A2 | 9/2001 | | |
| WO | 0175164 | A2 | 10/2001 | | |
| WO | 0244321 | A2 | 6/2002 | | |
| WO | 02066516 | A2 | 8/2002 | | |
| WO | 02094185 | A2 | 11/2002 | | |
| WO | 03013582 | A1 | 2/2003 | | |
| WO | 03029459 | A2 | 4/2003 | | |
| WO | 03062401 | A2 | 7/2003 | | |
| WO | 03070884 | A2 | 8/2003 | | |
| WO | 03070903 | A2 | 8/2003 | | |
| WO | 03070918 | A2 | 8/2003 | | |
| WO | 03072713 | A2 | 9/2003 | | |
| WO | 03074566 | A2 | 9/2003 | | |
| WO | 03074654 | A2 | 9/2003 | | |
| WO | 2004009779 | A2 | 1/2004 | | |
| WO | 2004031412 | A2 | 4/2004 | | |
| WO | 2004039956 | A2 | 5/2004 | | |
| WO | 2004057017 | A2 | 7/2004 | | |
| WO | 2004066183 | A2 | 8/2004 | | |
| WO | 2004072248 | A2 | 8/2004 | | |
| WO | 2004111191 | A2 | 12/2004 | | |
| WO | 2004112411 | A1 | 12/2004 | | |
| WO | 2005000351 | A2 | 1/2005 | | |
| WO | 2005012523 | A1 | 2/2005 | | |
| WO | 2005017111 | A2 | 2/2005 | | |
| WO | 2005019453 | A2 | 3/2005 | | |
| WO | 2005023200 | A2 | 3/2005 | | |
| WO | 2005023986 | A2 | 3/2005 | | |
| WO | 2005033271 | A2 | 4/2005 | | |
| WO | 2005035769 | A2 | 4/2005 | | |
| WO | 2005041859 | A2 | 5/2005 | | |
| WO | 2005042705 | A2 | 5/2005 | | |
| WO | 2006068867 | A1 | 6/2006 | | |
| WO | 2007019618 | A1 | 2/2007 | | |
| WO | 2007070538 | A2 | 6/2007 | | |
| WO | 2008112017 | A2 | 9/2008 | | |
| WO | 2008115919 | A2 | 9/2008 | | |
| WO | 2008141321 | A1 | 11/2008 | | |
| WO | 2009014762 | A1 | 1/2009 | | |
| WO | 2009024562 | A1 | 2/2009 | | |
| WO | 2009151741 | A1 | 12/2009 | | |
| WO | 2010056712 | A1 | 5/2010 | | |
| WO | 2011097487 | A2 | 8/2011 | | |
| WO | 2013004843 | A1 | 1/2013 | | |
| WO | 2014064691 | A2 | 5/2014 | | |
| WO | 2014159757 | A2 | 10/2014 | | |
| WO | 2014188407 | A1 | 11/2014 | | |
| WO | 2015001008 | A1 | 1/2015 | | |
| WO | 2015197867 | A1 | 12/2015 | | |
| WO | 2016140853 | A1 | 9/2016 | | |
| WO | 2018023041 | A1 | 2/2018 | | |
| WO | 2018038930 | A1 | 3/2018 | | |
| WO | WO-2018153943 | A1* | 8/2018 | | A61B 5/01 |
| WO | 2019084038 | A1 | 5/2019 | | |
| WO | 2019136462 | A1 | 7/2019 | | |
| WO | 2019211314 | A1 | 11/2019 | | |
| WO | 2020160613 | A1 | 8/2020 | | |
| WO | 2020248067 | A1 | 12/2020 | | |
| WO | 2021150522 | A1 | 7/2021 | | |
| WO | 2022015941 | A1 | 1/2022 | | |
| WO | 2022020314 | A1 | 1/2022 | | |

OTHER PUBLICATIONS

Abrams et al., "Monitoring and Treatment Based on Continuous Intracranial EEG Activity," Cerebral Therapeutics, Inc. U.S. Appl. No. 63/054,522, filed Jul. 21, 2020, 24 pages.

Abrams et al., "Treatment and Monitoring of Diseases Associated With Elevated Intracranial Pressure or Hydrocephalus," Cerebral Therapeutics, Inc., U.S. Appl. No. 63/223,629, filed Jul. 20, 2021, 26 pages.

Abrams, Daniel, "Treatment and Monitoring of Post-Traumatic Stress Disorder," Cerebral Therapeutics, Inc., U.S. Appl. No. 63/166,705, filed Mar. 26, 2021, 21 pages.

Abrams, Daniel, "Treatment and Monitoring of Post-Traumatic Stress Disorder," Cerebral Therapeutics, Inc., U.S. Appl. No. 63/172,313, filed Apr. 8, 2021, 28 pages.

Written Opinion of the International Preliminary Examining Authority in PCT/US2021/042315, mailed Jun. 8, 2022, 8 pages.

International Preliminary Report on Patentability in PCT/US2021/042315, mailed Oct. 4, 2022, 22 pages.

International Search Report and Written Opinion in PCT/US2021/042315, mailed Oct. 8, 2021, 14 pages.

Stremlau et al., "The cytoplasmic body component TRIM5a restricts HIV-1 infection in Old World monkeys." Nature 427.6977 (2004): 848-853.

Sugiyama et al., "RNA-dependent RNA polymerase is an essential component of a self-enforcing loop coupling heterochromatin assembly to siRNA production." Proceedings of the National Academy of Sciences 102.1 (2005): 152-157.

Suh et al., "Human embryonic stem cells express a unique set of microRNAs." Developmental biology 270.2 (2004): 488-498.

Sumimoto et al., "Gene therapy for human small-cell lung carcinoma by inactivation of Skp-2 with virally mediated RNA interference." Gene therapy 12.1 (2005): 95-100.

Sun et al., "Development of a micro-array to detect human and mouse microRNAs and characterization of expression in human organs." Nucleic acids research 32.22 (2004): e188-e188.

Sunkar et al., "Novel and stress-regulated microRNAs and other small RNAs from Arabidopsis." The Plant Cell 16.8 (2004): 2001-2019.

Sussman et al., "Neuroanatomical features in soldiers with post-traumatic stress disorder." BMC neuroscience 17.1 (2016): 1-11.

(56)                    References Cited

OTHER PUBLICATIONS

Suzuma et al., "Identification and characterization of novel small RNAs in the aspS-yrvM intergenic region of the Bacillus subtilis genome." Microbiology 148.8 (2002): 2591-2598.

Svennerholm et al., "Alzheimer disease-effect of continuous intracerebroventricular treatment with GM1 ganglioside and a systematic activation programme." Dementia and geriatric cognitive disorders 14.3 (2002): 128-136.

Swagerman et al., "The Computerized Neurocognitive Battery: Validation, aging effects, and heritability across cognitive domains." Neuropsychology 30.1 (2016): 53-64.

Sygnus® Implantable Connector System, Balseal.com, Retrieved from the Internet: <URL: https://www.balseal.com/contact/sygnus/> (2024): 1-13.

Szymanski et al., "Noncoding RNA transcripts." Journal of applied genetics 44.1 (2003): 1-20.

Tabara et al., "The dsRNA binding protein RDE-4 interacts with RDE-1, DCR-1, and a DExH-box helicase to direct RNAi in C. elegans." Cell 109.7 (2002): 861-871.

Tabara et al., "The rde-1 gene, RNA interference, and transposon silencing in C. elegans." Cell 99.2 (1999): 123-132.

Takamizawa et al., "Reduced expression of the let-7 microRNAs in human lung cancers in association with shortened postoperative survival." Cancer research 64.11 (2004): 3753-3756.

Tan et al., "RNAi, a new therapeutic strategy against viral infection." Cell research 14.6 (2004): 460-466.

Tang et al., "A biochemical framework for RNA silencing in plants." Genes & development 17.1 (2003): 49-63.

Tang,G. "siRNA and miRNA: an insight into RISCs." Trends in biochemical sciences 30.2 (2005): 106-114.

Tanno et al., "Silencing of endogenous IGFBP-5 by micro RNA interference affects proliferation, apoptosis and differentiation of neuroblastoma cells." Cell Death & Differentiation 12.3 (2005): 213-223.

Tanzer et al., "Evolution of microRNAs located within Hox gene clusters." Journal of Experimental Zoology Part B: Molecular and Developmental Evolution 304.1 (2005): 75-85.

Tanzer et al., "Molecular evolution of a microRNA cluster." Journal of molecular biology 339.2 (2004): 327-335.

Taylor et al., "The potential of RNA interference as a tool in the management of viral hepatitis." Journal of hepatology 42.1 (2005): 139-144.

Teixeira et al., "Multiple numerical chromosome aberrations in cancer: what are their causes and what are their consequences." Seminars in cancer biology. vol. 15. No. 1. Academic Press (2005): 3-12.

Teixeira et al., "Processing bodies require RNA for assembly and contain nontranslating mRNAs." Rna 11.4 (2005): 371-382.

Thiagarajan, T. "EEG and FMRI Papers by the Numbers," Sapien Labs, Retrieved from the Internet: <URL: https://sapienlabs.org/lab-talk/500000-human-neuroscience-papers/> (2016): 1-7.

Thomas et al., "Size constraints for targeting post-transcriptional gene silencing and for RNA-directed methylation in Nicotiana benthamiana using a potato virus X vector." The Plant Journal 25.4 (2001): 417-425.

Thomson et al., "A custom microarray platform for analysis of microRNA gene expression." Nature methods 1.1 (2004): 47-53.

Thurman et al., "Traumatic brain injury in the United States: a public health perspective." The Journal of head trauma rehabilitation 14.6 (1999): 602-615.

Tijsterman et al., "Dicers at RISC: the mechanism of RNAi." Cell 117.1 (2004): 1-3.

Tomari et al., "A protein sensor for siRNA asymmetry." Science 306.5700 (2004): 1377-1380.

Tomari et al., "MicroRNA biogenesis: drosha can't cut it without a partner." Current Biology 15.2 (2005): R61-R64.

Tomari et al., "Perspective: machines for RNAi." Genes & development 19.5 (2005): 517-529.

Tops et al., "RDE-2 interacts with MUT-7 to mediate RNA interference in Caenorhabditis elegans." Nucleic acids research 33.1 (2005): 347-355.

Trainor, P. "Developmental Biology Is "Cruzing"." Developmental Cell 7.4 (2004): 481-486.

Trivedi et al., "The Inventory of Depressive Symptomatology, Clinician Rating (IDS-C) and Self-Report (IDS-SR), and the Quick Inventory of Depressive Symptomatology, Clinician Rating (QIDS-C) and Self-Report (QIDS-SR) in public sector patients with mood disorders: a psychometric evaluation." Psychological medicine 34.1 (2004): 73-82.

Trousselard et al., "Is plasma GABA level a biomarker of post-traumatic stress disorder (PTSD) severity? A preliminary study." Psychiatry research 241 (2016): 273-279.

Tucker et al., "Efficacy and safety of topiramate monotherapy in civilian posttraumatic stress disorder: a randomized, double-blind, placebo-controlled study." Journal of Clinical Psychiatry 68.2 (2007): 201-206.

Turner et al., "Review of recent methodological developments in group-randomized trials: part 1—design." American journal of public health 107.6 (2017): 907-915.

Turner et al., "Review of recent methodological developments in group-randomized trials: part 2—analysis." American journal of public health 107.7 (2017): 1078-1086.

Tuschl et al., "Targeted mRNA degradation by double-stranded RNA in vitro." Genes & development 13.24 (1999): 3191-3197.

Tuschl T., "RNA sets the standard." Nature 421.6920 (2003): 220-221.

U.S. Appl. No. 17/380,415, filed Jul. 20, 2021, 71 pages.

U.S. Appl. No. 17/380,694, filed Jul. 20, 2021, 37 pages.

U.S. Appl. No. 17/868,321, filed Jul. 19, 2022, 24 pages.

U.S. Appl. No. 63/053,864, filed Jul. 20, 2020, 39 pages.

U.S. Appl. No. 63/280,367, filed Nov. 17, 2021, 54 pages.

U.S. Appl. No. 63/294,611, filed Dec. 29, 2021, 38 pages.

U.S. Appl. No. 63/310,288, filed Feb. 15, 2022, 55 pages.

Uchida et al., "A novel role of the mammalian GSPT/eRF3 associating with poly (A)-binding protein in Cap/Poly (A)-dependent translation." Journal of Biological Chemistry 277.52 (2002): 50286-50292.

Ullman et al., "Psychosocial correlates of PTSD symptom severity in sexual assault survivors." Journal of traumatic stress 20.5 (2007): 821-831.

Mccaffrey et al., "RNA interference in adult mice." Nature 418.6893 (2002): 38-39.

Mchale et al., "MicroRNA-directed cleavage of Nicotiana sylvestris PHAVOLUTA mRNA regulates the vascular cambium and structure of apical meristems." The Plant Cell 16.7 (2004): 1730-1740.

Mcmanus et al., "Gene silencing using micro-RNA designed hairpins." Rna 8.6 (2002): 842-850.

Mcmanus, M. "MicroRNAs and cancer." Seminars in cancer biology. vol. 13. No. 4. Academic Press (2003): 253-258.

Mehta et al., "EEG abnormalities in children with speech and language impairment." Journal of Clinical and Diagnostic Research: JCDR 9.7 (2015): CC04-CC07.

Meister et al., "Human Argonaute2 mediates RNA cleavage targeted by miRNAs and siRNAs." Molecular cell 15.2 (2004): 185-197.

Meister et al., "Mechanisms of gene silencing by double-stranded RNA." Nature 431.7006 (2004): 343-349.

Meister et al., "Sequence-specific inhibition of microRNA-and siRNA-induced RNA silencing." Rna 10.3 (2004): 544-550.

Merkle et al., "Biological significance of a human enterovirus B-specific RNA element in the 3' nontranslated region." Journal of virology 76.19 (2002): 9900-9909.

Meshorer et al., "Alternative splicing and neuritic mRNA translocation under long-term neuronal hypersensitivity." Science 295. 5554 (2002): 508-512.

Mette et al., "Transcriptional silencing and promoter methylation triggered by double-stranded RNA." The EMBO journal (2000): 5194-5201.

Metzler et al., "High expression of precursor microRNA-155/BIC RNA in children with Burkitt lymphoma." Genes, Chromosomes and Cancer 39.2 (2004): 167-169.

(56) References Cited

OTHER PUBLICATIONS

Meyerhoff et al., "Cortical gamma-aminobutyric acid and glutamate in posttraumatic stress disorder and their relationships to self-reported sleep quality." Sleep 37.5 (2014): 893-900.

Michael et al., "Reduced accumulation of specific microRNAs in colorectal neoplasia." Molecular cancer research 1.12 (2003): 882-891.

Milligan et al., "Turnover of primary transcripts is a major step in the regulation of mouse H19 gene expression." EMBO reports (2002): 774-779.

Miska et al., "Microarray analysis of microRNA expression in the developing mammalian brain." Genome biology 5.9 (2004): 1-13.

Mithoefer et al., "Durability of improvement in post-traumatic stress disorder symptoms and absence of harmful effects or drug dependency after 3, 4-methylenedioxymethamphetamine-assisted psychotherapy: a prospective long-term follow-up study." Journal of psychopharmacology 27.1 (2013): 28-39.

Mithoefer et al., "The safety and efficacy of±3, 4-methylenedioxymethamphetamine-assisted psychotherapy in subjects with chronic, treatment-resistant posttraumatic stress disorder: the first randomized controlled pilot study." Journal of psychopharmacology 25.4 (2011): 439-452.

Mlotshwa et al., "RNA silencing and the mobile silencing signal." The Plant Cell 14.suppl_1 (2002): S289-S301.

Mochizuki et al., "Analysis of a piwi-related gene implicates small RNAs in genome rearrangement in Tetrahymena." Cell 110.6 (2002): 689-699.

Modarres et al., "Strong correlation of novel sleep electroencephalography coherence markers with diagnosis and severity of posttraumatic stress disorder." Scientific reports 9.1 (2019): 1-10.

Mollinari et al., "Ablation of PRC1 by small interfering RNA demonstrates that cytokinetic abscission requires a central spindle bundle in mammalian cells, whereas completion of furrowing does not." Molecular biology of the cell 16.3 (2005): 1043-1055.

Moore et al., "Psychometric properties of the penn computerized neurocognitive battery." Neuropsychology 29.2 (2015): 235-246.

Morel et al., "Fertile hypomorphic ARGONAUTE (ago1) mutants impaired in post-transcriptional gene silencing and virus resistance." The Plant Cell 14.3 (2002): 629-639.

Morey et al., "Amygdala volume changes in posttraumatic stress disorder in a large case-controlled veterans group." Archives of general psychiatry 69.11 (2012): 1169-1178.

Morris et al., "Small interfering RNA-induced transcriptional gene silencing in human cells." Science 305.5688 (2004): 1289-1292.

Moss et al., "Conservation of the heterochronic regulator Lin-28, its developmental expression and microRNA complementary sites." Developmental biology 258.2 (2003): 432-442.

Moss et al., "The cold shock domain protein LIN-28 controls developmental timing in C. elegans and is regulated by the lin-4 RNA." Cell 88.5 (1997): 637-646.

Moss, E. "MicroRNAs: hidden in the genome." Current Biology 12.4 (2002): R138-R140.

Moss, E. "RNA interference: it's a small RNA world." Current Biology 11.19 (2001): R772-R775.

Mourelatos et al., "miRNPs: a novel class of ribonucleoproteins containing numerous microRNAs." Genes & development 16.6 (2002): 720-728.

Mourrain et al., "Arabidopsis SGS2 and SGS3 genes are required for posttranscriptional gene silencing and natural virus resistance." Cell 101.5 (2000): 533-542.

Muller et al., "The GAD65 knock out mouse-a model for GABAergic processes in fear-and stress-induced psychopathology." Genes, Brain and Behavior 14.1 (2015): 37-45.

Murchison et al., "miRNAs on the move: miRNA biogenesis and the RNAi machinery." Current opinion in cell biology 16.3 (2004): 223-229.

Nagy et al., "Anti-anxiety action op diazepam after intraamygdaloid application in the rat." Neuropharmacology 18.6 (1979): 573-576.

Nakahara et al., "Expanding roles for miRNAs and siRNAs in cell regulation." Current opinion in cell biology 16.2 (2004): 127-133.

Neilson et al., "Herpesviruses throw a curve ball: new insights into microRNA biogenesis and evolution." Nature Methods 2.4 (2005): 252-254.

Nelson et al., "Microarray-based, high-throughput gene expression profiling of microRNAs." Nature methods 1.2 (2004): 155-161.

Nelson et al., "miRNP: mRNA association in polyribosomes in a human neuronal cell line." Rna 10.3 (2004): 387-394.

Nelson et al., "The microRNA world: small is mighty." Trends in biochemical sciences 28.10 (2003): 534-540.

Neugebauer, R. "Reliability of seizure diaries in adult epileptic patients." Neuroepidemiology 8.5 (1989): 228-233.

Ngo et al., "Double-stranded RNA induces mRNA degradation in Trypanosoma brucei." Proceedings of the National Academy of Sciences 95.25 (1998): 14687-14692.

Nicholson et al., "Molecular characterization of a mouse cDNA encoding Dicer, a ribonuclease III ortholog involved in RNA interference." Mammalian Genome 13.2 (2002): 67-73.

Nijholt et al., "Stress-induced alternative splicing of acetylcholinesterase results in enhanced fear memory and long-term potentiation." Molecular psychiatry 9.2 (2004): 174-183.

Nikitin et al., "Protein synthesis inhibitor administration before a reminder caused recovery from amnesia induced by memory reconsolidation impairment with NMDA glutamate receptor antagonist." Brain Research Bulletin 171 (2021): 44-55.

Nilsson et al., "Enhanced detection and distinction of RNA by enzymatic probe ligation." Nature biotechnology 18.7 (2000): 791-793.

Nilsson et al., "Making ends meet in genetic analysis using padlock probes." Human mutation 19.4 (2002): 410-415.

Nishitsuji et al., "Expression of small hairpin RNA by lentivirus-based vector confers efficient and stable gene-suppression of HIV-1 on human cells including primary non-dividing cells." Microbes and infection 6.1 (2004): 76-85.

Noguchi et al., "Regulation of gene expression by sodium valproate in epithelial-to-mesenchymal transition." Lung 193.5 (2015): 691-700.

Novak et al., "Expression of BCMA, TACI, and BAFF-R in multiple myeloma: a mechanism for growth and survival." Blood 103.2 (2004): 689-694.

Karube et al., "Reduced expression of Dicer associated with poor prognosis in lung cancer patients." Cancer science 96.2 (2005): 111-115.

Kasashima et al., "Altered expression profiles of microRNAs during TPA-induced differentiation of HL-60 cells." Biochemical and biophysical research communications 322.2 (2004): 403-410.

Kasschau et al., "P1/HC-Pro, a viral suppressor of RNA silencing, interferes with *Arabidopsis* development and miRNA function." Developmental cell 4.2 (2003): 205-217.

Katyal et al., "The relationship of triphasic waves with intracranial pressure as a possible prognostic marker in traumatic brain injury." Case reports in neurological medicine 2017.1 (2017): 1-4.

Kawasaki et al., "Hes1 is a target of microRNA-23 during retinoic-acid-induced neuronal differentiation of NT2 cells." Nature 423. 6942 (2003): 838-842.

Kawasaki et al., "Retraction: Hes1 is a target of microRNA-23 during retinoic-acid-induced neuronal differentiation of NT2 cells." Nature 426 (2003): 100.

Kawasaki et al., "Short hairpin type of dsRNAs that are controlled by tRNA Val promoter significantly induce RNAi-mediated gene silencing in the cytoplasm of human cells." Nucleic acids research 31.2 (2003): 700-707.

Kawasaki et al., "siRNAs generated by recombinant human Dicer induce specific and significant but target site-independent gene silencing in human cells." Nucleic acids research 31.3 (2003): 981-987.

Kawasaki et al., "World of small RNAs: from ribozymes to siRNA and miRNA." Differentiation 72.2-3 (2004): 58-64.

Kazdin A., "Mediators and mechanisms of change in psychotherapy research." Review of Clinical Psychology 3.1 (2007): 1-27.

Keck Jr et al., "Valproate and carbamazepine in the treatment of panic and posttraumatic stress disorders, withdrawal states, and behavioral dyscontrol syndromes." Journal of Clinical psychopharmacology 12.1 (1992): 36S-41S.

(56)     References Cited

OTHER PUBLICATIONS

Keck Jr et al., "Valproate treatment of panic disorder and lactate-induced panic attacks." Biological Psychiatry 33.7 (1993): 542-546.

Kelmendi et al., "PTSD: from neurobiology to pharmacological treatments." European journal of psychotraumatology 7.1 (2016): 1-12.

Kennerdell et al., "Heritable gene silencing in *Drosophila* using double-stranded RNA." Nature biotechnology 18.8 (2000): 896-898.

Kent et al., "Conservation, regulation, synteny, and introns in a large-scale C. briggsae-C. elegans genomic alignment." Genome research 10.8 (2000): 1115-1125.

Kent et al., "RNAi: running interference for the cell." Organic & biomolecular chemistry 2.14 (2004): 1957-1961.

Kent W., "BLAT—the BLAST-like alignment tool." Genome research 12.4 (2002): 656-664.

Kessler et al., "Posttraumatic stress disorder in the National Comorbidity Survey." Archives of General Psychiatry 52.12 (1995): 1048-1060.

Kessler et al., "Probing the role of compartmentation of glycolysis in procyclic form Trypanosoma brucei: RNA interference studies of PEX14, hexokinase, and phosphofructokinase." Journal of Biological Chemistry 280.10 (2005): 9030-9036.

Ketting et al., "Dicer functions in RNA interference and in synthesis of small RNA involved in developmental timing in C. elegans." Genes & development 15.20 (2001): 2654-2659.

Khvorova et al., "Functional siRNAs and miRNAs exhibit strand bias." Cell 115.2 (2003): 209-216.

Kida S., "Reconsolidation/destabilization, extinction and forgetting of fear memory as therapeutic targets for PTSD." Psychopharmacology 236.1 (2019): 49-57.

Kidner et al., "Spatially restricted microRNA directs leaf polarity through ARGONAUTE1." Nature 428.6978 (2004): 81-84.

Kidner et al., "The developmental role of microRNA in plants." Current opinion in plant biology 8.1 (2005): 38-44.

Kim et al., "Identification of many microRNAs that copurify with polyribosomes in mammalian neurons." Proceedings of the National Academy of Sciences 101.1 (2004): 360-365.

Kim et al., "Stress effects on the hippocampus: a critical review." Learning & memory 22.9 (2015): 411-416.

Kim et al., "Synthetic dsRNA Dicer substrates enhance RNAi potency and efficacy." Nature biotechnology 23.2 (2005): 222-226.

Kim V., "MicroRNA biogenesis: coordinated cropping and dicing." Nature reviews Molecular cell biology 6.5 (2005): 376-385.

Kim V., "MicroRNA precursors in motion: exportin-5 mediates their nuclear export." Trends in cell biology 14.4 (2004): 156-159.

Kiriakidou et al., "A combined computational-experimental approach predicts human microRNA targets." Genes & development 18.10 (2004): 1165-1178.

Kittler et al., "An endoribonuclease-prepared siRNA screen in human cells identifies genes essential for cell division." Nature 432.7020 (2004): 1036-1040.

Klahre et al., "High molecular weight RNAs and small interfering RNAs induce systemic posttranscriptional gene silencing in plants." Proceedings of the National Academy of Sciences 99.18 (2002): 11981-11986.

Klein et al., "RSEARCH: finding homologs of single structured RNA sequences." BMC bioinformatics 4.1 (2003): 1-16.

Knott et al., "Transgenic RNA interference reveals role for mouse sperm phospholipase C? in triggering Ca2+ oscillations during fertilization." Biology of reproduction 72.4 (2005): 992-996.

Komano et al., "Inhibiting the Arp2/3 complex limits infection of both intracellular mature vaccinia virus and primate lentiviruses." Molecular biology of the cell 15.12 (2004): 5197-5207.

Kondziella et al., "Continuous EEG monitoring in aneurysmal subarachnoid hemorrhage: a systematic review." Neurocritical care 22.3 (2015): 450-461.

Konforti B., "The news and you." Nature structural biology 10.3 (2003): 1-1.

Koziczak et al., "Cooperation between fibroblast growth factor receptor-4 and ErbB2 in regulation of cyclin D1 translation." Journal of Biological Chemistry 279.48 (2004): 50004-50011.

Krediet et al., "Reviewing the potential of psychedelics for the treatment of PTSD." International Journal of Neuropsychopharmacology 23.6 (2020): 385-400.

Krek et al., "Combinatorial microRNA target predictions." Nature genetics 37.5 (2005): 495-500.

Krichevsky et al., "A microRNA array reveals extensive regulation of microRNAs during brain development." Rna 9.10 (2003): 1274-1281.

Krol et al., "Structural features of microRNA (miRNA) precursors and their relevance to miRNA biogenesis and small interfering RNA/short hairpin RNA design." Journal of Biological Chemistry 279.40 (2004): 42230-42239.

Krugers et al., "Chronic stress effects on hippocampal structure and synaptic function: relevance for depression and normalization by anti-glucocorticoid treatment." Frontiers in synaptic neuroscience 2 (2010): 24.

Krutzfeldt et al., "Silencing of microRNAs in vivo with 'antagomirs'." nature 438.7068 (2005): 1-5.

Krysinska et al., "Post-traumatic stress disorder and suicide risk: a systematic review." Archives of suicide research 14.1 (2010): 1-23.

Krystal et al., "Adjunctive risperidone treatment for antidepressant-resistant symptoms of chronic military service-related PTSD: A randomized trial." Jama 306.5 (2011): 493-502.

Kuhn et al., "Gray matter correlates of posttraumatic stress disorder: a quantitative meta-analysis." Biological psychiatry 73.1 (2013): 70-74.

Kurihara et al., "*Arabidopsis* micro-RNA biogenesis through Dicer-like 1 protein functions." Proceedings of the National Academy of Sciences 101.34 (2004): 12753-12758.

Kuwabara et al., "A small modulatory dsRNA specifies the fate of adult neural stem cells." Cell 116.6 (2004): 779-793.

Lagos-Quintana et al., "Identification of novel genes coding for small expressed RNAs." Science 294.5543 (2001): 853-858.

Popoli et al., "The stressed synapse: the impact of stress and glucocorticoids on glutamate transmission." Nature Reviews Neuroscience 13.1 (2012): 22-37.

Posner et al., "The Columbia—Suicide Severity Rating Scale: initial validity and internal consistency findings from three multisite studies with adolescents and adults." American journal of psychiatry 168.12 (2011): 1266-1277.

Post et al., "Sensitization and kindling: implications for the evolving neural substrates of post-traumatic stress disorder." Neurobiological and Clinical Consequences of Stress: From Normal Adaptation to PTSD (1995): 1-22.

Post-Traumatic Stress Disorder (PTSD), National Institute of Mental Health, Retrieved from the Internet: <URL: https://www.nimh.nih.gov/health/statistics/post-traumatic-stress-disorder-ptsd> (2017): 1-4.

Poy et al., "A pancreatic islet-specific microRNA regulates insulin secretion." Nature 432.7014 (2004): 226-230.

Primeau et al., "Valproic acid and panic disorder." The Canadian Journal of Psychiatry 35.3 (1990): 248-250.

Provost et al., "Ribonuclease activity and RNA binding of recombinant human Dicer." The EMBO journal (2002): 1-11.

Puerta-Fernandez et al., "Anchoring hairpin ribozymes to long target RNAs by loop-loop RNA interactions." Antisense and Nucleic Acid Drug Development 12.1 (2002): 1-9.

Puetz et al., "Effects of pharmacotherapy on combat-related PTSD, anxiety, and depression: a systematic review and meta-regression analysis." PloS one 10.5 (2015): 1-18.

Qassem et al., "Psychiatric co-morbidities in post-traumatic stress disorder: detailed findings from the adult psychiatric morbidity survey in the English population." Psychiatric Quarterly 92.1 (2021): 321-330.

Qi et al., "Inhibition of cell growth and shoot development by a specific nucleotide sequence in a noncoding viroid RNA." The Plant Cell 15.6 (2003): 1360-1374.

Rajewsky et al., "Computational identification of microRNA targets." Genome Biology 5.2 (2004): 1-34.

(56)         References Cited

OTHER PUBLICATIONS

Rao, M. "Conserved and divergent paths that regulate self-renewal in mouse and human embryonic stem cells." Developmental biology 275.2 (2004): 269-286.

Rapaport et al., "Posttraumatic stress disorder and quality of life: results across 64 weeks of sertraline treatment." Journal of Clinical Psychiatry 63.1 (2002): 59-65.

Rapaport et al., "Quality-of-life impairment in depressive and anxiety disorders." American Journal of Psychiatry 162.6 (2005): 1171-1178.

Rapozzi et al., "Efficient silencing of bcr/abl oncogene by single- and double-stranded siRNAs targeted against b2a2 transcripts." Biochemistry 43.51 (2004): 16134-16141.

Raskind et al., "Trial of prazosin for post-traumatic stress disorder in military veterans." New England Journal of Medicine 378.6 (2018): 507-517.

Rauch et al., "Neurocircuitry models of posttraumatic stress disorder and extinction: human neuroimaging research—past, present, and future." Biological psychiatry 60.4 (2006): 376-382.

Ravindran et al., "Pharmacotherapy of PTSD: premises, principles, and priorities." Brain research 1293 (2009): 24-39.

Reff et al., "Depletion of B cells in vivo by a chimeric mouse human monoclonal antibody to CD20." (1994): 435-445.

Rehmsmeier et al., "Fast and effective prediction of microRNA/target duplexes." Rna 10.10 (2004): 1507-1517.

Reiner et al., "Identifying differentially expressed genes using false discovery rate controlling procedures." Bioinformatics 19.3 (2003): 368-375.

Reinhart et al., "MicroRNAs in plants." Genes & development 16.13 (2002): 1616-1626.

Reinhart et al., "Small RNAs correspond to centromere heterochromatic repeats." science 297.5588 (2002): 1831-1831.

Reinhart et al., "The 21-nucleotide let-7 RNA regulates developmental timing in Caenorhabditis elegans." nature 403.6772 (2000): 901-906.

Rhoades et al., "Prediction of plant microRNA targets." cell 110.4 (2002): 513-520.

Rhoda et al., "Studies with staggered starts: multiple baseline designs and group-randomized trials." American Journal of Public Health 101.11 (2011): 2164-2169.

Richards et al., "Sleep disturbance in PTSD and other anxiety-related disorders: an updated review of clinical features, physiological characteristics, and psychological and neurobiological mechanisms." Neuropsychopharmacology 45.1 (2020): 55-73.

Richter-Levin et al., "Animal models of PTSD: a challenge to be met." Molecular psychiatry 24.8 (2019): 1135-1156.

Riedel et al., "Glutamate receptor function in learning and memory." Behavioural brain research 140.1-2 (2003): 1-47.

Rinker et al., "Outcomes of short-gap sensory nerve injuries reconstructed with processed nerve allografts from a multicenter registry study." Journal of reconstructive microsurgery 31.05 (2015): 384-390.

Rivas et al., "Purified Argonaute2 and an siRNA form recombinant human RISC." Nature structural & molecular biology 12.4 (2005): 340-349.

Robb et al., "Specific and potent RNAi in the nucleus of human cells." Nature structural & molecular biology 12.2 (2005): 133-137.

Robins et al., "Incorporating structure to predict microRNA targets." Proceedings of the National Academy of Sciences 102.11 (2005): 4006-4009.

Robinson et al., "Genomic and proteomic analysis of multiple sclerosis: Opinion." Current opinion in immunology 15.6 (2003): 660-667.

Rodriguez et al., "Identification of mammalian microRNA host genes and transcription units." Genome research 14.10a (2004): 1902-1910.

Rose et al., "Blocking memory reconsolidation reverses memory-associated changes in glutamate receptor expression." Journal of Neuroscience 26.45 (2006): 11582-11587.

Roseboom et al., "Evidence in primates supporting the use of chemogenetics for the treatment of human refractory neuropsychiatric disorders." Molecular Therapy 29.12 (2021): 3484-3497.

Rosenbaum et al., "Ventriculostomy: Frequency, length of stay and in-hospital mortality in the United States of America, 1988-2010." Journal of Clinical Neuroscience 21.4 (2014): 623-632.

Rosok et al., "Systematic identification of sense-antisense transcripts in mammalian cells." Nature biotechnology 22.1 (2004): 104-108.

Rosso et al., "Insula and anterior cingulate GABA levels in post-traumatic stress disorder: preliminary findings using magnetic resonance spectroscopy." Depression and anxiety 31.2 (2013): 1-9.

Roth et al., "Expression profiling using a hexamer-based universal microarray." Nature biotechnology 22.4 (2004): 418-426.

Roy et al., "Deep learning-based electroencephalography analysis: a systematic review." Journal of neural engineering 16.5 (2019): 1-38.

Rudikoff et al., "Single amino acid substitution altering antigen-binding specificity." Proceedings of the National Academy of Sciences 79.6 (1982): 1979-1983.

Rush et al., "Clinical research challenges posed by difficult-to-treat depression." Psychological Medicine 52.3 (2022): 419-432.

Ruvkun et al., "The 20 years it took to recognize the importance of tiny RNAs." Cell 116 (2004): S93-S98.

Ruvkun, G., "Glimpses of a tiny RNA world." Science 294.5543 (2001): 797-799.

Ryan et al., "Antibody targeting of B-cell maturation antigen on malignant plasma cells." Molecular cancer therapeutics 6.11 (2007): 3009-3018.

Rye et al., "Interfering with cancer: a brief outline of advances in RNA interference in oncology." Tumor Biology 25.5-6 (2004): 329-336.

Ryo et al., "Identification and characterization of differentially expressed mRNAs in HIV type 1-infected human T cells." AIDS research and human retroviruses 16.10 (2000): 995-1005.

Liriano et al., "Ketamine as treatment for post-traumatic stress disorder: a review." Drugs in context 8 (2019): 1-7.

Litinskiy et al., "DCs induce CD40-independent immunoglobulin class switching through BLyS and APRIL." Nature immunology 3.9 (2002): 822-829.

Liu et al., "An oligonucleotide microchip for genome-wide microRNA profiling in human and mouse tissues." Proceedings of the National Academy of Sciences 101.26 (2004): 9740-9744.

Liu et al., "Argonaute2 is the catalytic engine of mammalian RNAi." Science 305.5689 (2004): 1437-1441.

Liu et al., "Chimeric mouse-human IgG1 antibody that can mediate lysis of cancer cells." Proceedings of the National Academy of Sciences 84.10 (1987): 3439-3443.

Liu et al., "High-oleic and high-stearic cottonseed oils: nutritionally improved cooking oils developed using gene silencing." Journal of the american College of nutrition 21.sup3 (2002): 205S-211S.

Liu et al., "High-stearic and high-oleic cottonseed oils produced by hairpin RNA-mediated post-transcriptional gene silencing." Plant physiology 129.4 (2002): 1732-1743.

Liu et al., "Optogenetic stimulation of a hippocampal engram activates fear memory recall." Nature 484.7394 (2012): 381-385.

Llave et al., "Cleavage of Scarecrow-like mRNA targets directed by a class of *Arabidopsis* miRNA." Science 297.5589 (2002): 2053-2056.

Llave et al., "Endogenous and silencing-associated small RNAs in plants." The Plant Cell 14.7 (2002): 1605-1619.

Llave et al., "Virus-encoded suppressor of posttranscriptional gene silencing targets a maintenance step in the silencing pathway." Proceedings of the National Academy of Sciences 97.24 (2000): 13401-13406.

Lolle et al., "Genome-wide non-mendelian inheritance of extra-genomic information in *Arabidopsis*." Nature 434.7032 (2005): 505-509.

Loscher, W. "Basic pharmacology of valproate: a review after 35 years of clinical use for the treatment of epilepsy." CNS drugs 16.10 (2002): 669-694.

(56)    References Cited

OTHER PUBLICATIONS

Lovett-Racke et al., "Silencing T-bet defines a critical role in the differentiation of autoreactive T lymphocytes." Immunity 21.5 (2004): 719-731.

Lu et al., "Adenovirus VA1 noncoding RNA can inhibit small interfering RNA and MicroRNA biogenesis." Journal of virology 78.23 (2004): 12868-12876.

Lu et al., "Characterization of small nontranslated polyadenylylated RNAs in vaccinia virus-infected cells." Proceedings of the National Academy of Sciences 93.5 (1996): 2037-2042.

Lu et al., "Modulation of angiogenesis with siRNA inhibitors for novel therapeutics." Trends in molecular medicine 11.3 (2005): 104-113.

Luciano et al., "RNA editing of a miRNA precursor." Rna 10.8 (2004): 1174-1177.

Lund et al., "Nuclear export of microRNA precursors." science 303.5654 (2004): 95-98.

Lutz, A. "Who joins the military? A look at race, class, and immigration status." Journal of Political & Military Sociology (2008): 167-188.

Ma et al., "Intrinsic direct repeats generate consistent post-transcriptional gene silencing in tobacco." The Plant Journal 31.1 (2002): 37-49.

Ma et al., "Structural basis for 5'-end-specific recognition of guide RNA by the A. fulgidus Piwi protein." Nature 434.7033 (2005): 666-670.

Maccallum et al., "Antibody-antigen interactions: contact analysis and binding site topography." Journal of molecular biology 262.5 (1996): 732-745.

Macdiarmid R., "RNA silencing in productive virus infections." Annu. Rev. Phytopathol. 43.1 (2005): 523-544.

Magruder et al., "The prevalence of PTSD across war eras and the effect of deployment on PTSD: A systematic review and meta-analysis." Psychiatric Annals 39.8 (2009): 778-788.

Mallory et al., "A viral suppressor of RNA silencing differentially regulates the accumulation of short interfering RNAs and micro-RNAs in tobacco." Proceedings of the National Academy of Sciences 99.23 (2002): 15228-15233.

Mallory et al., "HC-Pro suppression of transgene silencing eliminates the small RNAs but not transgene methylation or the mobile signal." The Plant Cell 13.3 (2001): 571-583.

Mallory et al., "MicroRNA control of PHABULOSA in leaf development: importance of pairing to the microRNA 5' region." The EMBO journal 23.16 (2004): 3356-3364.

Mallory et al., "MicroRNA regulation of NAC-domain targets is required for proper formation and separation of adjacent embryonic, vegetative, and floral organs." Current Biology 14.12 (2004): 1035-1046.

Mallory et al., "MicroRNAs: something important between the genes." Current opinion in plant biology 7.2 (2004): 120-125.

Maniataki et al., "Viroid RNA systemic spread may depend on the interaction of a 71-nucleotide bulged hairpin with the host protein VirP1." Rna 9.3 (2003): 346-354.

Mansfield et al., "MicroRNA-responsive 'sensor' transgenes uncover Hox-like and other developmentally regulated patterns of vertebrate microRNA expression." Nature genetics 36.10 (2004): 1079-1083.

Maquat L., "Nonsense-mediated mRNA decay: splicing, translation and mRNP dynamics." Nature reviews Molecular cell biology 5.2 (2004): 89-99.

Marillonnet et al., "In planta engineering of viral RNA replicons: efficient assembly by recombination of DNA modules delivered by Agrobacterium." Proceedings of the National Academy of Sciences 101.18 (2004): 6852-6857.

Markowitz et al., "Is exposure necessary? A randomized clinical trial of interpersonal psychotherapy for PTSD." American Journal of Psychiatry 172.5 (2015): 430-440.

Martens et al., "RNAi in Dictyostelium: the role of RNA-directed RNA polymerases and double-stranded RNase." Molecular biology of the cell 13.2 (2002): 445-453.

Martinez et al., "Single-stranded antisense siRNAs guide target RNA cleavage in RNAi." Cell 110.5 (2002): 563-574.

Masse et al., "Regulatory roles for small RNAs in bacteria." Current opinion in microbiology 6.2 (2003): 120-124.

Materials for Implantable Devices: Decoding Thermoplastic Polyurethanes, Lubrizol.com, Retrieved from the Internet: <URL: lubrizol.com/Health/Medical/Resource-Hub/Webinars/Materials-for-Implantable-Devices-Decoding-Thermoplastic-Polyurethanes> (2022): 1 page.

Mathews et al., "Expanded sequence dependence of thermodynamic parameters improves prediction of RNA secondary structure." Journal of molecular biology 288.5 (1999): 911-940.

Mathews, D. "Using an RNA secondary structure partition function to determine confidence in base pairs predicted by free energy minimization." Rna 10.8 (2004): 1178-1190.

Mattick et al., "Small regulatory RNAs in mammals." Human molecular genetics 14 (2005): R121-R132.

Mattick et al., "The evolution of controlled multitasked gene networks: the role of introns and other noncoding RNAs in the development of complex organisms." Molecular biology and evolution 18.9 (2001): 1611-1630.

Mattick, J. "Challenging the dogma: the hidden layer of non-protein-coding RNAs in complex organisms." Bioessays 25.10 (2003): 930-939.

Mattick, J. "Non-coding RNAs: the architects of eukaryotic complexity." EMBO reports (2001): 986-991.

Mattick, J. "The hidden genetic program of complex organisms." Scientific American 291.4 (2004): 60-67.

Matzke et al., "Genetic analysis of RNA-mediated transcriptional gene silencing." Biochimica et Biophysica Acta (BBA)-Gene Structure and Expression 1677.1-3 (2004): 129-141.

Matzke et al., "RNA-based silencing strategies in plants." Current opinion in genetics & development 11.2 (2001): 221-227.

Matzke et al., "RNA: guiding gene silencing." Science 293.5532 (2001): 1080-1083.

Max et al., "The lifetime cost of injury." Inquiry (1990): 332-343.

Boutet et al., "*Arabidopsis* HEN1: a genetic link between endogenous miRNA controlling development and siRNA controlling transgene silencing and virus resistance." Current Biology 13.10 (2003): 843-848.

Boutla et al., "Developmental defects by antisense-mediated inactivation of micro-RNAs 2 and 13 in *Drosophila* and the identification of putative target genes." Nucleic acids research 31.17 (2003): 4973-4980.

Boutla et al., "Induction of RNA interference in Caenorhabditis elegans by RNAs derived from plants exhibiting post-transcriptional gene silencing." Nucleic Acids Research 30.7 (2002): 1688-1694.

Bowman J., "Class III HD-Zip gene regulation, the golden fleece of ARGONAUTE activity." Bioessays 26.9 (2004): 938-942.

Bracht et al., "Trans-splicing and polyadenylation of let-7 microRNA primary transcripts." Rna 10.10 (2004): 1586-1594.

Bradley et al., "A multidimensional meta-analysis of psychotherapy for PTSD." American journal of Psychiatry 162.2 (2005): 214-227.

Brady et al., "Comorbidity of psychiatric disorders and post-traumatic stress disorder." Journal of clinical psychiatry 61 (2000): 22-32.

Brady et al., "Efficacy and safety of sertraline treatment of post-traumatic stress disorder: a randomized controlled trial." Jama 283.14 (2000): 1837-1844.

Brady et al., "Valproate treatment of comorbid panic disorder and affective disorders in two alcoholic patients." Journal of clinical psychopharmacology 14.1 (1994): 81-82.

Brandenberger et al., "Transcriptome characterization elucidates signaling networks that control human ES cell growth and differentiation." Nature biotechnology 22.6 (2004): 707-716.

Brantl S., "Antisense-RNA regulation and RNA interference." Biochimica et Biophysica Acta (BBA)-Gene Structure and Expression 1575.1-3 (2002): 15-25.

Brehm et al., "Parameters for establishing humanized mouse models to study human immunity: analysis of human hematopoietic stem cell engraftment in three immunodeficient strains of mice bearing the IL2rγnull mutation." Clinical immunology 135.1 (2010): 84-98.

(56)                References Cited

OTHER PUBLICATIONS

Bremner et al., "Chronic PTSD in Vietnam combat veterans: course of illness and substance abuse." The American journal of psychiatry 153.3 (1996): 369-375.

Bremner et al., "Decreased benzodiazepine receptor binding in prefrontal cortex in combat-related posttraumatic stress disorder." American Journal of Psychiatry 157.7 (2000): 1120-1126.

Bremner et al., "MRI and PET study of deficits in hippocampal structure and function in women with childhood sexual abuse and posttraumatic stress disorder." American journal of psychiatry 160.5 (2003): 924-932.

Bremner et al., "Neural correlates of declarative memory for emotionally valenced words in women with posttraumatic stress disorder related to early childhood sexual abuse." Biological psychiatry 53.10 (2003): 879-889.

Bremner et al., "Positron emission tomographic imaging of neural correlates of a fear acquisition and extinction paradigm in women with childhood sexual-abuse-related post-traumatic stress disorder." Psychological medicine 35.6 (2005): 791-806.

Bremner J., "Alterations in brain structure and function associated with post-traumatic stress disorder." Seminars in clinical neuropsychiatry 4.4 (1999):249-255.

Bremner J., "Neuroimaging in posttraumatic stress disorder and other stress-related disorders." Neuroimaging Clinics of North America 17.4 (2007): 523-538.

Brennecke et al., "bantam encodes a developmentally regulated microRNA that controls cell proliferation and regulates the proapoptotic gene hid in Drosophila." Cell 113.1 (2003): 25-36.

Brennecke et al., "Principles of microRNA-target recognition." PLoS biology 3.3 (2005): 1-15.

Brenner et al., "Gene expression analysis by massively parallel signature sequencing (MPSS) on microbead arrays." Nature biotechnology 18.6 (2000): 630-634.

Brezinsky et al., "A simple method for enriching populations of transfected CHO cells for cells of higher specific productivity." Journal of immunological methods 277.1-2 (2003): 141-155.

Bridge et al., "Induction of an interferon response by RNAi vectors in mammalian cells." Nature genetics 34.3 (2003): 263-264.

Brill et al., "Chronic valproic acid treatment triggers increased neuropeptide y expression and signaling in rat nucleus reticularis thalami." Journal of Neuroscience 26.25 (2006): 6813-6822.

Brooks et al., "Long-term survival after traumatic brain injury part II: Life expectancy." Archives of physical medicine and rehabilitation 96.6 (2015): 1000-1005.

Brown et al., "A computational view of microRNAs and their targets." Drug Discovery Today 10.8 (2005): 595-601.

Brown et al., "Neural systems for cognitive and emotional processing in posttraumatic stress disorder." Frontiers in psychology 3 (2012): 1-14.

Brown et al., "The stepped wedge trial design: a systematic review." BMC medical research methodology 6.1 (2006): 1-9.

Bryant R., "Post-traumatic stress disorder: a state-of-the-art review of evidence and challenges." World psychiatry 18.3 (2019): 259-269.

Bucherelli et al., "Aversive memory reactivation engages in the amygdala only some neurotransmitters involved in consolidation." Learning & Memory 13.4 (2006): 426-430.

Buck et al., "Design strategies and performance of custom DNA sequencing primers." Biotechniques 27.3 (1999): 528-536.

Cai et al., "Human microRNAs are processed from capped, polyadenylated transcripts that can also function as mRNAs." Rna 10.12 (2004): 1957-1966.

Cai et al., "Kaposi's sarcoma-associated herpesvirus expresses an array of viral microRNAs in latently infected cells." Proceedings of the National Academy of Sciences 102.15 (2005): 5570-5575.

Calin et al., "Frequent deletions and down-regulation of micro-RNA genes miR15 and miR 16 at 13q14 in chronic lymphocytic leukemia." Proceedings of the national academy of sciences 99.24 (2002): 15524-15529.

Calin et al., "Human microRNA genes are frequently located at fragile sites and genomic regions involved in cancers." Proceedings of the National Academy of Sciences 101.9 (2004): 2999-3004.

Calin et al., "MicroRNA profiling reveals distinct signatures in B cell chronic lymphocytic leukemias." Proceedings of the National Academy of Sciences 101.32 (2004): 11755-11760.

Cao et al., "Role of the DRM and CMT3 methyltransferases in RNA-directed DNA methylation." Current biology 13.24 (2003): 2212-2217.

Carbothane® 134 HG—Product Data Sheet, Carboline.com, Retrieved from the Internet: <URL:https://msds.carboline.com/servlet/FeedFile/1/prod/0859/PDS%3A%7BPC%3A0859%3BMID%3A1%3BLID%3A1%7D/Carbothane_134_HG_PDS.pdf> (2023): 1-4.

Carmell et al., "Germline transmission of RNAi in mice." Nature structural biology 10.2 (2003): 91-92.

Carmell et al., "RNase III enzymes and the initiation of gene silencing." Nature structural & molecular biology 11.3 (2004): 214-218.

Carmell et al., "The Argonaute family: tentacles that reach into RNAi, developmental control, stem cell maintenance, and tumorigenesis." Genes & development 16.21 (2002): 2733-2742.

Carmichael G., "Antisense starts making more sense." Nature biotechnology 21.4 (2003): 371-372.

Carrington et al., "Role of microRNAs in plant and animal development." Science 301.5631 (2003): 336-338.

Carter et al., "A computational approach to identify genes for functional RNAs in genomic sequences." Nucleic acids research 29.19 (2001): 3928-3938.

Carthew R., "Making and breaking with nucleases and small RNAs." Nature Structural & Molecular Biology 10.10 (2003): 776-777.

Casaca-Carreira et al., "Transependymal cerebrospinal fluid flow: opportunity for drug delivery." Molecular neurobiology 55.4 (2018): 2780-2788.

Casset et al., "A peptide mimetic of an anti-CD4 monoclonal antibody by rational design." Biochemical and biophysical research communications 307.1 (2003): 198-205.

Catalanotto et al., "Involvement of small RNAs and role of the qde genes in the gene silencing pathway in Neurospora." Genes & development 16.7 (2002): 790-795.

Caudy et al., "A micrococcal nuclease homologue in RNAi effector complexes." Nature 425.6956 (2003): 411-414.

Gaudilliere et al., "RNA interference reveals a requirement for myocyte enhancer factor 2A in activity-dependent neuronal survival." Journal of Biological Chemistry 277.48 (2002): 46442-46446.

Ge et al., "Inhibition of influenza virus production in virus-infected mice by RNA interference." Proceedings of the National Academy of Sciences 101.23 (2004): 8676-8681.

Gebauer et al., "Molecular mechanisms of translational control." Nature reviews Molecular cell biology 5.10 (2004): 827-835.

Gernert et al., "Bypassing the blood-brain barrier: direct intracranial drug delivery in epilepsies." Pharmaceutics 12.12 (2020): 1-39.

Gershon D., "Microarrays go mainstream." Nature Methods 1.3 (2004): 263-270.

Geuze et al., "Reduced GABAA benzodiazepine receptor binding in veterans with post-traumatic stress disorder." Molecular psychiatry 13.1 (2008): 74-83.

Ghosal et al., "Prefrontal cortex GABAergic deficits and circuit dysfunction in the pathophysiology and treatment of chronic stress and depression." Current opinion in behavioral sciences 14 (2017): 1-8.

Ghosh et al., "Functional connectivity from the amygdala to the hippocampus grows stronger after stress." Journal of Neuroscience 33.17 (2013): 7234-7244.

Gibbs W., "The unseen genome: beyond DNA." Scientific American 289.6 (2003): 106-113.

Gibbs W., "The unseen genome: gems among the junk." Scientific American 289.5 (2003): 46-53.

Giordano et al., "RNAi triggered by symmetrically transcribed transgenes in Drosophila melanogaster." Genetics 160.2 (2002): 637-648.

(56)            References Cited

OTHER PUBLICATIONS

Giraldez et al., "MicroRNAs regulate brain morphogenesis in zebrafish." Science 308.5723 (2005): 833-838.

Gitlin et al., "Poliovirus escape from RNA interference: short interfering RNA-target recognition and implications for therapeutic approaches." Journal of virology 79.2 (2005): 1027-1035.

Golden et al., "Short Integuments1/Suspensor1/Carpel Factory, a Dicer homolog, is a maternal effect gene required for embryo development in *Arabidopsis*." Plant Physiology 130.2 (2002): 808-822.

Gooch et al., "Recognition of Duplex RNA by Helix-Threading Peptides." Journal of the American Chemical Society 126.34 (2004): 10603-10610.

Gottesman S., "Stealth regulation: biological circuits with small RNA switches." Genes & development 16.22 (2002): 2829-2842.

Grad et al., "Computational and experimental identification of C. elegans microRNAs." Molecular cell 11.5 (2003): 1253-1263.

Gradus et al., "Associations between stress disorders and cardiovascular disease events in the Danish population." BMJ open 5.12 (2015): 1-7.

Gradus et al., "Posttraumatic stress disorder and completed suicide." American journal of epidemiology 171.6 (2010): 721-727.

Gradus J., "Prevalence and prognosis of stress disorders: a review of the epidemiologic literature." Clinical epidemiology (2017): 251-260.

Gras et al., "BCMAp: an integral membrane protein in the Golgi apparatus of human mature B lymphocytes." International immunology 7.7 (1995): 1093-1106.

Gregory et al., "MicroRNA biogenesis and cancer." Cancer research 65.9 (2005): 3509-3512.

Gregory et al., "The Microprocessor complex mediates the genesis of microRNAs." Nature 432.7014 (2004): 235-240.

Grey et al., "Cognitive restructuring within reliving: A treatment for peritraumatic emotional "hotspots" in posttraumatic stress disorder." Behavioural and cognitive psychotherapy 30.1 (2002): 37-56.

Griffiths-Jones S., "The microRNA registry." Nucleic acids research 32 (2004): D109-D111.

Grisaru et al., "Structural roles of acetylcholinesterase variants in biology and pathology." European Journal of Biochemistry 264.3 (1999): 672-686.

Grishok et al., "Genes and mechanisms related to RNA interference regulate expression of the small temporal RNAs that control C. elegans developmental timing." Cell 106.1 (2001): 23-34.

Grosshans et al., "Micro-RNAs: small is plentiful." The Journal of cell biology 156.1 (2002): 17-22.

Großhans et al., "The temporal patterning microRNA let-7 regulates several transcription factors at the larval to adult transition in C. elegans." Developmental cell 8.3 (2005): 321-330.

Guarguaglini et al., "The forkhead-associated domain protein Cep170 interacts with Polo-like kinase 1 and serves as a marker for mature centrioles." Molecular biology of the cell 16.3 (2005): 1095-1107.

Gupta et al., "Directly labeled mRNA produces highly precise and unbiased differential gene expression data." Nucleic acids research 31.4 (2003): 1-6.

Gustafson et al., "ASRP: the Arabidopsis small RNA project database." Nucleic acids research 33 (2005): D637-D640.

Hake S., "MicroRNAs: a role in plant development." Current Biology 13.21 (2003): R851-R852.

Hall J., "Unravelling the general properties of siRNAs: strength in numbers and lessons from the past." Nature Reviews Genetics 5.7 (2004): 552-557.

Hamann et al., "Amygdala activity related to enhanced memory for pleasant and aversive stimuli." Nature neuroscience 2.3 (1999): 289-293.

Hamilton et al., "Two classes of short interfering RNA in RNA silencing." The EMBO journal 21.17 (2002): 4671-4679.

Hammond et al., "An RNA-directed nuclease mediates post-transcriptional gene silencing in *Drosophila* cells." Nature 404.6775 (2000): 293-296.

Hammond et al., "Argonaute2, a link between genetic and biochemical analyses of RNAi." Science 293.5532 (2001): 1146-1150.

Han et al., "Relationship between small antisense RNAs and aberrant RNAs associated with sense transgene mediated gene silencing in tomato." The Plant Journal 29.4 (2002): 509-519.

Han et al., "The Arabidopsis double-stranded RNA-binding protein HYL1 plays a role in microRNA-mediated gene regulation." Proceedings of the National Academy of Sciences 101.4 (2004): 1093-1098.

Han et al., "The Drosha-DGCR8 complex in primary microRNA processing." Genes & development 18.24 (2004): 3016-3027.

Hannon G., "RNA interference." nature 418.6894 (2002): 244-251.

Hansen et al., "Global effects on gene expression in fission yeast by silencing and RNA interference machineries." Molecular and cellular biology 25.2 (2005): 590-601.

Hardy J., "Toward Alzheimer therapies based on genetic knowledge." Annu. Rev. Med. 55.1 (2004): 15-25.

Harlow et al., "Using Antibodies: A Laboratory Manual." Cold Spring Harbor Laboratory (1998) 1-3.

Harrell E., "Neuromarketing: What you need to know." Harvard Business Review 97.4 (2019): 64-70.

Harris et al., "Effects of benzodiazepine microinjection into the amygdala or periaqueductal gray on the expression of conditioned fear and hypoalgesia in rats." Behavioral neuroscience 109.2 (1995): 295-304.

Hartig et al., "Sequence-specific detection of MicroRNAs by signal-amplifying ribozymes." Journal of the American Chemical Society 126.3 (2004): 722-723.

Hatzoglou et al., "TNF receptor family member Bcma (B cell maturation) associates with TNF receptor-associated factor (TRAF) 1, TRAF2, and TRAF3 and activates NF-KB, elk-1, c-Jun N-terminal kinase, and p38 mitogen-activated protein kinase." The Journal of Immunology 165.3 (2000): 1322-1330.

Hayase T., "Putative epigenetic involvement of the endocannabinoid system in anxiety-and depression-related behaviors caused by nicotine as a stressor." PLoS One 11.7 (2016): 1-21.

Shi, Y. "Mammalian RNAi for the masses." Trends in Genetics 19.1 (2003): 9-12.

Shim et al., "Machine-learning-based classification between post-traumatic stress disorder and major depressive disorder using P300 features." NeuroImage: Clinical 24 (2019): 1-8.

Shin et al., "Amygdala, medial prefrontal cortex, and hippocampal function in PTSD." Annals of the New York Academy of Sciences 1071.1 (2006): 67-79.

Shin et al., "Hippocampal function in posttraumatic stress disorder." Hippocampus 14.3 (2004): 292-300.

Shin et al., "Regional cerebral blood flow in the amygdala and medial prefrontalcortex during traumatic imagery in male and female vietnam veterans with ptsd." Archives of general psychiatry 61.2 (2004): 168-176.

Shin et al., "Resting metabolic activity in the cingulate cortex and vulnerability to posttraumatic stress disorder." Archives of general psychiatry 66.10 (2009): 1099-1107.

Shin et al., "The neurocircuitry of fear, stress, and anxiety disorders." Neuropsychopharmacology 35.1 (2010): 169-191.

Shin et al., "Transcriptional and post-transcriptional regulation of the PKCd gene by etoposide in L1210 murine leukemia cells: implication of PKCd autoregulation." Journal of molecular biology 340.4 (2004): 681-693.

Shiner et al., "A retrospective comparative effectiveness study of medications for posttraumatic stress disorder in routine practice." The Journal of clinical psychiatry 79.5 (2018): 1-20.

Shiner et al., "Anticonvulsant medication use in veterans with posttraumatic stress disorder." The Journal of clinical psychiatry 78.5 (2017): e545-e552.

Shivakumar et al., "Targeting B-lymphocyte stimulator/B-cell activating factor and a proliferation-inducing ligand in hematologic malignancies." Clinical Lymphoma and Myeloma 7.2 (2006): 106-108.

Sigova et al., "A single Argonaute protein mediates both transcriptional and posttranscriptional silencing in *Schizosaccharomyces pombe*." Genes & development 18.19 (2004): 2359-2367.

(56) References Cited

OTHER PUBLICATIONS

Sijen et al., "Post-transcriptional gene-silencing: RNAs on the attack or on the defense." Bioessays 22.6 (2000): 520-531.

Silhavy et al., "A viral protein suppresses RNA silencing and binds silencing-generated, 21-to 25-nucleotide double-stranded RNAs." The EMBO journal (2002): 1-11.

Silvestri et al., "Rotavirus replication: plus-sense templates for double-stranded RNA synthesis are made in viroplasms." Journal of virology 78.14 (2004): 7763-7774.

Simmonds et al., "Detection of genome-scale ordered RNA structure (GORS) in genomes of positive-stranded RNA viruses: Implications for virus evolution and host persistence." Rna 10.9 (2004): 1337-1351.

Sims et al., "Identification and characterization of circulating human transitional B cells." Blood 105.11 (2005): 4390-4398.

Siolas et al., "Synthetic shRNAs as potent RNAi triggers." Nature biotechnology 23.2 (2005): 227-231.

Slack et al., "The lin-41 RBCC gene acts in the C. elegans heterochronic pathway between the let-7 regulatory RNA and the LIN-29 transcription factor." Molecular cell 5.4 (2000): 659-669.

Sledz et al., "Activation of the interferon system by short-interfering RNAs." Nature cell biology 5.9 (2003): 834-839.

Smale S., "The establishment and maintenance of lymphocyte identity through gene silencing." Nature immunology 4.7 (2003): 607-615.

Smalheiser et al., "A population-based statistical approach identifies parameters characteristic of human microRNA-mRNA interactions." BMC bioinformatics 5.1 (2004): 1-8.

Smalheiser, N. "EST analyses predict the existence of a population of chimeric microRNA precursor-mRNA transcripts expressed in normal human and mouse tissues." Genome biology 4.7 (2003): 1-3.

Smallridge R., "A small fortune." Nature Reviews Molecular Cell Biology 2.12 (2001): 867-867.

Smirnova et al., "Regulation of miRNA expression during neural cell specification." European Journal of Neuroscience 21.6 (2005): 1469-1477.

Smith et al., "Intrathecal drug delivery." Pain physician 11.2S (2008): S89-S104.

Smith et al., "The early detection of prostate carcinoma with prostate specific antigen: the Washington University experience." Cancer: Interdisciplinary International Journal of The American Cancer Society 80.9 (1997): 1852-1856.

Smith et al., "Total silencing by intron-spliced hairpin RNAs." Nature 407.6802 (2000): 319-320.

Soldan et al., "La Crosse virus nonstructural protein NSs counteracts the effects of short interfering RNA." Journal of virology 79.1 (2005): 234-244.

Song et al., "Crystal structure of Argonaute and its implications for RISC slicer activity." science 305.5689 (2004): 1434-1437.

Sontheimer et al., "Argonaute journeys into the heart of RISC." Science 305.5689 (2004): 1409-1410.

Sosin et al., "Trends in death associated with traumatic brain injury, 1979 through 1992: success and failure." Jama 273.22 (1995): 1778-1780.

Souret et al., "AtXRN4 degrades mRNA in Arabidopsis and its substrates include selected miRNA targets." Molecular cell 15.2 (2004): 173-183.

Soutschek et al., "Therapeutic silencing of an endogenous gene by systemic administration of modified siRNAs." Nature 432.7014 (2004): 173-178.

Spira et al., "Generation of mutant monoclonal antibodies." Methods of Hybridoma Formation. Totowa, NJ: Humana Press (1987): 379-397.

Spiridon et al., "A comparison of the in vitro and in vivo activities of IgG and F (ab') 2 fragments of a mixture of three monoclonal anti-Her-2 antibodies." Clinical Cancer Research 10.10 (2004): 3542-3551.

Spitzer et al., "Trauma, posttraumatic stress disorder, and physical illness: findings from the general population." Psychosomatic medicine 71.9 (2009): 1012-1017.

Stark et al., "Identification of *Drosophila* microRNA targets." PLoS biology 1.3 (2003): 397-409.

Staubli et al., "Facilitation of glutamate receptors enhances memory." Proceedings of the National Academy of Sciences 91.2 (1994): 777-781.

Steenkamp et al., "Psychotherapy for military-related PTSD: A review of randomized clinical trials." Jama 314.5 (2015): 489-500.

Stein et al., "Genetic programming by the proteolytic fragments of the amyloid precursor protein: somewhere between confusion and clarity." Reviews in the neurosciences 14.4 (2003): 317-342.

Stein et al., "Ketamine for PTSD: well, isn't that special." American Journal of Psychiatry 178.2 (2021): 116-118.

Stein et al., "Randomized, placebo-controlled trial of the angiotensin receptor antagonist losartan for posttraumatic stress disorder." Biological Psychiatry 90.7 (2021): 473-481.

Steinman et al., "Transcriptional analysis of targets in multiple sclerosis." Nature Reviews Immunology 3.6 (2003): 483-492.

Stevens et al., "Episodic memory after trauma exposure: Medial temporal lobe function is positively related to re-experiencing and inversely related to negative affect symptoms." NeuroImage: Clinical 17 (2018): 650-658.

Stevenson M., "Dissecting HIV-1 through RNA interference." Nature Reviews Immunology 3.11 (2003): 851-858.

Stix G., "Hitting the genetic off switch." Scientific American 291.4 (2004): 98-101.

Storz et al., "Controlling mRNA stability and translation with small, noncoding RNAs." Current opinion in microbiology 7.2 (2004): 140-144.

Stoutjesdijk et al., "hpRNA-mediated targeting of the *Arabidopsis* FAD2 gene gives highly efficient and stable silencing." Plant physiology 129.4 (2002): 1723-1731.

Straud et al., "Examining military population and trauma type as moderators of treatment outcome for first-line psychotherapies for PTSD: A meta-analysis." Journal of anxiety disorders 67 (2019): 1-26.

Written Opinion in PCT/US2021/041766, mailed May 30, 2022, 7 pages.

Written Opinion in PCT/US2021/041772, mailed May 30, 2022, 8 pages.

Written Opinion in PCT/US2022/054049, mailed Nov. 16, 2023, 9 pages.

Wrocklage et al., "Neuropsychological functioning in veterans with posttraumatic stress disorder: Associations with performance validity, comorbidities, and functional outcomes." Journal of the International Neuropsychological Society 22.4 (2016): 399-411.

Wu et al., "An electroencephalographic signature predicts antidepressant response in major depression." Nature biotechnology 38.4 (2020): 439-447.

Wu et al., "Humanization of a murine monoclonal antibody by simultaneous optimization of framework and CDR residues." Journal of Molecular Biology 294.1 (1999): 151-162.

Wu et al., "Inhibition of SARS-CoV replication by siRNA." Antiviral research 65.1 (2005): 45-48.

Wu et al., "Unsupervised feature learning via non-parametric instance discrimination." Proceedings of the IEEE conference on computer vision and pattern recognition (2018): 3733-3742.

Wuchty et al., "Complete suboptimal folding of RNA and the stability of secondary structures." Biopolymers: Original Research on Biomolecules 49.2 (1999): 145-165.

Xayaphoummine et al., "Prediction and statistics of pseudoknots in RNA structures using exactly clustered stochastic simulations." Proceedings of the National Academy of Sciences 100.26 (2003): 15310-15315.

Xiang et al., "Amine-modified random primers to label probes for DNA microarrays." nature biotechnology 20.7 (2002): 738-742.

Xiao et al., "A novel mechanism of checkpoint abrogation conferred by Chk1 downregulation." Oncogene 24.8 (2005): 1403-1411.

Xie et al., "Genetic and functional diversification of small RNA pathways in plants." PLoS biology 2.5 (2004): 642-652.

Xie et al., "Negative feedback regulation of Dicer-Like1 in *Arabidopsis* by microRNA-guided mRNA degradation." Current Biology 13.9 (2003): 784-789.

(56)     References Cited

OTHER PUBLICATIONS

Xie et al., "Systematic discovery of regulatory motifs in human promoters and 3' UTRs by comparison of several mammals." Nature 434.7031 (2005): 338-345.

Xu et al., "B-cell maturation protein, which binds the tumor necrosis factor family members BAFF and APRIL, is dispensable for humoral immune responses." Molecular and Cellular Biology 21.12 (2001): 4067-4074.

Xu et al., "MicroRNAs and the regulation of cell death." Trends in Genetics 20.12 (2004): 617-624.

Xu et al., "The Drosophila microRNA Mir-14 suppresses cell death and is required for normal fat metabolism." Current Biology 13.9 (2003): 790-795.

Yang et al., "Dicer is required for embryonic angiogenesis during mouse development." Journal of Biological Chemistry 280.10 (2005): 9330-9335.

Yang et al., "Evidence that processed small dsRNAs may mediate sequence-specific mRNA degradation during RNAi in *Drosophila* embryos." Current Biology 10.19 (2000): 1191-1200.

Yang et al., "Intracranial hemorrhage risk factors of deep brain stimulation for Parkinson's disease: a 2-year follow-up study." Journal of International Medical Research 48.5 (2020): 1-10.

Ye et al., "Recognition of small interfering RNA by a viral suppressor of RNA silencing." Nature 426.6968 (2003): 874-878.

Yee et al., "GABAA receptors containing the a5 subunit mediate the trace effect in aversive and appetitive conditioning and extinction of conditioned fear." European Journal of Neuroscience 20.7 (2004): 1928-1936.

Yeh et al., "A double-blind randomized controlled trial to study the efficacy of topiramate in a civilian sample of PTSD." CNS neuroscience & therapeutics 17.5 (2011): 305-310.

Yehuda et al., "Learning and memory in Holocaust survivors with posttraumatic stress disorder." Biological psychiatry 55.3 (2004): 291-295.

Yekta et al., "MicroRNA-directed cleavage of HOXB8 mRNA." Science 304.5670 (2004): 594-596.

Yelin et al., "Widespread occurrence of antisense transcription in the human genome." Nature biotechnology 21.4 (2003): 379-386.

Yi et al., "Exportin-5 mediates the nuclear export of pre-microRNAs and short hairpin RNAs." Genes & development 17.24 (2003): 3011-3016.

Yi et al., "Overexpression of exportin 5 enhances RNA interference mediated by short hairpin RNAs and microRNAs." Rna 11.2 (2005): 220-226.

Ying et al., "Intron-derived microRNAs—fine tuning of gene functions." Gene 342.1 (2004): 25-28.

Ying et al., "Intronic microRNAs." Biochemical and biophysical research communications 326.3 (2005): 515-520.

Yoo et al., "A systemic small RNA signaling system in plants." The Plant Cell 16.8 (2004): 1979-2000.

YouTube video entitled: "Biomarker Terminology: Speaking the Same Language," uploaded Jan. 27, 2017 by user "U. S. Food and Drug Administration," [retrieved on Jun. 24, 2020]. Retrieved from the Internet: <URL: https://www.youtube.com/watch?v=OXo5E0R7zBc>, 1 page.

Yu et al., "Methylation as a crucial step in plant microRNA biogenesis." Science 307.5711 (2005): 932-935.

Yuan et al., "Adaptive design for staggered-start clinical trial." The International Journal of Biostatistics 12.2 (2016): 1-17.

Yun et al., "Both ERK and Wnt/β-catenin pathways are involved in Wnt3a-induced proliferation." Journal of cell science 118.2 (2005): 313-322.

Zamore, P. "Ancient pathways programmed by small RNAs." Science 296.5571 (2002): 1265-1269.

Zamore, P. "Plant RNAi: How a Viral silencing suppressor inactivates siRNA." Current Biology 14.5 (2004): R198-R200.

Zamvil et al., "Diverse targets for intervention during inflammatory and neurodegenerative phases of multiple sclerosis." Neuron 38.5 (2003): 685-688.

Zanatta et al., "Valproic acid interactions with the NavMs voltage-gated sodium channel." Proceedings of the National Academy of Sciences 116.52 (2019): 26549-26554.

Zandvakili et al., "Use of machine learning in predicting clinical response to transcranial magnetic stimulation in comorbid post-traumatic stress disorder and major depression: a resting state electroencephalography study." Journal of affective disorders 252 (2019): 47-54.

Zeng et al., "Both natural and designed micro RNAs can inhibit the expression of cognate mRNAs when expressed in human cells." Molecular cell 9.6 (2002): 1327-1333.

Zeng et al., "MicroRNAs and small interfering RNAs can inhibit mRNA expression by similar mechanisms." Proceedings of the National Academy of Sciences 100.17 (2003): 9779-9784.

Zeng et al., "Recognition and cleavage of primary microRNA precursors by the nuclear processing enzyme Drosha." The EMBO journal 24.1 (2005): 138-148.

Zeng et al., "RNA interference in human cells is restricted to the cytoplasm." Rna 8.7 (2002): 855-860.

Zeng et al., "Sequence requirements for micro RNA processing and function in human cells." Rna 9.1 (2003): 112-123.

Zeng et al., "Structural requirements for pre-microRNA binding and nuclear export by Exportin 5." Nucleic acids research 32.16 (2004): 4776-4785.

Zerhouni et al., "Isolation of CD4-independent primary human immunodeficiency virus type 1 isolates that are syncytium inducing and acutely cytopathic for CD8+ lymphocytes." Journal of virology 78.3 (2004): 1243-1255.

Zhang et al., "BAFF supports human B cell differentiation in the lymphoid follicles through distinct receptors." International immunology 17.6 (2005): 779-788.

Zhang et al., "Fathoming fragile X in fruit flies." Trends in Genetics 21.1 (2005): 37-45.

Novak et al., "Expression of BLyS and its receptors in B-cell non-Hodgkin lymphoma: correlation with disease activity and patient outcome." Blood 104.8 (2004): 2247-2253.

Novina et al., "siRNA-directed inhibition of HIV-1 infection." Nature medicine 8.7 (2002): 681-686.

Novina et al., "The rnai revolution." Nature 430.6996 (2004): 161-164.

O'Connor et al., "BCMA is essential for the survival of long-lived bone marrow plasma cells." The Journal of experimental medicine 199.1 (2004): 91-98.

O'Loghlen et al., "Suppression of human Mnk1 by small interfering RNA increases the eukaryotic initiation factor 4F activity in HEK293T cells." FEBS letters 578.1-2 (2004): 31-35.

O'Toole et al., "Stability of 3' double nucleotide overhangs that model the 3' ends of siRNA." Rna 11.4 (2005): 512-516.

Ogita et al., "Application of RNAi to confirm theobromine as the major intermediate for caffeine biosynthesis in coffee plants with potential for construction of decaffeinated varieties." Plant molecular biology 54.6 (2004): 931-941.

Ohler et al., "Patterns of flanking sequence conservation and a characteristic upstream motif for microRNA gene identification." Rna 10.9 (2004): 1309-1322.

Ohno et al., "BACE1 deficiency rescues memory deficits and cholinergic dysfunction in a mouse model of Alzheimer's disease." Neuron 41.1 (2004): 27-33.

Okamura et al., "Distinct roles for Argonaute proteins in small RNA-directed RNA cleavage pathways." Genes & development 18.14 (2004): 1655-1666.

Okazaki et al., "FANTOM Consortium; RIKEN Genome Exploration Research Group Phase I & II Team. Analysis of the mouse transcriptome based on functional annotation of 60,770 full-length cDNAs." (2002): 563-573.

Olsen et al., "The lin-4 regulatory RNA controls developmental timing in Caenorhabditis elegans by blocking LIN-14 protein synthesis after the initiation of translation." Developmental biology 216.2 (1999): 671-680.

Omoto et al., "HIV-1 nef suppression by virally encoded microRNA." Retrovirology 1.1 (2004): 1-12.

(56)            References Cited

OTHER PUBLICATIONS

Omoto et al., "Regulation of human immunodeficiency virus 1 transcription by nef microRNA." Journal of General Virology 86.3 (2005): 751-755.
Onishi et al., "Withdrawn: Molecular evolution of a microRNA cluster in the PWS/AS region among mammals." (2005): 1-1.
Opdyke et al., "GadY, a small-RNA regulator of acid response genes in *Escherichia coli*." Journal of bacteriology 186.20 (2004): 6698-6705.
Orban et al., "Decay of mRNAs targeted by RISC requires XRN1, the Ski complex, and the exosome." Rna 11.4 (2005): 459-469.
Ostberg et al., "The etiological agent of Lyme disease, Borrelia burgdorferi, appears to contain only a few small RNA molecules." Journal of bacteriology 186.24 (2004): 8472-8477.
Osuch et al., "Regional cerebral blood flow correlated with flash-back intensity in patients with posttraumatic stress disorder." Biological psychiatry 50.4 (2001): 246-253.
Ota et al., "Complete sequencing and characterization of 21,243 full-length human cDNAs." Nature genetics 36.1 (2004): 40-45.
Ota et al., "Identification and characterization of a novel gene, C13orf25, as a target for 13q31-q32 amplification in malignant lymphoma." Cancer research 64.9 (2004): 3087-3095.
Otte et al., "Valproate monotherapy in the treatment of civilian patients with non-combat-related posttraumatic stress disorder: an open-label study." Journal of clinical psychopharmacology 24.1 (2004): 106-108.
Overhoff et al., "Local RNA target structure influences siRNA efficacy: a systematic global analysis." Journal of molecular biology 348.4 (2005): 871-881.
Paddison et al., "Short hairpin RNAs (shRNAs) induce sequence-specific silencing in mammalian cells." Genes & development 16.8 (2002): 948-958.
Paddison et al., "Stable suppression of gene expression by RNAi in mammalian cells." Proceedings of the National Academy of Sciences 99.3 (2002): 1443-1448.
Padlan et al., "Structure of an antibody-antigen complex: crystal structure of the HyHEL-10 Fab-lysozyme complex." Proceedings of the National Academy of Sciences 86.15 (1989): 5938-5942.
Palatnik et al., "Control of leaf morphogenesis by microRNAs." Nature 425.6955 (2003): 257-263.
Panagioti et al., "Post-traumatic stress disorder and suicidal behavior: A narrative review." Clinical psychology review 29.6 (2009): 471-482.
Pang et al., "RNAdb—a comprehensive mammalian noncoding RNA database." Nucleic acids research 33.suppl_1 (2005): D125-D130.
Parizotto et al., "In vivo investigation of the transcription, processing, endonucleolytic activity, and functional relevance of the spatial distribution of a plant miRNA." Genes & development 18.18 (2004): 2237-2242.
Park et al., "Carpel Factory, a Dicer homolog, and HEN1, a novel protein, act in microRNA metabolism in *Arabidopsis thaliana*." Current biology 12.17 (2002): 1484-1495.
Parker et al., "Sequence and transcription of Raji Epstein-Barr virus DNA spanning the B95-8 deletion region." Virology 179.1 (1990): 339-346.
Pasquinelli et al., "Conservation of the sequence and temporal expression of let-7 heterochronic regulatory RNA." Nature 408. 6808 (2000): 86-89.
Pasquinelli et al., "Control of developmental timing by microRNAs and their targets." Annual review of cell and developmental biology 18.1 (2002): 495-513.
Pasquinelli et al., "MicroRNAs: a developing story." Current opinion in genetics & development 15.2 (2005): 200-205.
Pasquinelli, A. "MicroRNAs: deviants no longer." Trends in Genetics 18.4 (2002): 171-173.
Paykel, E. "Achieving gains beyond response." Acta Psychiatrica Scandinavica 106 (2002): 12-17.
Pearson et al., "Creation of "humanized" mice to study human immunity." Current protocols in immunology 81.1 (2008): 15-21.

Perumal et al., "Inhibitory circuits in the basolateral amygdala in aversive learning and memory." Frontiers in Neural Circuits 15 (2021): 633235.
Pfeffer et al., "Identification of microRNAs of the herpesvirus family." Nature methods 2.4 (2005): 269-276.
Pfeffer et al., "Identification of virus-encoded microRNAs." Science 304.5671 (2004): 734-736.
Piccin et al., "Efficient and heritable functional knock-out of an adult phenotype in Drosophila using a GAL4-driven hairpin RNA incorporating a heterologous spacer." Nucleic acids research 29.12 (2001): 1-5.
Pillai et al., "Tethering of human Ago proteins to mRNA mimics the miRNA-mediated repression of protein synthesis." Rna 10.10 (2004): 1518-1525.
Pissiota et al., "Neurofunctional correlates of posttraumatic stress disorder: a PET symptom provocation study." European archives of psychiatry and clinical neuroscience 252.2 (2002): 68-75.
Pitt et al., "P granules in the germ cells of Caenorhabditis elegans adults are associated with clusters of nuclear pores and contain RNA." Developmental biology 219.2 (2000): 315-333.
Pocivavsek et al., "Fluctuations in endogenous kynurenic acid control hippocampal glutamate and memory." Neuropsychopharmacology 36.11 (2011): 2357-2367.
Pomerantz et al., "Two pathways to NF-kB." Molecular cell 10.4 (2002): 693-695.
Pomerantz R., "RNA interference meets HIV-1: will silence be golden." Nature Medicine 8.7 (2002): 659-660.
Ponniah et al., "Empirically supported psychological treatments for adult acute stress disorder and posttraumatic stress disorder: a review." Depression and anxiety 26.12 (2009): 1086-1109.
Pooggin et al., "Fighting geminiviruses by RNAi and vice versa." Plant molecular biology 55.2 (2004): 149-152.
Abbott A. L., "Heterochronic genes." Current Biology 13.21 (2003): R824-R825.
Abrahante et al., "The Caenorhabditis elegans hunchback-like gene lin-57/hbl-1 controls developmental time and is regulated by microRNAs." Developmental cell 4.5 (2003): 625-637.
Abrams D., "Feasibility of Delivery of Anti-Epilepsy Medications into the Cerebrospinal Fluid (10802)." Neuromodulation 19.3 (2015): e107.
Achard et al., "Modulation of floral development by a gibberellin-regulated microRNA." Development 131.14 (2004): 3357-3365.
Adai et al., "Computational prediction of miRNAs in *Arabidopsis thaliana*." Genome research 15.1 (2005): 78-91.
Adamou et al., "Valproate in the treatment of PTSD: systematic review and meta analysis." Current medical research and opinion 23.6 (2007): 1285-1291.
Agrawal et al., "Role of Toll-like receptors in antisense and siRNA [corrected]." Nature biotechnology 22.12 (2004): 1533-1537.
Akaneya et al., "RNAi-induced gene silencing by local electroporation in targeting brain region." Journal of neurophysiology 93.1 (2005): 594-602.
Albott et al., "Efficacy, safety, and durability of repeated ketamine infusions for comorbid posttraumatic stress disorder and treatment-resistant depression." The Journal of clinical psychiatry 79.3 (2018): 17462.
Albright et al., "Intraventricular baclofen for dystonia: techniques and outcomes." Journal of Neurosurgery: Pediatrics 3.1 (2009): 11-14.
Albright L., "Technique for insertion of intraventricular baclofen catheters." Journal of Neurosurgery: Pediatrics 8.4 (2011): 394-395.
Alibu et al., "A doubly inducible system for RNA interference and rapid RNAi plasmid construction in Trypanosoma brucei." Molecular and biochemical parasitology 139.1 (2005): 75-82.
Allawi et al., "Quantitation of microRNAs using a modified Invader assay." Rna 10.7 (2004): 1153-1161.
Allen et al., "Evolution of microRNA genes by inverted duplication of target gene sequences in *Arabidopsis thaliana*." Nature genetics 36.12 (2004): 1282-1290.
Allinson et al., "ADAMs family members as amyloid precursor protein a-secretases." Journal of neuroscience research 74.3 (2003): 342-352.

(56) References Cited

OTHER PUBLICATIONS

Allshire R., "RNAi and heterochromatin—a hushed-up affair." Science 297.5588 (2002): 1818-1819.

Alonso et al., "Days out of role due to common physical and mental conditions: results from the WHO World Mental Health surveys." Molecular psychiatry 16.12 (2011): 1234-1246.

Alsford et al., "Multiplex analysis of RNA interference defects in Trypanosoma brucei." Molecular and biochemical parasitology 139.1 (2005): 1-8.

Altuvia et al., "Clustering and conservation patterns of human microRNAs." Nucleic acids research 33.8 (2005): 2697-2706.

Altuvia S., "Regulatory small RNAs: the key to coordinating global regulatory circuits." Journal of Bacteriology 186.20 (2004): 6679-6680.

Alzoubi et al., "Pentoxifylline prevents post-traumatic stress disorder induced memory impairment." Brain research bulletin 139 (2018): 263-268.

Alzoubi et al., "Prevention of memory impairment induced by post-traumatic stress disorder by cerebrolysin." Psychiatry Research 270 (2018): 430-437.

Ambinder et al., "Epstein-Barr virus genome B95-8." XP002500226. Retrieved from EBI Database accession No. ADN12161 (2004).

Ambros V., "A uniform system for microRNA annotation." Rna 9.3 (2003): 277-279.

Ambros V., "MicroRNA pathways in flies and worms: growth, death, fat, stress, and timing." Cell 113.6 (2003): 673-676.

Ambros V., "MicroRNAs and other tiny endogenous RNAs in C. elegans." Current Biology 13.10 (2003): 807-818.

Ambros V., "microRNAs: tiny regulators with great potential." Cell 107.7 (2001): 823-826.

Ambros V., "The functions of animal microRNAs." Nature 431. 7006 (2004): 350-355.

Anandalakshmi et al., "A calmodulin-related protein that suppresses posttranscriptional gene silencing in plants." Science 290.5489 (2000): 142-144.

Anonymous. "Whither RNAi" Nat Cell Biol 5 (2003): 489-490.

Antonarakis et al., "Chromosome 21 and down syndrome: from genomics to pathophysiology." Nature reviews genetics 5.10 (2004): 725-738.

Aoun et al., "Impact of traumatic brain injury on sleep: an overview." Nature and science of sleep (2019): 131-140.

Arai et al., "Establishment of stable hFis1 knockdown cells with an siRNA expression vector." Journal of biochemistry 136.4 (2004): 421-425.

Aravin et al., "Dissection of a natural RNA silencing process in the Drosophila melanogaster germ line." Molecular and cellular biology 24.15 (2004): 6742-6750.

Aravin et al., "The small RNA profile during Drosophila melanogaster development." Developmental cell 5.2 (2003): 337-350.

Arditte Hall et al., "Plasma gamma-aminobutyric acid (GABA) levels and posttraumatic stress disorder symptoms in trauma-exposed women: a preliminary report." Psychopharmacology 238.6 (2021): 1541-1552.

Argaman et al., "Novel small RNA-encoding genes in the intergenic regions of Escherichia coli." Current Biology 11.12 (2001): 941-950.

Arias et al., "RNA silencing of rotavirus gene expression." Virus research 102.1 (2004): 43-51.

Ashrafi et al., "Genome-wide RNAi analysis of Caenorhabditis elegans fat regulatory genes." Nature 421.6920 (2003): 268-272.

Atkinson A., "Intracerebroventricular drug administration." Translational and Clinical Pharmacology 25.3 (2017): 117-124.

Atwoli et al., "Epidemiology of posttraumatic stress disorder: prevalence, correlates and consequences." Current opinion in psychiatry 28.4 (2015): 307-311.

Augustinsson et al., "Intracerebroventricular administration of GM1 ganglioside to presenile Alzheimer patients." Dementia and geriatric cognitive disorders 8.1 (1997): 26-33.

Aukerman et al., "Regulation of flowering time and floral organ identity by a microRNA and its APETALA2-like target genes." The Plant Cell 15.11 (2003): 2730-2741.

Averill et al., "Glutamate dysregulation and glutamatergic therapeutics for PTSD: Evidence from human studies." Neuroscience letters 649 (2017): 147-155.

Avery et al., "BAFF selectively enhances the survival of plasmablasts generated from human memory B cells." The Journal of clinical investigation 112.2 (2003): 286-297.

Ayash-Rashkovsky et al., "Generation of Th1 immune responses to inactivated, gp120-depleted HIV-1 in mice with a dominant Th2 biased immune profile via imunostimulatory oligonucleotides—relevance to AIDS vaccines in developing countries." Vaccine 20.21-22 (2002): 2684-2692.

Baba et al., "Solution structure of an RNA stem-loop derived from the 3' conserved region of eel LINE UnaL2." Rna 10.9 (2004): 1380-1387.

Babak et al., "Probing microRNAs with microarrays: tissue specificity and functional inference." Rna 10.11 (2004): 1813-1819.

Bagasra et al., "RNA interference: the molecular immune system." Journal of molecular histology 35.6 (2004): 545-553.

Bahramian et al., "GENE impedance: a natural process for control of gene expression and the origin of RNA interference." Journal of theoretical biology 233.3 (2005): 301-314.

Vaiva et al., "Low posttrauma GABA plasma levels as a predictive factor in the development of acute posttraumatic stress disorder." Biological psychiatry 55.3 (2004): 250-254.

Vajdos et al., "Comprehensive functional maps of the antigen-binding site of an anti-ErbB2 antibody obtained with shotgun scanning mutagenesis." Journal of molecular biology 320.2 (2002): 415-428.

Valoczi et al., "Sensitive and specific detection of microRNAs by northern blot analysis using LNA-modified oligonucleotide probes." Nucleic acids research 32.22 (2004): e175-e175.

Van Hilten et al., "Intrathecal baclofen for the treatment of dystonia in patients with reflex sympathetic dystrophy." New England Journal of Medicine 343.9 (2000): 625-630.

Vance et al., "RNA silencing in plants—defense and counterdefense." science 292.5525 (2001): 2277-2280.

Varker et al., "Efficacy of psychoactive drugs for the treatment of posttraumatic stress disorder: a systematic review of MDMA, ketamine, LSD and psilocybin." Journal of Psychoactive Drugs 53.1 (2021): 85-95.

Vaucheret et al., "Post-transcriptional gene silencing in plants." Journal of cell science 114.17 (2001): 3083-3091.

Vaucheret et al., "The action of ARGONAUTE1 in the miRNA pathway and its regulation by the miRNA pathway are crucial for plant development." Genes & development 18.10 (2004): 1187-1197.

Vaucheret et al., "Transcriptional gene silencing in plants: targets, inducers and regulators." Trends in Genetics 17.1 (2001): 29-35.

Vella et al., "Architecture of a validated microRNA: target interaction." Chemistry & biology 11.12 (2004): 1619-1623.

Vella et al., "The C. elegans microRNA let-7 binds to imperfect let-7 complementary sites from the lin-41 3' UTR." Genes & development 18.2 (2004): 132-137.

Verbitsky et al., "Rodent models of post-traumatic stress disorder: behavioral assessment." Translational psychiatry 10.1 (2020): 1-28.

Verma et al., "Modified oligonucleotides: synthesis and strategy for users." Annual review of biochemistry 67.1 (1998): 99-134.

Vermeulen et al., "The contributions of dsRNA structure to Dicer specificity and efficiency." Rna 11.5 (2005): 674-682.

Villareal et al., "Efficacy of quetiapine monotherapy in post-traumatic stress disorder: a randomized, placebo-controlled trial." American Journal of Psychiatry 173.12 (2016): 1205-1212.

Villareal et al., "Reduced hippocampal volume and total white matter volume in posttraumatic stress disorder." Biological psychiatry 52.2 (2002): 119-125.

Voinnet et al., "A viral movement protein prevents spread of the gene silencing signal in Nicotiana benthamiana." Cell 103.1 (2000): 157-167.

(56)          References Cited

OTHER PUBLICATIONS

Voinnet, O. "Induction and suppression of RNA silencing: insights from viral infections." Nature Reviews Genetics 6.3 (2005): 206-220.

Voinnet, O. "RNA silencing: small RNAs as ubiquitous regulators of gene expression." Current opinion in plant biology 5.5 (2002): 444-451.

Volpe et al., "Regulation of heterochromatic silencing and histone H3 lysine-9 methylation by RNAi." Science 297.5588 (2002): 1833-1837.

Vuillemenot et al., "Nonclinical evaluation of CNS-administered TPP1 enzyme replacement in canine CLN2 neuronal ceroid lipofuscinosis." Molecular genetics and metabolism 114.2 (2015): 281-293.

Walters et al., "RNAi-induced down-regulation of FLT3 expression in AML cell lines increases sensitivity to MLN518." Blood 105.7 (2005): 2952-2954.

Walters, J. "The relationship between post traumatic stress disorder (PTSD) symptoms and career outcomes of army enlisted servicemembers." The Pardee RAND Graduate School (2014): 1-189.

Wang et al., "An attempt to identify reproducible high-density EEG markers of PTSD during sleep." Sleep 43.1 (2020): 1-12.

Wang et al., "Identification of 20 microRNAs from *Oryza sativa*." Nucleic Acids Research 32.5 (2004): 1688-1695.

Wang et al., "Inter-channel phase differences during sleep spindles are altered in Veterans with PTSD." NeuroImage: Clinical 28 (2020): 102390.

Wang et al., "Prediction and identification of *Arabidopsis thaliana* microRNAs and their mRNA targets." Genome biology 5.9 (2004): 1-15.

Wang et al., "Tumor necrosis factor a-dependent drug resistance to purine and pyrimidine analogues in human colon tumor cells mediated through IKK." Journal of Biological Chemistry 280.9 (2005): 7634-7644.

Wang et al., "Viral discovery and sequence recovery using DNA microarrays." PLoS biology 1.2 (2003): 257-260.

Watanabe et al., "Stage-specific expression of microRNAs during Xenopus development." FEBS letters 579.2 (2005): 318-324.

Waterhouse et al., "Virus resistance and gene silencing in plants can be induced by simultaneous expression of sense and antisense RNA." Proceedings of the National Academy of Sciences 95.23 (1998): 13959-13964.

Weathers et al., "The Clinician-Administered PTSD Scale for DSM-5 (CAPS-5): Development and initial psychometric evaluation in military veterans." Psychological assessment 30.3 (2018): 383-395.

Weber et al., "Quorum-sensing-based toolbox for regulatable transgene and siRNA expression in mammalian cells." Biotechnology progress 21.1 (2005): 178-185.

Weber, M. "New human and mouse microRNA genes found by homology search." The FEBS journal 272.1 (2005): 59-73.

Wei et al., "TTK/hMps1 participates in the regulation of DNA damage checkpoint response by phosphorylating CHK2 on threonine 68." Journal of Biological Chemistry 280.9 (2005): 7748-7757.

Wen et al., "Deep convolution neural network and autoencoders-based unsupervised feature learning of EEG signals." IEEE Access 6 (2018): 25399-25410.

Wesemann et al., "Clinical accuracy and safety using the SynchroMed II intrathecal drug infusion pump." Regional Anesthesia & Pain Medicine 39.4 (2014): 341-346.

Wesley et al., "Construct design for efficient, effective and high-throughput gene silencing in plants." The Plant Journal 27.6 (2001): 581-590.

Westhof et al., "From RNAi to epigenomes: how RNA rules the world." Chembiochem 6.2 (2005): 441-443.

White et al., "Antibody-targeted immunotherapy for treatment of malignancy." Annual review of medicine 52.1 (2001): 125-145.

Wideman et al., "Involvement of classical neurotransmitter systems in memory reconsolidation: Focus on destabilization." Neurobiology of learning and memory 156 (2018): 68-79.

Wienholds et al., "The microRNA-producing enzyme Dicer1 is essential for zebrafish development." Nature genetics 35.3 (2003): 217-218.

Wightman et al., "Posttranscriptional regulation of the heterochronic gene lin-14 by lin-4 mediates temporal pattern formation in C. elegans." Cell 75.5 (1993): 855-862.

Wilson et al., "RNA interference blocks gene expression and RNA synthesis from hepatitis C replicons propagated in human liver cells." Proceedings of the National Academy of Sciences 100.5 (2003): 2783-2788.

Winkler et al., "Control of gene expression by a natural metabolite-responsive ribozyme." Nature 428.6980 (2004): 281-286.

Wiznerowicz et al., "Conditional suppression of cellular genes: lentivirus vector-mediated drug-inducible RNA interference." Journal of virology 77.16 (2003): 8957-8961.

Wong et al., "Computationally efficient epileptic seizure prediction based on extremely randomised trees." Proceedings of the Australasian Computer Science Week Multiconference (2020): 1-3.

Wood N., "Unravelling the molecular basis of viral suppression of PTGS." Trends in Plant Science 7.9 (2002): 384-385.

Woodman et al., "Panic disorder: treatment with valproate." The Journal of clinical psychiatry 55.4 (1994): 134-136.

Written Opinion in PCT/US2021/041763, mailed May 30, 2022, 9 pages.

Zhang et al., "Human Dicer preferentially cleaves dsRNAs at their termini without a requirement for ATP." The EMBO journal (2002): 5875-5885.

Zhang et al., "Inhibition of respiratory syncytial virus infection with intranasal siRNA nanoparticles targeting the viral NS1 gene." Nature medicine 11.1 (2005): 56-62.

Zhang, M. "Large-scale gene expression data analysis: a new challenge to computational biologists." Genome Research 9.8 (1999): 681-688.

Zhou et al., "Identification of NF-kB-regulated genes induced by TNFa utilizing expression profiling and RNA interference." Oncogene 22.13 (2003): 2054-2064.

Zoellner et al., "Doubly randomized preference trial of prolonged exposure versus sertraline for treatment of PTSD." American Journal of Psychiatry 176.4 (2019): 287-296.

Liu et al., "Emotion detection from EEG recordings." 12th International Conference on Natural Computation, Fuzzy Systems and Knowledge Discovery (2016): 1-6.

Vaiva et al., "Relationship between posttrauma GABA plasma levels and PTSD at 1-year follow-up." American Journal of Psychiatry 163.8 (2006): 1446-1448.

Ehret M., "Treatment of posttraumatic stress disorder: Focus on pharmacotherapy." Mental Health Clinician 9.6 (2019): 373-382.

Eichenbaum et al., "The hippocampus—what does it do." Behavioral and neural biology 57.1 (1992): 2-36.

Eichenbaum H., "The hippocampus and declarative memory: cognitive mechanisms and neural codes." Behavioural brain research 127.1-2 (2001): 199-207.

Einav et al., "shRNA-mediated RNA interference as a tool for genetic synthetic lethality screening in mouse embryo fibroblasts." FEBS letters 579.1 (2005): 199-202.

Eis et al., "Accumulation of miR-155 and BIC RNA in human B cell lymphomas." Proceedings of the National Academy of Sciences 102.10 (2005): 3627-3632.

Elbashir et al., "Analysis of gene function in somatic mammalian cells using small interfering RNAs." Methods 26.2 (2002): 199-213.

Elbashir et al., "Duplexes of 21-nucleotide RNAs mediate RNA interference in cultured mammalian cells." nature 411.6836 (2001): 494-498.

Elbashir et al., "Functional anatomy of siRNAs for mediating efficient RNAi in *Drosophila melanogaster* embryo lysate." The EMBO journal 20.23 (2001): 6877-6888.

Elbashir et al., "RNA interference is mediated by 21-and 22-nucleotide RNAs." Genes & development 15.2 (2001): 188-200.

(56) References Cited

OTHER PUBLICATIONS

Elmen et al., "Locked nucleic acid (LNA) mediated improvements in siRNA stability and functionality." Nucleic acids research 33.1 (2005): 439-447.

Emrick et al., "Different simultaneous sleep states in the hippocampus and neocortex." Sleep 39.12 (2016): 2201-2209.

Engdahl et al., "A two unit antisense RNA cassette test system for silencing of target genes." Nucleic acids research 25.16 (1997): 3218-3227.

Engstrom et al., "Promoter bashing, microRNAs, and Knox genes. New insights, regulators, and targets-of-regulation in the establishment of lateral organ polarity in Arabidopsis." Plant Physiology 135.2 (2004): 685-694.

Enright et al., "MicroRNA targets in *Drosophila*." Genome Biology 5.1 (2003): 1-27.

Epilepsy for Parents and Caregivers, Epilepsy.com, Retrieved from the Internet: <URL: https://www.epilepsy.com/living-epilepsy/epilepsy-and/professional-health-care-providers/about-epilepsy-seizures/idiopathic-4> (2024): 1-9.

Eriksdotter-Jonhagen et al., "Encapsulated cell biodelivery of nerve growth factor to the basal forebrain in patients with Alzheimer's disease." Dementia and geriatric cognitive disorders 33.1 (2012): 18-28.

Esau et al., "MicroRNA-143 regulates adipocyte differentiation." Journal of Biological Chemistry 279.50 (2004): 52361-52365.

Eshed et al., "MicroRNAs guide asymmetric DNA modifications guiding asymmetric organs." Developmental Cell 7.5 (2004): 629-630.

Esquela-Kerscher et al., "The age of high-throughput microRNA profiling." Nature Methods 1.2 (2004): 106-107.

Etkin et al., "Functional neuroimaging of anxiety: a meta-analysis of emotional processing in PTSD, social anxiety disorder, and specific phobia." American journal of Psychiatry 164.10 (2007): 1476-1488.

European Search Report for EP05774516.8, mailed Nov. 27, 2008, 5 pages.

European Search Report for EP16153513.3, mailed Jan. 17, 2020, 7 pages.

Fagard et al., "AGO1, QDE-2, and RDE-1 are related proteins required for post-transcriptional gene silencing in plants, quelling in fungi, and RNA interference in animals." Proceedings of the National Academy of Sciences 97.21 (2000): 11650-11654.

Famulok M., "Chemical biology: green fluorescent RNA." Nature 430 (2004): 976-977.

Fan et al., "RNA interference against a glioma-derived allele of EGFR induces blockade at G2M." Oncogene 24.5 (2005): 829-837.

Feder et al., "A randomized controlled trial of repeated ketamine administration for chronic posttraumatic stress disorder," American Journal of Psychiatry 178.2 (2021): 193-202.

Feder et al., "Efficacy of intravenous ketamine for treatment of chronic posttraumatic stress disorder: a randomized clinical trial." JAMA psychiatry 71.6 (2014): 681-688.

Fenoy et al., "Risks of common complications in deep brain stimulation surgery: management and avoidance." Journal of neurosurgery 120.1 (2014): 132-139.

Ferry et al., "The economic burden of PTSD in Northern Ireland." Journal of traumatic stress 28.3 (2015): 191-197.

Fesler F., "Valproate in combat-related posttraumatic stress disorder." The Journal of Clinical Psychiatry 52.9 (1991): 361-364.

Findley et al., "Maelstrom, a *Drosophila* spindle-class gene, encodes a protein that colocalizes with Vasa and RDE1/AGO1 homolog, Aubergine, in nuage." Development 130.5 (2003): 859-871.

Finnegan et al., "The small RNA world." Journal of cell science 116.23 (2003): 4689-4693.

Fire A., "RNA-triggered gene silencing." Trends in Genetics 15.9 (1999): 358-363.

Fire et al., "Potent and specific genetic interference by double-stranded RNA in Caenorhabditis elegans." nature 391.6669 (1998): 806-811.

Fisher et al., "Seizure diaries for clinical research and practice: limitations and future prospects." Epilepsy & Behavior 24.3 (2012): 304-310.

Fleischhack et al., "Pharmacokinetics following intraventricular administration of chemotherapy in patients with neoplastic meningitis." Clinical pharmacokinetics 44.1 (2005): 1-31.

Floriano-Sanchez et al., "Differential gene expression profile induced by valproic acid (VPA) in pediatric epileptic patients." Genes 9.7 (2018): 1-15.

Floyd et al., "Ancient microRNA target sequences in plants." Nature 428.6982 (2004): 485-486.

Foa et al., "Prolonged Exposure Therapy for PTSD: Emotional Processing of Traumatic Experiences." Therapist Guide, 2nd ed., Copyright page (2019) 1-2.

Forbes et al., "A guide to guidelines for the treatment of PTSD and related conditions." Journal of traumatic stress 23.5 (2010): 537-552.

Foreman et al., "Quantitative EEG for the detection of brain ischemia." Critical care 16.2 (2012): 1-9.

Forman-Hoffman et al., "Psychological and Pharmacological Treatments for Adults With Posttraumatic Stress Disorder: A Systematic Review Update," Agency for Healthcare Research and Quality (2018): 1-4.

Fortier et al., "Temperature-dependent gene silencing by an expressed inverted repeat in *Drosophila*." genesis 26.4 (2000): 240-244.

Fowler et al., "Intrathecal drug delivery in the era of nanomedicine." Advanced drug delivery reviews 165 (2020): 77-95.

Friedman et al., "Considering future pharmacotherapy for PTSD." Neuroscience letters 649 (2017): 181-185.

Friedrich et al., "RNA molecules as anti-cancer agents." Seminars in cancer biology 14.4 (2004): 223-230.

Froeyen et al., "RNA as a target for drug design, the example of Tat-TAR interaction." Current topics in medicinal chemistry 2.10 (2002): 1123-1145.

Gallinaro et al., "Structural Study of the 5' End of a Synthetic Premessenger RNA from Adenovirus: Evidence for a Long-range Exon-Intron Interaction." Journal of molecular biology 240.3 (1994): 205-225.

Galyam et al., "Complex host cell responses to antisense suppression of ACHE gene expression." Antisense and Nucleic Acid Drug Development 11.1 (2001): 51-57.

Garfinkel et al., "Impaired contextual modulation of memories in PTSD: an fMRI and psychophysiological study of extinction retention and fear renewal." Journal of Neuroscience 34.40 (2014): 13435-13443.

Baldino et al., "Sodium valproate enhancement of gamma-aminobutyric acid (GABA) inhibition: electrophysiological evidence for anticonvulsant activity." The Journal of Pharmacology and Experimental Therapeutics 217.2 (1981): 445-450.

Ball et al., "Signal quality of simultaneously recorded invasive and non-invasive EEG." Neuroimage 46.3 (2009): 708-716.

Ballantyne et al., "Comparative efficacy of epidural, subarachnoid, and intracerebroventricular opioids in patients with pain due to cancer (Cochrane Review)." Journal of the American College of Surgeons 200.6 (2005): 1-4.

Bandelow et al., "Biological markers for anxiety disorders, OCD and PTSD: A consensus statement. Part II: Neurochemistry, neurophysiology and neurocognition." The World Journal of Biological Psychiatry 18.3 (2017): 162-214.

Baner et al., "Parallel gene analysis with allele-specific padlock probes and tag microarrays." Nucleic Acids Research 31.17 (2003): e103-e103.

Banerjee et al., "Control of developmental timing by small temporal RNAs: a paradigm for RNA-mediated regulation of gene expression." Bioessays 24.2 (2002): 119-129.

Baniasadi et al., "Effect of pregabalin augmentation in treatment of patients with combat-related chronic posttraumatic stress disorder: a randomized controlled trial." Journal of Psychiatric Practice® 20.6 (2014): 419-427.

Bantounas et al., "RNA interference and the use of small interfering RNA to study gene function in mammalian systems." Journal of molecular endocrinology 33.3 (2004): 545-557.

(56) References Cited

OTHER PUBLICATIONS

Bao et al., "MicroRNA binding sites in *Arabidopsis* class III HD-ZIP mRNAs are required for methylation of the template chromosome." Developmental cell 7.5 (2004): 653-662.

Barad et al., "MicroRNA expression detected by oligonucleotide microarrays: system establishment and expression profiling in human tissues." Genome research 14.12 (2004): 2486-2494.

Barcia et al., "Anticonvulsant and neurotoxic effects of intracerebroventricular injection of phenytoin, phenobarbital and carbamazepine in an amygdala-kindling model of epilepsy in the rat." Epilepsy research 33.2-3 (1999): 159-167.

Barcia et al., "Intraventricular and intracerebral delivery of anti-epileptic drugs in the kindling model." Neurotherapeutics 6.2 (2009): 337-343.

Barrick et al., "New RNA motifs suggest an expanded scope for riboswitches in bacterial genetic control." Proceedings of the National Academy of Sciences 101.17 (2004): 6421-6426.

Bartel D., "MicroRNAs: genomics, biogenesis, mechanism, and function." cell 116.2 (2004): 281-297.

Bartel et al., "Micromanagers of gene expression: the potentially widespread influence of metazoan microRNAs." Nature reviews genetics 5.5 (2004): 396-400.

Bartel et al., "MicroRNAs: at the root of plant development." Plant physiology 132.2 (2003): 709-717.

Bashirullah et al., "Coordinate regulation of small temporal RNAs at the onset of Drosophila metamorphosis." Developmental biology 259.1 (2003): 1-8.

Baskerville et al., "Microarray profiling of microRNAs reveals frequent coexpression with neighboring miRNAs and host genes." Rna 11.3 (2005): 241-247.

Basyuk et al., "Human let-7 stem-loop precursors harbor features of RNase III cleavage products." Nucleic acids research 31.22 (2003): 6593-6597.

Baulcombe D., "An RNA microcosm." Science 297.5589 (2002): 2002-2003.

Baulcombe D., "RNA silencing in plants." Nature 431.7006 (2004): 356-363.

Beclin et al., "A branched pathway for transgene-induced RNA silencing in plants." Current Biology 12.8 (2002): 684-688.

Bedell et al., "Sorghum genome sequencing by methylation filtration." PLoS Biology 3.1 (2005): 1-13.

Bejerano et al., "Ultraconserved elements in the human genome." Science 304.5675 (2004): 1321-1325.

Bellucci et al., "Graft-versus-tumor response in patients with multiple myeloma is associated with antibody response to BCMA, a plasma-cell membrane receptor." Blood 105.10 (2005): 3945-3950.

Belostotsky D., "mRNA turnover meets RNA interference." Molecular cell 16.4 (2004): 498-500.

Bennasser et al., "HIV-1 encoded candidate micro-RNAs and their cellular targets." Retrovirology 1.1 (2004): 1-5.

Berezikov et al., "Phylogenetic shadowing and computational identification of human microRNA genes." Cell 120.1 (2005): 21-24.

Bergmann et al., "HIDden targets of microRNAs for growth control." Trends in biochemical sciences 28.9 (2003): 461-463.

Bernstein et al., "Role for a bidentate ribonuclease in the initiation step of RNA interference." Nature 409.6818 (2001): 363-366.

Best et al., "In vitro synthesized small interfering RNAs elicit RNA interference in african trypanosomes: an in vitro and in vivo analysis." Journal of Biological Chemistry 280.21 (2005): 20573-20579.

Bettencourt et al., "Hemolin gene silencing by ds-RNA injected into Cecropia pupae is lethal to next generation embryos." Insect Molecular Biology 11.3 (2002): 267-271.

Better et al., "*Escherichia coli* secretion of an active chimeric antibody fragment." Science 240.4855 (1988): 1041-1043.

Bignold L., "The cell-type-specificity of inherited predispositions to tumours: review and hypothesis." Cancer letters 216.2 (2004): 127-146.

Bisson et al., "Prevention and treatment of PTSD: the current evidence base." European Journal of Psychotraumatology 12.1 (2021): 1-5.

Bisson et al., "Psychological therapies for chronic post-traumatic stress disorder (PTSD) in adults." Cochrane database of systematic reviews 12 (2013): 1-167.

Bitko et al., "Inhibition of respiratory viruses by nasally administered siRNA." Nature medicine 11.1 (2005): 50-55.

Blaszczyk et al., "Crystallographic and modeling studies of RNase III suggest a mechanism for double-stranded RNA cleavage." Structure 9.12 (2001): 1225-1236.

Biran et al., "Interaction of temporal lobe epilepsy and post-traumatic stress disorder: network analysis of a single case." Frontiers in Psychology 11 (2020): 1-7.

Bluett et al., "Does change in distress matter? Mechanisms of change in prolonged exposure for PTSD." Journal of behavior therapy and experimental psychiatry 45.1 (2014): 97-104.

Boden et al., "Enhanced gene silencing of HIV-1 specific siRNA using microRNA designed hairpins." Nucleic acids research 32.3 (2004): 1154-1158.

Boffelli et al., "Phylogenetic shadowing of primate sequences to find functional regions of the human genome." Science 299.5611 (2003): 1391-1394.

Bohnsack et al., "Exportin 5 is a RanGTP-dependent dsRNA-binding protein that mediates nuclear export of pre-miRNAs." Rna 10.2 (2004): 185-191.

Bonnet al., "Detection of 91 potential conserved plant microRNAs in *Arabidopsis thaliana* and *Oryza sativa* identifies important target genes." Proceedings of the National Academy of Sciences 101.31 (2004): 11511-11516.

Bonnet et al., "Evidence that microRNA precursors, unlike other non-coding RNAs, have lower folding free energies than random sequences." Bioinformatics 20.17 (2004): 2911-2917.

Borghans et al., "Animal models for posttraumatic stress disorder: an overview of what is used in research." World journal of psychiatry 5.4 (2015): 387-396.

Borodina et al., "Ligation-based synthesis of oligonucleotides with block structure." Analytical biochemistry 318.2 (2003): 309-313.

Boscarino J., "Posttraumatic stress disorder and physical illness: results from clinical and epidemiologic studies." Annals of the New York Academy of sciences 1032.1 (2004): 141-153.

Bothe et al., "How expensive are post-traumatic stress disorders? Estimating incremental health care and economic costs on anonymised claims data." The European Journal of Health Economics 21.6 (2020): 917-930.

Bottros et al., "Current perspectives on intrathecal drug delivery." Journal of pain research (2014): 615-626.

Couzin J., "Human RNA Slows Down a Primate Retrovirus." Science 308.5721 (2005): 480-481.

Couzin J., "RNAi shows cracks in its armor." Science 306.5699 (2004): 1124-1125.

Craik et al., "Deep learning for electroencephalogram (EEG) classification tasks: a review." Journal of neural engineering 16.3 (2019): 1-29.

Crawford et al., "Serum prostate-specific antigen and digital rectal examination for early detection of prostate cancer in a national community-based program." Urology 47.6 (1996): 863-869.

Crestani et al., "Decreased GABAA-receptor clustering results in enhanced anxiety and a bias for threat cues." Nature neuroscience 2.9 (1999): 833-839.

Crestani et al., "Trace fear conditioning involves hippocampal a5 GABAA receptors." Proceedings of the National Academy of Sciences 99.13 (2002): 8980-8985.

Crete et al., "Graft transmission of induced and spontaneous post-transcriptional silencing of chitinase genes." The Plant Journal 28.5 (2001): 493-501.

Cullen B., "RNA interference: antiviral defense and genetic tool." Nature immunology 3.7 (2002): 597-599.

Cullen B., "Transcription and processing of human microRNA precursors." Molecular cell 16.6 (2004): 861-865.

Czeh et al., "Chronic stress reduces the number of GABAergic interneurons in the adult rat hippocampus, dorsal-ventral and region-specific differences." Hippocampus 25.3 (2015): 393-405.

(56)  References Cited

OTHER PUBLICATIONS

Dandekar et al., "HIV-1 Tat directly binds to NFkB enhancer sequence: role in viral and cellular gene expression." Nucleic acids research 32.4 (2004): 1270-1278.

Darce et al., "Regulated expression of BAFF-binding receptors during human B cell differentiation." The Journal of Immunology 179.11 (2007): 7276-7286.

Database GenBank: XP523298.2, "tumor necrosis factor receptor superfamily member 17 [Pan troglodytes]." NCBI.com, Retrieved from the Internet: < URL:https://www.ncbi.nlm.nih.gov/protein/XP_523298.2/> (2006): 1-2.

Davidson et al., "Highly efficient small interfering RNA delivery to primary mammalian neurons induces MicroRNA-like effects before mRNA degradation." Journal of Neuroscience 24.45 (2004): 10040-10046.

Davidson et al., "Molecular medicine for the brain: silencing of disease genes with RNA interference." The Lancet Neurology 3.3 (2004): 145-149.

Davidson et al., "The efficacy and tolerability of tiagabine in adult patients with post-traumatic stress disorder." Journal of clinical psychopharmacology 27.1 (2007): 85-88.

Davidson et al., "Treatment of posttraumatic stress disorder with venlafaxine extended release: a 6-month randomized controlled trial." Archives of general psychiatry 63.10 (2006): 1158-1165.

Davies et al., "Affinity improvement of single antibody VH domains: residues in all three hypervariable regions affect antigen binding." Immunotechnology 2.3 (1996): 169-179.

Davis et al., "Comprehensive review of the psychiatric uses of valproate." Journal of clinical psychopharmacology 20.1 (2000): 1S-17S.

Davis et al., "Divalproex in the treatment of posttraumatic stress disorder: a randomized, double-blind, placebo-controlled trial in a veteran population." Journal of clinical psychopharmacology 28.1 (2008): 84-88.

Davis et al., "Phasic vs sustained fear in rats and humans: role of the extended amygdala in fear vs anxiety." Neuropsychopharmacology 35.1 (2010): 105-135.

De Barros et al., "Gender differences in prevalence of psychiatric disorders, levels of alexithymia, and coping strategies in patients with refractory mesial temporal epilepsy and comorbid psychogenic nonepileptic seizures." Epilepsy & Behavior 82 (2018): 1-5.

De Pascalis et al., "Grafting of "abbreviated" complementarity-determining regions containing specificity-determining residues essential for ligand contact to engineer a less immunogenic humanized monoclonal antibody." The Journal of Immunology 169.6 (2002): 3076-3084.

Deer et al., "Polyanalgesic consensus conference 2007: recommendations for the management of pain by intrathecal (intraspinal) drug delivery: report of an interdisciplinary expert panel." Neuromodulation: Technology at the neural interface 10.4 (2007): 300-328.

Definition of Between, Dictionary.com, Retrieved from the Internet <URL: https://www.dictionary.com/browse/between> (2021): 1-3.

Demidov et al., "Two sides of the coin: affinity and specificity of nucleic acid interactions." Trends in biochemical sciences 29.2 (2004): 62-71.

Denli et al., "Processing of primary microRNAs by the Microprocessor complex." Nature 432.7014 (2004): 231-235.

Dennis C., "Gene regulation: The brave new world of RNA." Nature 418.6894 (2002): 122-125.

Dennis C., "Small RNAs: the genome's guiding hand." Nature 420 (2002): 732.

Di Serio et al., "Sense-and antisense-mediated gene silencing in tobacco is inhibited by the same viral suppressors and is associated with accumulation of small RNAs." Proceedings of the National Academy of Sciences 98.11 (2001): 6506-6510.

Diagnostic And Statistical Manual Of Mental Disorders, 5th ed., DSM-5, American Psychiatric Association (2013) 1-13.

Diergaarde et al., "Pharmacological manipulation of memory reconsolidation: Towards a novel treatment of pathogenic memories." European journal of pharmacology 585.2-3 (2008): 453-457.

Digraham et al., "Ischaemic brain damage is still common in fatal non-missile head injury." Journal of neurology, neurosurgery & Psychiatry 52.3 (1989): 346-350.

Doench et al., "siRNAs can function as miRNAs." Genes & development 17.4 (2003): 438-442.

Doench et al., "Specificity of microRNA target selection in translational repression." Genes & development 18.5 (2004): 504-511.

Domingo-Fernandez et al., "PTSD Biomarker Database: Deep dive metadatabase for PTSD biomarkers, visualizations and analysis tools." Database (2019): 1-8.

Dorsett et al., "siRNAs: applications in functional genomics and potential as therapeutics." Nature reviews Drug discovery 3.4 (2004): 318-329.

Dostie et al., "Numerous microRNPs in neuronal cells containing novel microRNAs." Rna 9.2 (2003): 180-186.

Draghici S., "Statistical intelligence: effective analysis of high-density microarray data." Drug discovery today 7.11 (2002): S55-S63.

Dresios et al., "Cold stress-induced protein Rbm3 binds 60S ribosomal subunits, alters microRNA levels, and enhances global protein synthesis." Proceedings of the National Academy of Sciences 102.6 (2005): 1865-1870.

Dsouza et al., "Searching for patterns in genomic data." Trends in Genetics 13.12 (1997): 497-498.

Duensing et al., "Cyclin-dependent kinase inhibitor indirubin-3'-oxime selectively inhibits human papillomavirus type 16 E7-induced numerical centrosome anomalies." Oncogene 23.50 (2004): 8206-8215.

Dugas et al., "MicroRNA regulation of gene expression in plants." Current opinion in plant biology 7.5 (2004): 512-520.

Dunlop et al., "Assessing treatment-resistant posttraumatic stress disorder: The Emory treatment resistance interview for PTSD (E-TRIP)." Behavioral Sciences 4.4 (2014): 511-527.

Dunoyer et al., "Probing the MicroRNA and small interfering RNA pathways with virus-encoded suppressors of RNA silencing." The Plant Cell 16.5 (2004): 1235-1250.

Duxbury et al., "Systemic siRNA-mediated gene silencing: a new approach to targeted therapy of cancer." Annals of surgery 240.4 (2004): 667-676.

Dykxhoorn et al., "Killing the messenger: short RNAs that silence gene expression." Nature reviews Molecular cell biology 4.6 (2003): 457-467.

Eddy S., "Computational genomics of noncoding RNA genes." Cell 109.2 (2002): 137-140.

Eddy S., "Non-coding RNA genes and the modern RNA world." Nature Reviews Genetics 2.12 (2001): 919-929.

Edwards et al., "Epstein-Barr virus BART microRNAs are produced from a large intron prior to splicing." Journal of virology 82.18 (2008): 9094-9106.

Caudy et al., "Fragile X-related protein and VIG associate with the RNA interference machinery." Genes & development 16.19 (2002): 2491-2496.

Cawley et al., "Unbiased mapping of transcription factor binding sites along human chromosomes 21 and 22 points to widespread regulation of noncoding RNAs." Cell 116.4 (2004): 499-509.

Cerutti H., "RNA interference: traveling in the cell and gaining functions." Trends in Genetics 19.1 (2003): 39-46.

Chang et al., "MicroRNAs act sequentially and asymmetrically to control chemosensory laterality in the nematode." Nature 430.7001 (2004): 785-789.

Chang et al., "miR-122, a mammalian liver-specific microRNA, is processed from hcr mRNA and maydownregulate the high affinity cationic amino acid transporter CAT-1." RNA biology 1.2 (2004): 106-113.

Chang et al., "Resistance of human hepatitis delta virus RNAs to dicer activity." Journal of virology 77.22 (2003): 11910-11917.

Chang P., "Encapsulation for somatic gene therapy." Annals of the New York Academy of Sciences 875.1 (1999): 146-158.

Chapman et al., "Viral RNA silencing suppressors inhibit the microRNA pathway at an intermediate step." Genes & development 18.10 (2004): 1179-1186.

(56) References Cited

OTHER PUBLICATIONS

Chapoval et al., "Anti-CD3 x anti-tumor F (ab') 2 bifunctional antibody activates and retargets tumor-infiltrating lymphocytes." Journal of immunology 155.3 (1995): 1296-1303.

Chattopadhyay et al., "Lack of impact of the loss of constitutive folate receptor a expression, achieved by RNA interference, on the activity of the new generation antifolate pemetrexed in HeLa cells." Clinical cancer research 10.23 (2004): 7986-7993.

Chen et al., "A bioinformatics based approach to discover small RNA genes in the *Escherichia coli* genome." Biosystems 65.2-3 (2002): 157-177.

Chen et al., "A simple framework for contrastive learning of visual representations." International conference on machine learning (2020): 1-11.

Chen et al., "Automatic sleep stage classification based on subthalamic local field potentials." IEEE Transactions on Neural Systems and Rehabilitation Engineering 27.2 (2019): 118-128.

Chen et al., "Improved baselines with momentum contrastive learning." arXiv preprint arXiv:2003.04297 (2020): 1-3.

Chen et al., "MicC, a second small-RNA regulator of Omp protein expression in *Escherichia coli*." Journal of bacteriology 186.20 (2004): 6689-6697.

Chen et al., "MicroRNAs as regulators of mammalian hematopoiesis." Seminars in immunology 17 (2005): 155-165.

Chen et al., "MicroRNAs modulate hematopoietic lineage differentiation." science 303.5654 (2004): 83-86.

Chen et al., "Selection and analysis of an optimized anti-VEGF antibody: crystal structure of an affinity-matured Fab in complex with antigen." Journal of molecular biology 293.4 (1999): 865-881.

Chen et al., "Viral virulence protein suppresses RNA silencing-mediated defense but upregulates the role of microRNA in host gene expression." The Plant Cell 16.5 (2004): 1302-1313.

Chen T., "Advancing Self-Supervised and Semi-Supervised Learning with SimCLR," Blog.research.google, Retrieved from the Internet: <URL: https://research.google/blog/advancing-self-supervised-and-semi-supervised-learning-with-simclr/> (2020): 1-8.

Chen X., "A microRNA as a translational repressor of APETALA2 in *Arabidopsis* flower development." Science 303.5666 (2004): 2022-2025.

Cheng et al., "Antisense inhibition of human miRNAs and indications for an involvement of miRNA in cell growth and apoptosis." Nucleic acids research 33.4 (2005): 1290-1297.

Cheng et al., "Stem cells: from epigenetics to microRNAs." Neuron 46.3 (2005): 363-367.

Chesnut et al., "The role of secondary brain injury in determining outcome from severe head injury." Journal of Trauma and Acute Care Surgery 34.2 (1993): 216-222.

Chiu et al., "Hodgkin lymphoma cells express TACI and BCMA receptors and generate survival and proliferation signals in response to BAFF and APRIL." Blood 109.2 (2007): 729-739.

Cios K., "Deep Neural Networks—A Brief History." in: Gaweda et al., Advances in Data Analysis with Computational Intelligence Methods, vol. 378 (2018): 183-200.

Clark et al., "How does B cell depletion therapy work, and how can it be improved." Annals of the rheumatic diseases 64.suppl 4 (2005): iv77-iv80.

Clarke et al., "Computer-assisted EEG diagnostic review for idiopathic generalized epilepsy." Epilepsy & Behavior 121 (2021): 1-18.

Cobb et al., "Tracing microRNA patterns in mice." Nature genetics 36.10 (2004): 1033-1034.

Coburn et al., "Potent and specific inhibition of human immunodeficiency virus type 1 replication by RNA interference." Journal of virology 76.18 (2002): 9225-9231.

Coenen et al., "What work-related exposures are associated with post-traumatic stress disorder? A systematic review with meta-analysis." BMJ open 11.8 (2021): 1-12.

Cogoni et al., "Post-transcriptional gene silencing across kingdoms." Current opinion in genetics & development 10.6 (2000): 638-643.

Cohen et al., "Neuronal overexpression of 'readthrough' acetylcholinesterase is associated with antisense-suppressible behavioral impairments." Molecular psychiatry 7.8 (2002): 874-885.

Cohen J., "Statistical Power Analysis for the Behavioral Sciences." (Cover page, title page, and table of contents), 2nd Edition (1988): 1-8.

Colciaghi et al., "Platelet APP, ADAM 10 and BACE alterations in the early stages of Alzheimer disease." Neurology 62.3 (2004): 498-501.

Cole et al., "Direct labeling of RNA with multiple biotins allows sensitive expression profiling of acute leukemia class predictor genes." Nucleic acids research 32.11 (2004): 1-9.

Collins et al., "Long subcutaneous tunnelling reduces infection rates in paediatric external ventricular drains." Child's Nervous System 30.10 (2014): 1671-1678.

Colsky et al., "FcR-Independent Antibody-Mediated Cellular Cytotoxicity." Journal of leukocyte biology 49.6 (1991): 548-555.

Conner et al., "Posttraumatic stress disorder and suicide in 5.9 million individuals receiving care in the veterans health administration health system." Journal of affective Disorders 166 (2014): 1-5.

Connolly et al., "Characterization of the relationship between intracranial pressure and electroencephalographic monitoring in burst-suppressed patients." Neurocritical care 22.2 (2015): 212-220.

Connor et al., "Fluoxetine in post-traumatic stress disorder: randomised, double-blind study." The British Journal of Psychiatry 175.1 (1999): 17-22.

Conrad C., "Chronic stress-induced hippocampal vulnerability: the glucocorticoid vulnerability hypothesis." Reviews in the Neurosciences 19.6 (2008): 395-412.

Conrad C., "What is the functional significance of chronic stress-induced CA3 dendritic retraction within the hippocampus." Behavioral and cognitive neuroscience reviews 5.1 (2006): 41-60.

Conway et al., "Chronic vagus nerve stimulation significantly improves quality of life in treatment-resistant major depression." The Journal of Clinical Psychiatry 79.5 (2018): 52-59.

Cook et al., "Anti-seizure therapy with a long-term, implanted intra-cerebroventricular delivery system for drug-resistant epilepsy: A first-in-man study." EClinicalMedicine 22 (2020): 1-9.

Cook et al., "Prediction of seizure likelihood with a long-term, implanted seizure advisory system in patients with drug-resistant epilepsy: a first-in-man study." The Lancet Neurology 12.6 (2013): 563-571.

Coquery et al., "Regulatory roles of the tumor necrosis factor receptor BCMA." Critical Review in Immunology 32.4 (2012): 287-305.

Coquery et al., "T follicular helper cells contribute to autoimmunity through the BCMA-BAFF axis (BA2P. 117)." The Journal of Immunology 192.Supplement_1 (2014): 45-4.

Courtney et al., "Links between traumatic brain injury and ballistic pressure waves originating in the thoracic cavity and extremities." Brain Injury 21.7 (2007): 657-662.

Courtois et al., "Clinical Practice Guideline for the Treatment of Posttraumatic Stress Disorder (PTSD) in Adults." adopted as APA Policy on Feb. 24, 2017, American Psychological Association, 139 pages.

International Search Report and Written Opinion in PCT/US2023/021974, mailed Nov. 24, 2023, 14 pages.

International Search Report and Written Opinion in PCT/US2023/036432, mailed Feb. 28, 2024, 12 pages.

Irani et al., "Production of scFv antibody fragments from a hybridoma with functional activity against human vascular endothelial growth factor." Hybridoma 28.3 (2009): 205-209.

Irving et al., "Top Tips for Overcoming Section 103 Obviousness Rejections." (2018): 1-25.

Isaacson et al., "Local and diffuse synaptic actions of GABA in the hippocampus." Neuron 10.2 (1993): 165-175.

Ishizuka et al., "A *Drosophila* fragile X protein interacts with components of RNAi and ribosomal proteins." Genes & development 16.19 (2002): 2497-2508.

Isken et al., "Complex signals in the genomic 3' nontranslated region of bovine viral diarrhea virus coordinate translation and replication of the viral RNA." Rna 10.10 (2004): 1637-1652.

(56)　　　　　References Cited

OTHER PUBLICATIONS

Isoardi et al., "Increased fear learning coincides with neuronal dysinhibition and facilitated LTP in the basolateral amygdala following benzodiazepine withdrawal in rats." Neuropsychopharmacology 29.10 (2004): 1852-1864.

Itaya et al., "Potato spindle tuber viroid as inducer of RNA silencing in infected tomato." Molecular plant-microbe interactions 14.11 (2001): 1332-1334.

Ivanova et al., "Cost of post-traumatic stress disorder vs major depressive disorder among patients covered by medicaid or private insurance." The American journal of managed care 17.8 (2011): e314-23.

Iyadurai et al., "Intrusive memories of trauma: A target for research bridging cognitive science and its clinical application." Clinical psychology review 69 (2019): 67-82.

Iyer et al., "Evolutionary connection between the catalytic subunits of DNA-dependent RNA polymerases and eukaryotic RNA-dependent RNA polymerases and the origin of RNA polymerases." BMC structural biology 3.1 (2003): 1-23.

Jabri E., "RISCy business." Nature structural & molecular biology 11.4 (2004): 300-300.

Jack T., "Molecular and genetic mechanisms of floral control." The Plant Cell 16 (2004): S1-S17.

Jackson et al., "Expression profiling reveals off-target gene regulation by RNAi." Nature biotechnology 21.6 (2003): 635-637.

Jackson et al., "Noise amidst the silence: off-target effects of siRNAs." Trends in Genetics 20.11 (2004): 521-524.

Jacob et al., "Post-traumatic stress symptoms are associated with physical multimorbidity: Findings from the Adult Psychiatric Morbidity Survey 2007." Journal of Affective Disorders 232 (2018): 385-392.

Jacque et al., "Modulation of HIV-1 replication by RNA interference." Nature 418.6896 (2002): 435-438.

Jaronczyk et al., "Exploring the functions of RNA interference pathway proteins: some functions are more RISCy than others." Biochemical Journal 387.3 (2005): 561-571.

Ji et al., "A graph theoretical approach for predicting common RNA secondary structure motifs including pseudoknots in unaligned sequences." Bioinformatics 20.10 (2004): 1591-1602.

Jiang et al., "Selective silencing of viral gene expression in HPV-positive human cervical carcinoma cells treated with siRNA, a primer of RNA interference." Oncogene 21.39 (2002): 6041-6048.

Jimenez et al., "Contextual fear memory retrieval by correlated ensembles of ventral CA1 neurons." Nature communications 11.1 (2020): 3492.

Jin et al., "Biochemical and genetic interaction between the fragile X mental retardation protein and the microRNA pathway." Nature neuroscience 7.2 (2004): 113-117.

Jin et al., "Enhancer-dependent splicing of FGFR1 a-exon is repressed by RNA interference-mediated down-regulation of SRp55." Cancer research 64.24 (2004): 8901-8905.

Jin et al., "RNA and microRNAs in fragile X mental retardation." Nature cell biology 6.11 (2004): 1048-1053.

Jing et al., "Involvement of microRNA in AU-rich element-mediated mRNA instability." Cell 120.5 (2005): 623-634.

Jobst et al., "Intracranial EEG in the 21st century." Epilepsy currents 20.4 (2020): 180-188.

Johannessen C., "Mechanisms of action of valproate: a commentatory." Neurochemistry international 37.2-3 (2000): 103-110.

John et al., "Human microRNA targets." PLoS biology 2.11 (2004): 1-18.

Johnsen et al., "Consistent impaired verbal memory in PTSD: a meta-analysis." Journal of affective disorders 111.1 (2008): 74-82.

Johnson et al., "Kabat database and its applications: 30 years after the first variability plot." Nucleic acids research 28.1 (2000): 214-218.

Johnson et al., "RAS is regulated by the let-7 microRNA family." Cell 120.5 (2005): 635-647.

Johnson et al., "The time of appearance of the C. elegans let-7 microRNA is transcriptionally controlled utilizing a temporal regulatory element in its promoter." Developmental biology 259.2 (2003): 364-379.

Johnston Jr et al., "A microRNA controlling left/right neuronal asymmetry in Caenorhabditis elegans." Nature 426.6968 (2003): 845-849.

Jones et al., "siRNA for gene silencing: a route to drug target discovery." Current opinion in pharmacology 4.5 (2004): 522-527.

Jones L., "Revealing micro-RNAs in plants." Trends in plant science 7.11 (2002): 473-475.

Jones-Rhoades et al., "Computational identification of plant microRNAs and their targets, including a stress-induced miRNA." Molecular cell 14.6 (2004): 787-799.

Joseph et al., "Validation of miRNA microarray data using MICROMAX ASAP miRNA chemical labeling kit by Northern blot analysis." PerkinElmer Life and Analytical Sciences (2004).

Ju et al., "Correlation of expression levels of BLyS and its receptors with multiple myeloma." Clinical biochemistry 42.4-5 (2009): 387-399.

Juarez et al., "microRNA-mediated repression of rolled leaf1 specifies maize leaf polarity." Nature 428.6978 (2004): 84-88.

Kadotani et al., "One of the two Dicer-like proteins in the filamentous fungi Magnaporthe oryzae genome is responsible for hairpin RNA-triggered RNA silencing and related small interfering RNA accumulation." Journal of Biological Chemistry 279.43 (2004): 44467-44474.

Kalled et al., "BAFF: B cell survival factor and emerging therapeutic target for autoimmune disorders." Expert Opinion on Therapeutic Targets 7.1 (2003): 115-123.

Kalled et al., "The biochemistry and biology of BAFF, APRIL and their receptors." Curr Dir Autoimmun 8 (2004): 206-242.

Kamath et al., "Systematic functional analysis of the Caenorhabditis elegans genome using RNAi." Nature 421.6920 (2003): 231-237.

Kan et al., "New tool for an old problem: can RNAi efficiently resolve the issue of genetic redundancy." Bioessays 27.1 (2005): 14-16.

Kanatsu-Shinohara et al., "Generation of pluripotent stem cells from neonatal mouse testis." Cell 119.7 (2004): 1001-1012.

Kanellopoulou et al., "Dicer-deficient mouse embryonic stem cells are defective in differentiation and centromeric silencing." Genes & development 19.4 (2005): 489-501.

Kang et al., "Induction of DMBT1 expression by reduced ERK activity during a gastric mucosa differentiation-like process and its association with human gastric cancer." Carcinogenesis 26.6 (2005): 1129-1137.

Kao et al., "BACE1 suppression by RNA interference in primary cortical neurons." Journal of Biological Chemistry 279.3 (2004): 1942-1949.

Karlas et al., "Inhibition of porcine endogenous retroviruses by RNA interference: increasing the safety of xenotransplantation." Virology 325.1 (2004): 18-23.

Ryo et al., "Serial analysis of gene expression in HIV-1-infected T cell lines." FEBS letters 462.1-2 (1999): 182-186.

Sackeim et al., "The benefits and costs of changing treatment technique in electroconvulsive therapy due to insufficient improvement of a major depressive episode." Brain stimulation 13.5 (2020): 1284-1295.

Sackeim et al., "The cognitive effects of electroconvulsive therapy in community settings." Neuropsychopharmacology 32.1 (2007): 244-254.

Sackeim, H. "Autobiographical memory and electroconvulsive therapy: do not throw out the baby." The journal of ECT 30.3 (2014): 177-186.

Saito et al., "Gene knockdown: RNA-interference is coming of age." Transfusion 45.1 (2005): 111-114.

Samuelson et al., "Neuropsychological functioning in posttraumatic stress disorder and alcohol abuse." Neuropsychology 20.6 (2006): 1-19.

Sanders et al., "The place of the hippocampus in fear conditioning." European journal of pharmacology 463.1-3 (2003): 217-223.

(56)                  References Cited

OTHER PUBLICATIONS

Sandsmark et al., "Sleep-wake disturbances after traumatic brain injury: synthesis of human and animal studies." Sleep 40.5 (2017): zsx044.

Sanz-Garcia et al., "Identifying causal relationships between EEG activity and intracranial pressure changes in neurocritical care patients." Journal of Neural Engineering 15.6 (2018): 1-10.

Sareen et al., "Anxiety disorders associated with suicidal ideation and suicide attempts in the National Comorbidity Survey." The Journal of nervous and mental disease 193.7 (2005): 450-454.

Saunders et al., "The dsRNA binding protein family: critical roles, diverse cellular functions." The FASEB Journal 17.9 (2003): 961-983.

Saxena et al., "Small RNAs with imperfect match to endogenous mRNA repress translation: implications for off-target activity of small inhibitory RNA in mammalian cells." Journal of Biological Chemistry 278.45 (2003): 44312-44319.

Scacheri et al., "Short interfering RNAs can induce unexpected and divergent changes in the levels of untargeted proteins in mammalian cells." Proceedings of the National Academy of Sciences 101.7 (2004): 1892-1897.

Scangos et al., "Closed-loop neuromodulation in an individual with treatment-resistant depression." Nature medicine 27.10 (2021): 1696-1700.

Schauer et al., "DICER-LIKE1: blind men and elephants in *Arabidopsis* development." Trends in plant science 7.11 (2002): 487-491.

Schein et al., "Prevalence of post-traumatic stress disorder in the United States: a systematic literature review." Current medical research and opinion 37.12 (2021): 2151-2161.

Scherr et al., "Stable RNA interference (RNAi) as an option for anti-bcr-abl therapy." Gene Therapy 12.1 (2005): 12-21.

Schiemann et al., "An essential role for BAFF in the normal development of B cells through a BCMA-independent pathway." Science 293.5537 (2001): 2111-2114.

Schisa et al., "Analysis of RNA associated with P granules in germ cells of C. elegans adults." Development 128.8 (2001): 1287-1298.

Schmittgen et al., "A high-throughput method to monitor the expression of microRNA precursors." Nucleic acids research 32.4 (2004): e43-e43.

Schmitz et al., "Hippocampal GABA enables inhibitory control over unwanted thoughts." Nature communications 8.1 (2017): 1-12.

Schneider et al., "Increased cortical gamma-aminobutyric acid precedes incomplete extinction of conditioned fear and increased hippocampal excitatory tone in a mouse model of mild traumatic brain injury." Journal of neurotrauma 33.17 (2016): 1614-1624.

Schneier et al., "Combined prolonged exposure therapy and paroxetine for PTSD related to the World Trade Center attack: a randomized controlled trial." American Journal of Psychiatry 169.1 (2012): 80-88.

Schnurr et al., "Longitudinal analysis of the relationship between symptoms and quality of life in veterans treated for posttraumatic stress disorder." Journal of consulting and clinical psychology 74.4 (2006): 707-713.

Schnurr et al., "Posttraumatic stress disorder and quality of life: Extension of findings to veterans of the wars in Iraq and Afghanistan." Clinical psychology review 29.8 (2009): 727-735.

Schouby Bock et al., "Clinical validation of the self-reported Glasgow Antipsychotic Side-effect Scale using the clinician-rated UKU side-effect scale as gold standard reference." Journal of Psychopharmacology 34.8 (2020): 820-828.

Schramke et al., "Hairpin RNAs and retrotransposon LTRs effect RNAi and chromatin-based gene silencing." Science 301.5636 (2003): 1069-1074.

Schubert et al., "Local RNA target structure influences siRNA efficacy: systematic analysis of intentionally designed binding regions." Journal of molecular biology 348.4 (2005): 883-893.

Schwabe et al., "Neural signature of reconsolidation impairments by propranolol in humans." Biological psychiatry 71.4 (2012): 380-386.

Schwarz et al., "Asymmetry in the assembly of the RNAi enzyme complex." Cell 115.2 (2003): 199-208.

Schwarz et al., "Why do miRNAs live in the miRNP." Genes & development 16.9 (2002): 1025-1031.

Scott et al., "Associations between lifetime traumatic events and subsequent chronic physical conditions: a cross-national, cross-sectional study." PloS one 8.11 (2013): 1-11.

Seggerson et al., "Two genetic circuits repress the Caenorhabditis elegans heterochronic gene lin-28 after translation initiation." Developmental biology 243.2 (2002): 215-225.

Seidenbecher et al., "Amygdalar and hippocampal theta rhythm synchronization during fear memory retrieval." Science 301.5634 (2003): 846-850.

Seitz et al., "A large imprinted microRNA gene cluster at the mouse Dlk1-Gtl2 domain." Genome research 14.9 (2004): 1741-1748.

Seitz et al., "Imprinted microRNA genes transcribed antisense to a reciprocally imprinted retrotransposon-like gene." Nature genetics 34.3 (2003): 261-262.

Semkovska et al., "Bitemporal versus high-dose unilateral twice-weekly electroconvulsive therapy for depression (EFFECT-Dep): a pragmatic, randomized, non-inferiority trial." American Journal of Psychiatry 173.4 (2016): 408-417.

Sempere et al., "Expression profiling of mammalian microRNAs uncovers a subset of brain-expressed microRNAs with possible roles in murine and human neuronal differentiation." Genome biology 5.3 (2004): 1-11.

Sempere et al., "Temporal regulation of microRNA expression in *Drosophila melanogaster* mediated by hormonal signals and broad-Complex gene activity." Developmental biology 259.1 (2003): 9-18.

Sen et al., "Argonaute 2/RISC resides in sites of mammalian mRNA decay known as cytoplasmic bodies." Nature cell biology 7.6 (2005): 633-636.

Sengupta P., "Taking sides in the nervous system with miRNA." Nature neuroscience 7.2 (2004): 100-102.

Serralta et al., "Effect of intracerebroventricular continuous infusion of valproic acid versus single ip and icv injections in the amygdala kindling epilepsy model." Epilepsy research 70.1 (2006): 15-26.

Shabalina et al., "The mammalian transcriptome and the function of non-coding DNA sequences." Genome biology 5.4 (2004): 1-8.

Shafer et al., "A consensus-based approach to patient safety in epilepsy monitoring units: recommendations for preferred practices." Epilepsy & Behavior 25.3 (2012): 449-456.

Shah et al., "Light-activated RNA interference." Angewandte Chemie International Edition 44.9 (2005): 1328-1332.

Shapiro, F. "Efficacy of the eye movement desensitization procedure in the treatment of traumatic memories." Journal of traumatic stress 2.2 (1989): 199-223.

Sharp, P. "RNA interference—2001." Genes & development 15.5 (2001): 485-490.

Shen et al., "Uridine addition after microRNA-directed cleavage." Science 306.5698 (2004): 997-997.

Sheynin et al., "Circuit dysregulation and circuit-based treatments in posttraumatic stress disorder." Neuroscience Letters 649 (2017): 133-138.

Shi et al., "Selection and characterization of RNA interference-deficient trypanosomes impaired in target mRNA degradation." Eukaryotic Cell 3.6 (2004): 1445-1453.

He et al., ""siRNAs and miRNAs": A meeting report on RNA silencing." RNA (2004): 1165-1173.

He et al., "Lymphoma B cells evade apoptosis through the TNF family members BAFF/BLyS and APRIL." The Journal of Immunology 172.5 (2004): 3268-3279.

He et al., "MicroRNAs: small RNAs with a big role in gene regulation." Nature reviews genetics 5.7 (2004): 522-531.

Heetebrij et al., "Platinum (II)-Based Coordination Compounds as Nucleic Acid Labeling Reagents: Synthesis, Reactivity, and Applications in Hybridization Assays." Chembiochem 4.7 (2003): 573-583.

Hemming et al., "The stepped wedge cluster randomised trial: rationale, design, analysis, and reporting." Bmj 350 (2015): 1-7.

(56) References Cited

OTHER PUBLICATIONS

Henigsberg et al., "Neuroimaging research in posttraumatic stress disorder—Focus on amygdala, hippocampus and prefrontal cortex." Progress in Neuro-Psychopharmacology and Biological Psychiatry 90 (2019): 37-42.

Hershberg et al., "A survey of small RNA-encoding genes in *Escherichia coli*." Nucleic acids research 31.7 (2003): 1813-1820.

Hertzberg et al., "A preliminary study of lamotrigine for the treatment of posttraumatic stress disorder." Biological psychiatry 45.9 (1999): 1226-1229.

Hipfner et al., "The bantam gene regulates *Drosophila* growth." Genetics 161.4 (2002): 1527-1537.

Hobert O., "Common logic of transcription factor and microRNA action." Trends in biochemical sciences 29.9 (2004): 462-468.

Hobert O., "MicroRNAs: all gone and then what." Current Biology 15.10 (2005): R387-R389.

Hofacker et al., "Prediction of locally stable RNA secondary structures for genome-wide surveys." Bioinformatics 20.2 (2004): 186-190.

Holt et al., "Domain antibodies: proteins for therapy." Trends in biotechnology 21.11 (2003): 484-490.

Holway et al., "Systematic, RNA-interference-mediated identification of mus-101 modifier genes in Caenorhabditis elegans." Genetics 169.3 (2005): 1451-1460.

Hooper et al., "The search for a-secretase and its potential as a therapeutic approach to Alzheimer's disease." Current medicinal chemistry 9.11 (2002): 1107-1119.

Houbaviy et al., "Embryonic stem cell-specific MicroRNAs." Developmental cell 5.2 (2003): 351-358.

Howard et al., "Efficient stimulation of site-specific ribosome frameshifting by antisense oligonucleotides." Rna 10.10 (2004): 1653-1661.

Huang et al., "CPEC induces erythroid differentiation of human myeloid leukemia K562 cells through CTP depletion and p38 MAP kinase." Leukemia 18.11 (2004): 1857-1863.

Huang et al., "Homeostatic cell-cycle control by BLyS: Induction of cell-cycle entry but not G1/S transition in opposition to p18INK4c and p27Kip1." Proceedings of the National Academy of Sciences 101.51 (2004): 17789-17794.

Hughes et al., "Functional neuroimaging studies of post-traumatic stress disorder." Expert review of neurotherapeutics 11.2 (2011): 275-285.

Huhn et al., "Efficacy of pharmacotherapy and psychotherapy for adult psychiatric disorders: a systematic overview of meta-analyses." JAMA psychiatry 71.6 (2014): 706-715.

Human herpesvirus 4 complete wild type genome, XP002500227. Retrieved from EBI Database accession No. AJ507799 (2002).

Huppi et al., "Defining and assaying RNAi in mammalian cells." Molecular cell 17.1 (2005): 1-10.

Huse et al., "Generation of a large combinatorial library of the immunoglobulin repertoire in phage lambda." Science 246.4935 (1989): 1275-1281.

Huttenhofer et al., "RNomics: identification and function of small, non-messenger RNAs." Current opinion in chemical biology 6.6 (2002): 835-843.

Hutvagner et al., "A cellular function for the RNA-interference enzyme Dicer in the maturation of the let-7 small temporal RNA." Science 293.5531 (2001): 834-838.

Hutvagner et al., "A microRNA in a multiple-turnover RNAi enzyme complex." Science 297.5589 (2002): 2056-2060.

Hutvagner et al., "RNAi: nature abhors a double-strand." Current opinion in genetics & development 12.2 (2002): 225-232.

Hutvagner et al., "Sequence-specific inhibition of small RNA function." PLoS biology 2.4 (2004): 465-475.

Hydrocephalus and Shunts, Ausmed.com, Retrieved from the Internet: <URL: https://www.ausmed.com/cpd/articles/hydrocephalus-and-shunts> (2023): 1-6.

International Preliminary Report on Patentability in PCT/US2016/019523, mailed Sep. 5, 2017, 12 pages.

International Preliminary Report on Patentability in PCT/US2017/013881, mailed Jul. 24, 2018, 6 pages.

International Preliminary Report on Patentability in PCT/US2018/014387, mailed Jul. 23, 2019, 8 pages.

International Preliminary Report on Patentability in PCT/US2019/068592, mailed Jun. 16, 2021, 9 pages.

International Preliminary Report on Patentability in PCT/US2021/042351, mailed Oct. 28, 2022, 11 pages.

International Preliminary Report on Patentability in PCT/US2022/054049, mailed Jan. 24, 2024, 7 pages.

International Preliminary Report on Patentability in PCT/US2023/012940, mailed Apr. 4, 2024, 9 pages.

International Preliminary Report on Patentability in PCT/US2023/021974, mailed Nov. 7, 2024, 9 pages.

International Preliminary Report on Patentability in PCT/US2023/036432, mailed Apr. 29, 2025, 9 pages.

International Search Report and Written Opinion in PCT/US2016/019523, mailed Jun. 30, 2016, 15 pages.

International Search Report and Written Opinion in PCT/US2017/013881, mailed May 3, 2017, 9 pages.

International Search Report and Written Opinion in PCT/US2017/044452, mailed Nov. 2, 2017, 15 pages.

International Search Report and Written Opinion in PCT/US2018/014387, mailed Apr. 9, 2018, 11 pages.

International Search Report and Written Opinion in PCT/US2019/068592, mailed Apr. 24, 2020, 12 pages.

International Search Report and Written Opinion in PCT/US2021/041763, mailed Nov. 15, 2021, 15 pages.

International Search Report and Written Opinion in PCT/US2021/041766, mailed Nov. 25, 2021, 14 pages.

International Search Report and Written Opinion in PCT/US2021/041772, mailed Nov. 17, 2021, 14 pages.

International Search Report and Written Opinion in PCT/US2021/042351, mailed Oct. 25, 2021, 13 pages.

International Search Report and Written Opinion in PCT/US2022/047860, mailed Feb. 17, 2023, 8 pages.

International Search Report and Written Opinion in PCT/US2022/054049, mailed Apr. 12, 2023, 14 pages.

Lagos-Quintana et al., "Identification of tissue-specific microRNAs from mouse." Current biology 12.9 (2002): 735-739.

Lagos-Quintana et al., "New microRNAs from mouse and human." Rna 9.2 (2003): 175-179.

Lai et al., "Complementary miRNA pairs suggest a regulatory role for miRNA: miRNA duplexes." Rna 10.2 (2004): 171-175.

Lai et al., "Computational identification of *Drosophila* microRNA genes." Genome biology 4.7 (2003): 1-20.

Lai et al., "Pervasive regulation of *Drosophila* Notch target genes by GY-box-, Brd-box-, and K-box-class microRNAs." Genes & development 19.9 (2005): 1067-1080.

Lai, E. "Micro RNAs are complementary to 3' UTR sequence motifs that mediate negative post-transcriptional regulation." Nature genetics 30.4 (2002): 363-364.

Lambert et al., "Measurement of antipsychotic-induced side effects: Support for the validity of a self-report (LUNSERS) versus structured interview (UKU) approach to measurement." Human Psychopharmacology: Clinical and Experimental 18.5 (2003): 405-411.

Lamminmaki et al., "Crystal structure of a recombinant anti-estradiol Fab fragment in complex with 17β-estradiol." Journal of Biological Chemistry 276.39 (2001): 36687-36694.

Lamontagne et al., "Molecular requirements for duplex recognition and cleavage by eukaryotic RNase III: discovery of an RNA-dependent DNA cleavage activity of yeast Rnt1p." Journal of molecular biology 338.2 (2004): 401-418.

Landthaler et al., "The human DiGeorge syndrome critical region gene 8 and Its D. melanogaster homolog are required for miRNA biogenesis." Current biology 14.23 (2004): 2162-2167.

Lantto et al., "Functional consequences of insertions and deletions in the complementarity-determining regions of human antibodies." Journal of Biological Chemistry 277.47 (2002): 45108-45114.

Latchoumycandane et al., "Protein kinase Cd is a key downstream mediator of manganese-induced apoptosis in dopaminergic neuronal cells." The Journal of pharmacology and experimental therapeutics 313.1 (2005): 46-55.

(56) References Cited

OTHER PUBLICATIONS

Lau et al., "An abundant class of tiny RNAs with probable regulatory roles in Caenorhabditis elegans." Science 294.5543 (2001): 858-862.

Lau et al., "Censors of the genome." Scientific American 289.2 (2003): 34-41.

Laufs et al., "MicroRNA regulation of the CUC genes is required for boundary size control in *Arabidopsis* meristems." (2004): 4311-4322.

Laxminarayan et al., "Alterations in sleep electroencephalography synchrony in combat-exposed veterans with post-traumatic stress disorder." Sleep 43.7 (2020): 1-11.

Lecellier et al., "A cellular microRNA mediates antiviral defense in human cells." Science 308.5721 (2005): 557-560.

Ledoux, J. "The emotional brain, fear, and the amygdala." Cellular and molecular neurobiology 23.4 (2003): 727-738.

Lee et al., "An extensive class of small RNAs in Caenorhabditis elegans." science 294.5543 (2001): 862-864.

Lee et al., "Depletion of human micro-RNA miR-125b reveals that it is critical for the proliferation of differentiated cells but not for the down-regulation of putative targets during differentiation." Journal of Biological Chemistry 280.17 (2005): 16635-16641.

Lee et al., "Distinct roles for *Drosophila* Dicer-1 and Dicer-2 in the siRNA/miRNA silencing pathways." Cell 117.1 (2004): 69-81.

Lee et al., "Expression of small interfering RNAs targeted against HIV-1 rev transcripts in human cells." Nature biotechnology 20.5 (2002): 500-505.

Lee et al., "Independent cellular processes for hippocampal memory consolidation and reconsolidation." Science 304.5672 (2004): 839-843.

Lee et al., "MicroRNA genes are transcribed by RNA polymerase II." The EMBO journal 23.20 (2004): 4051-4060.

Lee et al., "MicroRNA maturation: stepwise processing and subcellular localization." The EMBO journal (2002): 4663-4670.

Lee et al., "Occupational post-traumatic stress disorder: an updated systematic review." BMC public health 20.1 (2020): 1-12.

Lee et al., "The C. elegans heterochronic gene lin-4 encodes small RNAs with antisense complementarity to lin-14." cell 75.5 (1993): 843-854.

Lee et al., "The nuclear RNase III Drosha initiates microRNA processing." Nature 425.6956 (2003): 415-419.

Legendre et al., "Profile-based detection of microRNA precursors in animal genomes." Bioinformatics 21.7 (2005): 841-845.

Leonard et al., "Computational design of antiviral RNA interference strategies that resist human immunodeficiency virus escape." Journal of Virology 79.3 (2005): 1645-1654.

Leontariti et al., "Circulating miR-146a and miR-134 in predicting drug-resistant epilepsy in patients with focal impaired awareness seizures." Epilepsia 61.5 (2020): 959-970.

Lesuis et al., "Glucocorticoids promote fear generalization by increasing the size of a dentate gyrus engram cell population." Biological psychiatry 90.7 (2021): 494-504.

Levanon et al., "Systematic identification of abundant A-to-I editing sites in the human transcriptome." Nature biotechnology 22.8 (2004): 1001-1005.

Lewis et al., "Conserved seed pairing, often flanked by adenosines, indicates that thousands of human genes are microRNA targets." cell 120.1 (2005): 15-20.

Lewis et al., "Prediction of mammalian microRNA targets." Cell 115.7 (2003): 787-798.

Lewis et al., "Psychological therapies for post-traumatic stress disorder in adults: Systematic review and meta-analysis." European journal of psychotraumatology 11.1 (2020): 1729633.

Li et al., "Computational identification of novel family members of microRNA genes in *Arabidopsis thaliana* and *Oryza sativa*." Acta biochimica et biophysica Sinica 37.2 (2005): 75-87.

Li et al., "EEG based emotion identification using unsupervised deep feature learning." (2015): 1-2.

Li et al., "Induction and suppression of RNA silencing by an animal virus." Science 296.5571 (2002): 1319-1321.

Li et al., "Specific inhibition of HIV-1 replication by short hairpin RNAs targeting human cyclin T1 without inducing apoptosis." FEBS letters 579.14 (2005): 3100-3106.

Liang et al., "A small yeast RNA inhibits HCV IRES mediated translation and inhibits replication of poliovirus in vivo." World Journal of Gastroenterology: WJG 9.5 (2003): 1008-1013.

Liang et al., "An oligonucleotide microarray for microRNA expression analysis based on labeling RNA with quantum dot and nanogold probe." Nucleic acids research 33.2 (2005): 1-8.

Liang et al., "Inhibitor RNA blocks the protein translation mediated by hepatitis C virus internal ribosome entry site in vivo." World Journal of Gastroenterology 10.5 (2004): 664-667.

Liao et al., "Biomembrane-permeable and ribonuclease-resistant siRNA with enhanced activity." Oligonucleotides 15.3 (2005): 196-205.

Lim et al., "Microarray analysis shows that some microRNAs downregulate large numbers of target mRNAs." Nature 433.7027 (2005): 769-773.

Lim et al., "The microRNAs of Caenorhabditis elegans." Genes & development 17.8 (2003): 991-1008.

Lim et al., "Vertebrate microRNA genes." Science 299.5612 (2003): 1540-1540.

Lin et al., "The C. elegans hunchback homolog, hbl-1, controls temporal patterning and is a probable microRNA target." Developmental cell 4.5 (2003): 639-650.

Lindley et al., "A randomized, double-blind, placebo-controlled trial of augmentation topiramate for chronic combat-related post-traumatic stress disorder." Journal of clinical psychopharmacology 27.6 (2007): 677-681.

Lingjaerde O., "The UKU side effect rating scale: a new comprehensive rating scale for psychotropic drugs and a cross-sectional study of side effects in neuroleptic-treated patients." Acta Psychiatrica Scandinavica 334.76 (1987): 1-95.

* cited by examiner

FLUID CATHETER DEVICE FOR RECORDING BRAIN STATE

RELATED APPLICATION

This application claims the benefit of U.S. Provisional Application No. 63/053,864 filed on Jul. 20, 2020, which application is hereby incorporated herein by reference in its entirety to the extent that it does not conflict with the disclosure presented herein.

FIELD

The present disclosure relates to, among other things, devices and systems configured to carry fluid to or from a cerebrospinal fluid containing brain compartment and to record electrical signals from the brain.

INTRODUCTION

Catheters and associated devices have been employed to deliver therapeutic agents to compartments of the brain comprising cerebral spinal fluid (CSF) or for withdrawing CSF from the brain. The catheters may be used to drain CSF from the brain, such as with a ventriculoperitoneal shunt or external ventricular drain; to percutaneously deliver therapeutic fluid to, or withdraw CSF from, the CSF space, such as with Ommaya or Rickman's reservoir; or to infuse therapeutic agent to the CSF space, such as with an implantable infusion device. Surgical procedures to implant the catheters and associated devices are invasive. For example, surgical placement of the catheter alone requires a burr hole to be drilled through the skull and the catheter to be advanced through brain tissue to reach the CSF-containing compartment.

In some cases, such catheters and associated devices may be used to monitor a patient's health or therapy progression. For example, if the device includes an access port for withdrawing CSF through catheter, the withdrawn CSF may be evaluated, for example, to determine whether the patient has a bacterial, fungal, or viral infection or to determine whether a delivered therapeutic agent is present in the CSF at effective concentrations. However, monitoring of electrical brain signals, which may be important for monitoring the therapy, a condition being treated, or a brain state, is not possible with such devices.

Brain activity may be monitored in such patients by using a separate system to record brain activity from the scalp. Such electroencephalogram (EEG) recordings may be useful for periodic monitoring of the patient's brain activity but are not suitable for long-term, continuous monitoring for patients that are not confined to a health care facility. In addition, the signal provided by such EEG recordings tends to be noisy and of lower quality due to signal attenuation through the skull and scalp.

SUMMARY

The present disclosure relates to, among other things, devices and systems that include catheters for delivering therapeutic agents to the brain or withdrawing CSF from the brain and that include electrodes configured to be positioned within or close to white matter of the brain or grey matter of the brain. The electrodes may record electrical signals from within the brain.

By placing the electrodes within or in proximity to brain tissue, such as white matter or grey matter, less "noisy"

signals may be obtained than with scalp-based EEG recordings. Such higher quality signals may facilitate interpretation of data recorded by the electrodes.

An electrode may be fixed a relative to a distal end of the catheter such that implanting the distal end of the catheter in the CSF-containing space causes the electrode to be placed in contact with the white or grey matter. The catheter may comprise the electrode. A separate lead may comprise the electrode. The lead may be placed adjacent to the catheter. If a separate lead comprises the electrode, the lead may be fixed relative to the catheter such that the electrode is a suitable distance from the distal end of the catheter to be positioned in contact with the white or grey matter when the distal end of the catheter is positioned in the CSF-containing space. Accordingly, a single implantation procedure may be performed to implant both the catheter and the electrode. Advantageously, the surgical implantation procedure is less complex and less invasive than procedures in which a catheter and a lead are separately implanted and positioned.

Preferably, the catheter comprises multiple lumens. A first lumen may be used, for example, to withdraw CSF from the brain, and a second lumen may be used, for example, to deliver a therapeutic fluid to the brain. The withdrawn CSF may be used to monitor disease or therapy progression, as well as monitor brain state, which may be used to, for example, adjust the rate of delivery of the therapeutic agent.

In addition or alternatively, data recorded by the electrode may be used to monitor disease or therapy progression, as well as monitor a current brain state or predict a future brain state. The rate of delivery of the therapeutic fluid may be adjusted based on data recorded by the electrode.

The combination of analysis of withdrawn CSF and data recorded by the electrode may result in substantially improved therapy and therapeutic outcomes than analysis of either alone.

According to an aspect of the present disclosure, a device or system for delivering fluid to or removing fluid from a CSF-containing space of a brain and for recording electrical activity from within the brain, comprises a catheter comprising a proximal end, a distal end portion, and a first lumen extending from the proximal end to the distal end portion. The device or system comprises an electrode positioned a distance from a distal end of the catheter such that the electrode would be placed in contact with white matter or grey matter of the brain if the distal end of the catheter were positioned in the CSF-containing space. If a distal end of the catheter is configured to be positioned in a cerebral ventricle, the electrode may be placed, for example, from about 0.5 centimeters to about 6 centimeters from the distal end.

The catheter may comprise the electrode. A lead may comprise the electrode. The lead may be secured relative to the catheter such that implanting the catheter causes the lead to be implanted such that when the distal end of the catheter is positioned in a cerebrospinal fluid (CSF)-containing space of a brain of a subject, the electrode of the lead is placed in contact with the white matter or the grey matter.

The device or system may comprise an access port. The access port may be configured to be implanted under the scalp of the subject. The access port may comprise an opening, a first catheter connector, and a first fluid flow path from the opening to the first catheter connector. The proximal end of the catheter may be coupled to the first catheter connector such that the first lumen is in communication with the first fluid flow path. The opening may be accessible by a needle inserted through skin of the subject, such as through the scalp of the subject, to allow delivery of fluid to the CSF-containing space or withdrawal of CSF through the first fluid flow path and first lumen.

The catheter may comprise a second lumen extending from the proximal end to the distal end portion. The access port may comprise a second fluid flow path extending from a second catheter connector to the first catheter connector. A device, such as an implantable infusion device, a CSF drainage catheter, or the like, may be operably coupled to the second catheter connector to allow therapeutic fluid to be infused through the second fluid flow path and second lumen or to allow CSF to drain from the CSF-containing space through the second lumen and second fluid flow path. Such a configuration permits CSF to be aspirated through the first flow path for analysis, while therapeutic fluid flow or CSF drainage continues through the second flow path.

The second fluid flow path may comprise a filter, such as a microbial filter. The first fluid flow path preferably does not comprise a microbial filter.

The device or system may comprise signal apparatus operably coupled to the one or more electrodes. The signal apparatus may be implanted in the subject and may be configured to process, transmit, or process and transmit data regarding the electrical signal recorded by the electrode.

The device or system may comprise an external apparatus configured to receive the data regarding the electrical signal transmitted by the signal apparatus. The external apparatus may be configured to wirelessly power the signal apparatus.

The device or system may be configured to alter the rate of delivery of therapeutic fluid based on the data regarding the electrical signal recorded by the electrode.

According to an aspect of the present disclosure, a device or system comprises an access port. The access port may be configured to be implanted under a scalp of a subject. The access port comprises (i) an opening accessible by a needle inserted through skin of the subject, such as the scalp of the subject, when the access port is implanted; (ii) a first catheter connector; (iii) a second catheter connector, (iv) a first fluid flow path extending from the opening to a first catheter connector; and (v) a second fluid flow path extending from the second catheter connector to the first catheter connector. The device or system further comprises a catheter coupled to, or operably couplable to, the first catheter connector. The catheter comprises a proximal end, a distal end portion, and first and second lumens extending from the proximal end to the distal end portion of the catheter. The first lumen is in communication with the first fluid flow path and the second lumen is in communication with the second fluid flow path when the proximal end of the catheter is coupled to the first catheter connector. The catheter has a length such that a distal end of the catheter is configured to extend to a CSF-containing space of a subject when the access port is implanted. The device or system also includes an electrode positioned a distance from a distal end of the catheter such that the electrode is positioned in white matter or grey matter of a brain of the subject when the access port is implanted and when the distal end of the catheter is positioned in the CSF-containing space.

The second fluid flow path may comprise a filter, such as a microbial filter. The first fluid flow path preferably does not comprise a microbial filter.

The catheter may comprise the electrode. A lead may comprise the electrode. The lead may be secured relative to the catheter such that implanting the catheter causes the lead to be implanted such that when the distal end of the catheter is positioned in the (CSF)-containing space of a brain of a subject, the electrode of the lead is placed in contact with the white matter or the grey matter.

The device or system may comprise signal apparatus electrically coupled to, or configured to electrically couple to, the electrode. The signal apparatus may be implanted in the subject and may be configured to process, transmit, or process and transmit data regarding the electrical signal recorded by the one or more electrodes.

The device or system may comprise an external apparatus configured to receive the data regarding the electrical signal transmitted by the signal apparatus. The external apparatus may be configured to wirelessly power the signal apparatus.

The device or system may be configured to alter the rate of delivery of therapeutic fluid based on the data regarding the electrical signal recorded by the electrode.

According to an aspect of the present disclosure, a method comprises recording an electrical signal from white matter or grey matter of a brain of a subject and determining a brain state of the subject or predicting a future brain state of the subject based on the recorded electrical signal.

Recording the electrical signal from the white matter or the grey matter of the brain of the subject may comprise recording the signal from an electrode positioned in the white matter or grey matter. A catheter may comprise the electrode. The catheter configured to deliver fluid to, or withdraw fluid from, a CSF-containing space of the subject. The catheter may be positioned to deliver fluid to, or withdraw fluid from, a CSF-containing space of the subject, such as a cerebral ventricle.

A lead may comprise the electrode. The lead may be fixed to a catheter configured to deliver fluid to, or withdraw fluid from, a CSF-containing space of the subject such that when the catheter is positioned to deliver fluid to, or withdraw fluid from, the CSF-containing space, the electrode of the lead is placed in contact with the white matter or the grey matter.

The method may further comprise applying an electrical signal to the white or grey matter. Recording the electrical signal from the white matter of the brain of the subject may comprise recording an electrical response evoked by the applied electrical signal. Applying an electrical signal to the white or grey matter may comprise applying the signal via a stimulating electrode positioned in the white or grey matter. The stimulating electrode may be the same as, or different than, the recording electrode.

The method may comprise provoking the subject. Recording the electrical signal from the white matter of the brain of the subject may comprise recording a provoked electrical response.

According to an aspect of the present disclosure, a method comprises delivering fluid to, or withdrawing fluid from, a CSF-containing space, such as a cerebral ventricle, of a brain of a subject. The fluid is delivered or withdrawn through a first lumen of a catheter. The method further comprises recording an electrical signal from the white or grey matter via an electrode. The electrode is positioned and fixed relative to the catheter such that implanting the catheter such that the catheter may deliver fluid to or with draw fluid from the CSF-containing space causes the electrode to be placed in contact with the white or grey matter.

The catheter may comprise the electrode. A lead may comprise the electrode. The lead may be fixed to a catheter configured to deliver fluid to, or withdraw fluid from, a CSF-containing space of the subject such that when the catheter is positioned to deliver fluid to, or withdraw fluid from, the CSF-containing space, the electrode of the lead is placed in contact with the white matter or the grey matter.

The method may comprise transmitting data regarding the recorded electrical signal to apparatus external to the subject.

The method may comprise determining a brain state of the subject or predicting a future brain state of the subject based on the recorded electrical signal.

The method may comprise applying an electrical signal to the white or grey matter. Recording the electrical signal from the white or grey matter of the brain of the subject may comprise recording an electrical response evoked by the applied electrical signal. The signal may be applied by the electrode positioned in white matter or grey of the brain.

According to an aspect of the present disclosure, a method comprises providing a device or system comprising an access port, a catheter, and an electrode. The access port may be configured to be implanted under a scalp of a subject. The access port comprises (i) an opening accessible by a needle inserted through skin of the subject, such as the scalp of the subject, when the access port is implanted; (ii) a first catheter connector; (iii) a second catheter connector; (iv) a first fluid flow path extending from the opening to a first catheter connector; and (v) a second fluid flow path extending from the second catheter connector to the first catheter connector. The catheter is coupled to, or operably couplable to, the first catheter connector. The catheter comprises a proximal end, a distal end portion, first and second lumens extending from the proximal end to the distal end portion of the catheter. The first lumen is in communication with the first fluid flow path and the second lumen is in communication with the second fluid flow path when the proximal end of the catheter is coupled to the first catheter connector. The catheter has a length such that a distal end of the catheter is configured to extend to a CSF-containing space of a subject when the access port is implanted in the subject. The electrode is positioned a distance from the distal end portion of the catheter such that the electrode is positioned in white or grey matter of a brain of the subject when the access port is implanted and the distal end of the catheter is positioned in the CSF-containing space. The method further comprises implanting the device or system such that the proximal end of the catheter is coupled to the first catheter connector, the first lumen of the catheter is in communication with the first fluid flow path of the access port, the second lumen of the catheter is in communication with the second fluid flow path of the access port, the distal end of the catheter is positioned in the CSF-containing space of the subject, and the electrode is positioned in the white or grey matter of the brain of the subject. The method also comprises recording an electrical signal from the white or grey matter via the electrode.

The second fluid flow path may comprise a filter, such as a microbial filter. The first fluid flow path preferably does not comprise a microbial filter.

The catheter may comprise the electrode. A lead may comprise the electrode. The lead may be fixed to the catheter such that when the distal end of the catheter is positioned in the CSF-containing space, the electrode of the lead is placed in contact with the white matter or the grey matter.

The method may comprise transmitting data regarding the recorded electrical signal to apparatus external to the subject. The method may comprise determining a brain state of the subject or predicting a future brain state of the subject based on the recorded electrical signal. The method may comprise applying an electrical signal to the white or grey matter, wherein recording the electrical signal from the white or grey matter of the brain of the subject comprises recording an electrical response evoked by the applied electrical signal. The signal may be applied by the one or more electrodes positioned in white or grey matter of the brain.

The method may comprise infusing a therapeutic fluid through the second fluid flow path of the access port and through the second lumen of the catheter. The second lumen may be in communication with the CSF-containing space, such as a cerebral ventricle. The method may comprise altering the rate at which the therapeutic fluid is infused based on data regarding the recorded electrical signal.

According to an aspect of the present disclosure, a method comprises implanting a catheter such that a distal end is positioned in a cerebrospinal fluid (CSF)-containing space of a brain of a subject. Implanting the catheter causes an electrode to be placed in contact with white matter or grey matter of the brain. The method includes infusing therapeutic fluid into the CSF-containing space, or withdrawing CSF from the CSF-containing space, via a lumen of the catheter. The method further includes recording an electrical signal from the white or grey matter via the electrode.

The catheter may comprise the electrode. A lead may comprise the electrode. The lead may be secured relative to the catheter such that implanting the catheter causes the lead to be implanted such that when the distal end of the catheter is positioned in a cerebrospinal fluid (CSF)-containing space of a brain of a subject, the electrode of the lead is placed in contact with the white matter or the grey matter.

The catheter may comprise multiple lumens that extend from a distal end portion to a proximal end portion. A first lumen may be configured for withdrawing CSF from the CSF-containing space in which the distal end of the catheter is implanted. A second lumen may be configured for introducing fluid into the CSF-containing space in which the distal end of the catheter is implanted.

The catheter may be a part of a system comprising an access port. The access port may comprise a first fluid pathway in fluid communication with the first lumen of the catheter and a second fluid pathway in fluid communication with the second lumen of the catheter. The second fluid pathway may comprise a filter, such as a microbial filter. Preferably, the first fluid pathway does not comprise a microbial filter.

The devices, systems, and methods described herein may be used for any suitable purpose, including treating a subject at risk or suffering from a brain disease.

The details of one or more aspects of the disclosure are set forth in the accompanying drawings and the description below. Other features, objects, and advantages of the techniques described in this disclosure will be apparent from the description and drawings, and from the claims.

7

Figure 8:
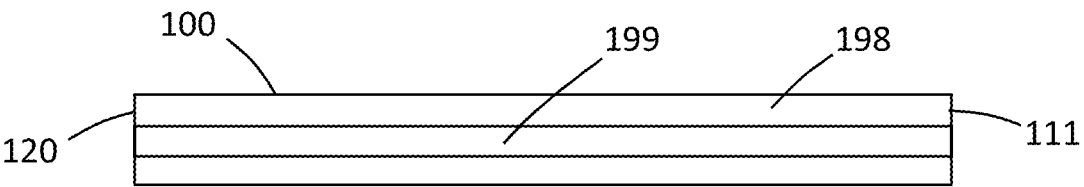

FIG. 8 is a schematic side view illustrating an embodiment of a catheter comprising a groove configured to receive a lead.

Figure 9:
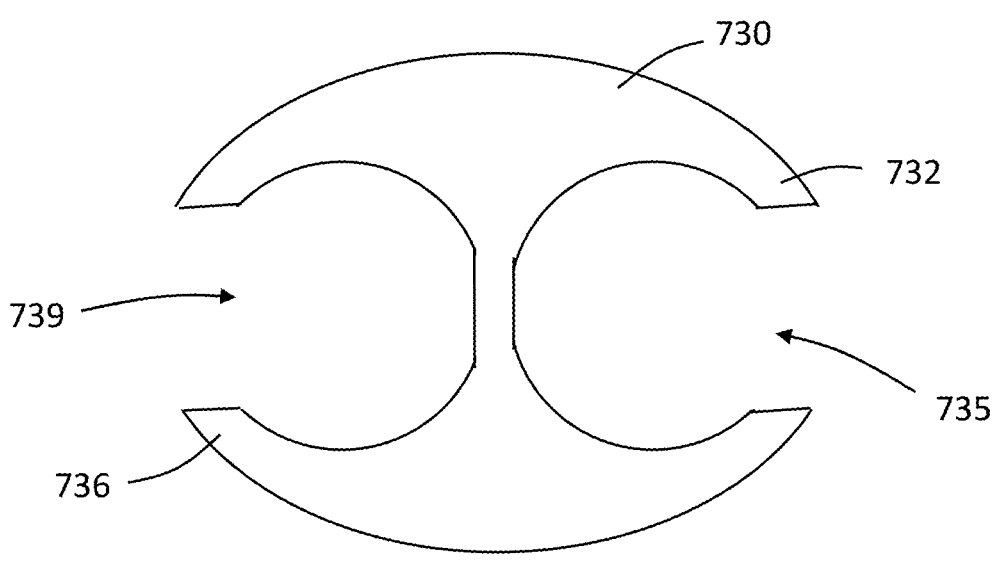

FIG. 9 is a schematic top view of an embodiment of a connector configured to retain a lead relative to a catheter.

Figures 10A, 10B:
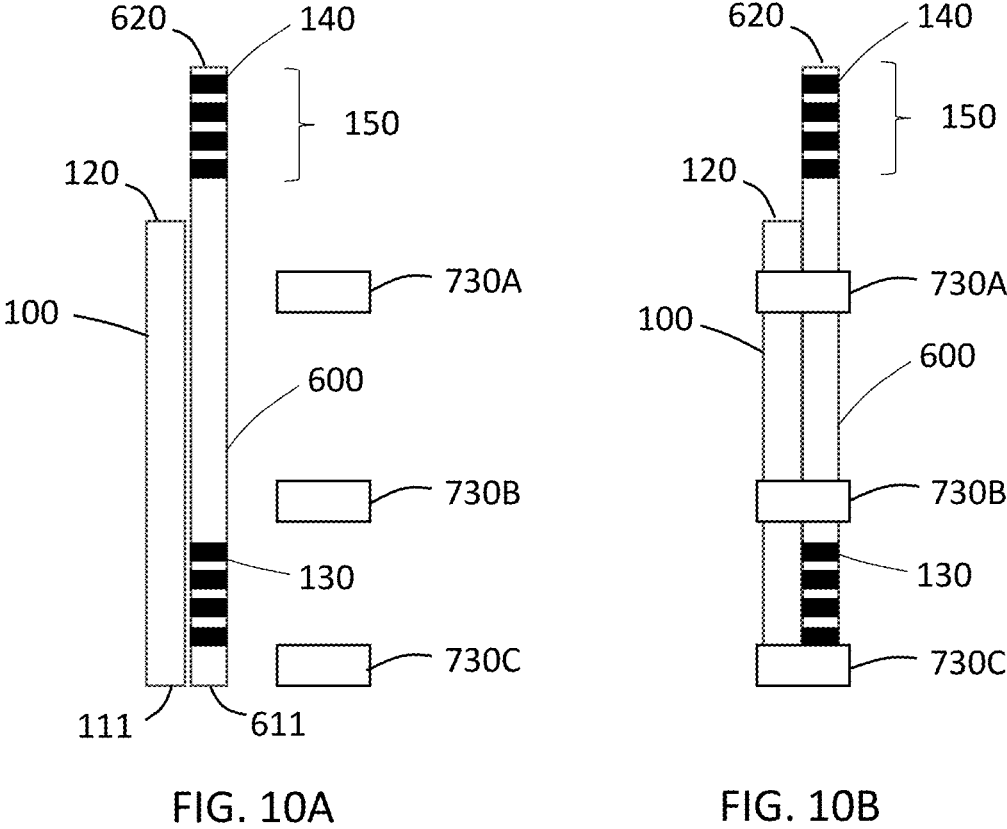

FIGS. 10A-B are schematic side views of an embodiment illustrating a lead, catheter, and connectors for securing the lead relative to the catheter.

Figures 11, 12:
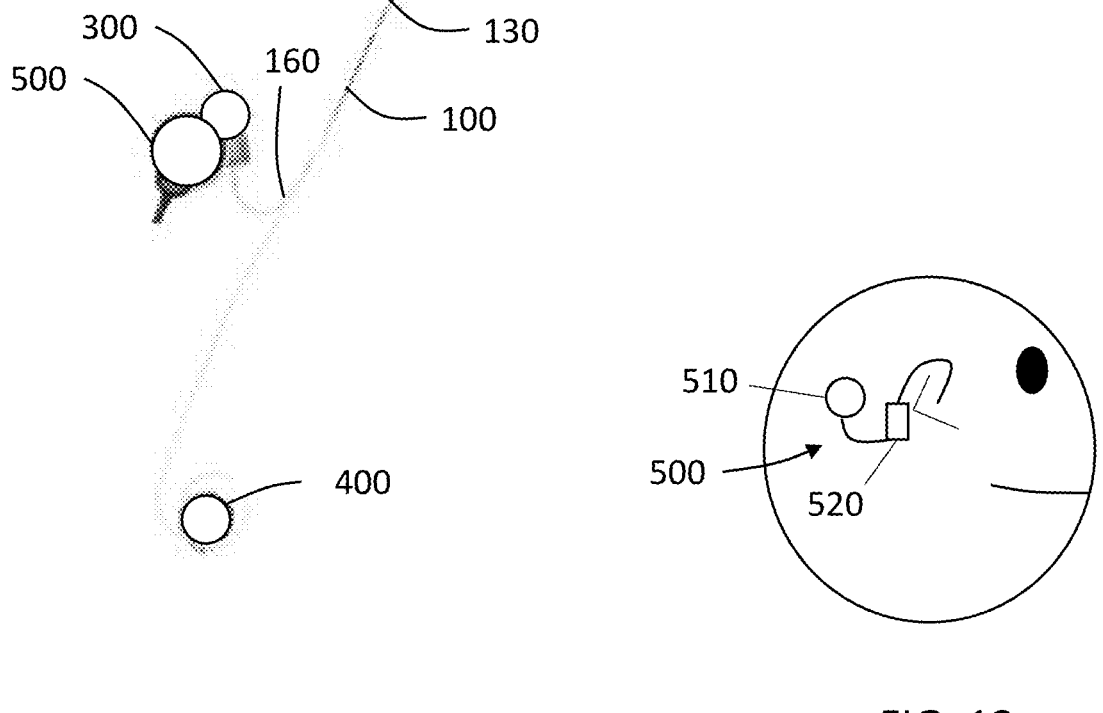

FIG. 11 is a schematic view of an embodiment of implantable infusion device, signal apparatus, catheter with electrodes, and external apparatus.

FIG. 12 is a schematic view of an embodiment of an external apparatus being worn around an ear of a subject.

Figure 13:
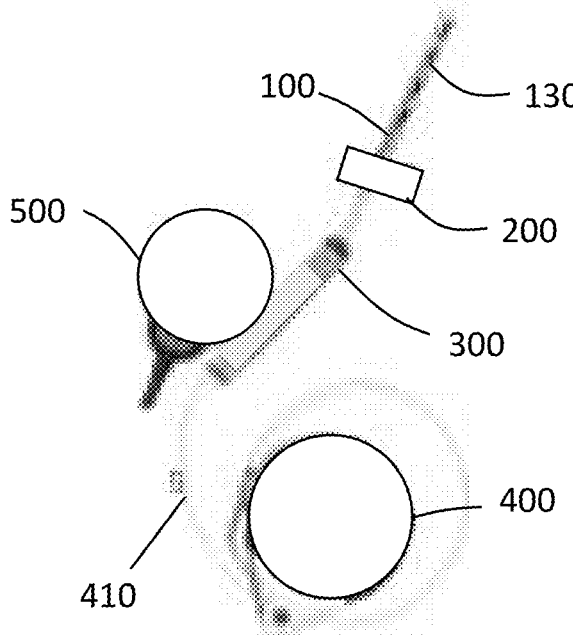

FIG. 13 is a schematic view of an embodiment of an implantable infusion device, a catheter containing electrodes and signal apparatus, and external apparatus.

Figure 14:
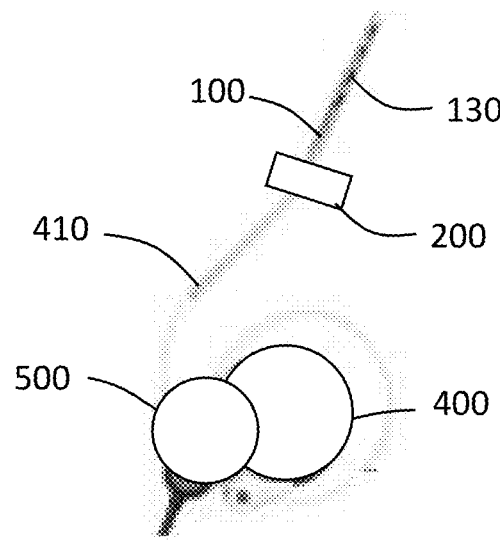

FIG. 14 is a schematic view of an embodiment of an implantable infusion device containing signal apparatus, a catheter containing electrodes, and external apparatus.

Figure 15:
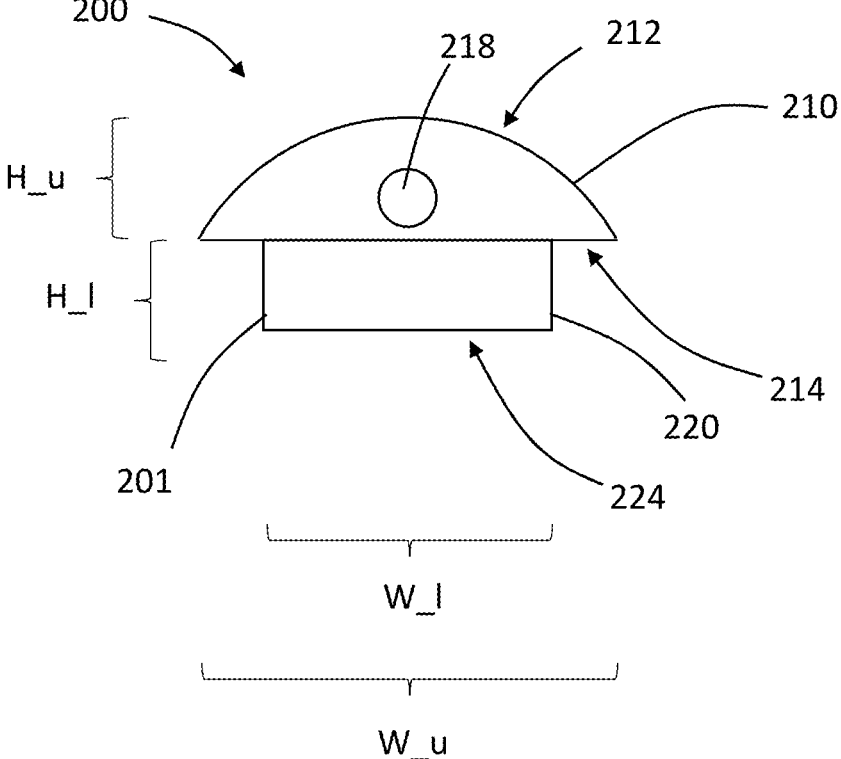

FIG. 15 is a schematic side view of an embodiment of an access port.

Figures 16, 17:
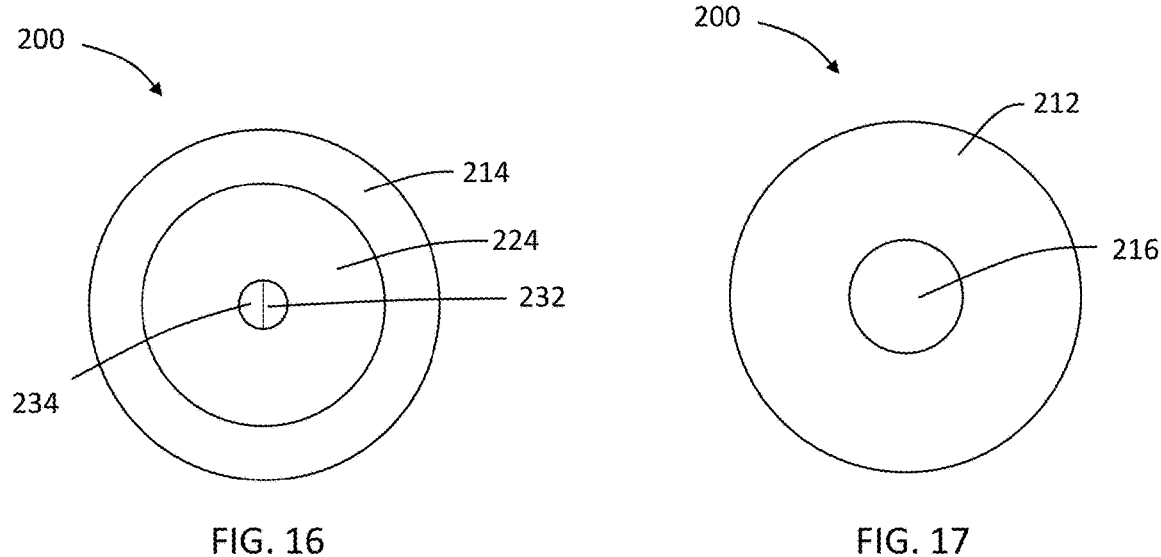

FIG. 16 is a schematic bottom view of the embodiment of the access port depicted in FIG. 15.

FIG. 17 is a schematic top view of the embodiment of the access port depicted in FIGS. 15 and 16.

Figure 18:
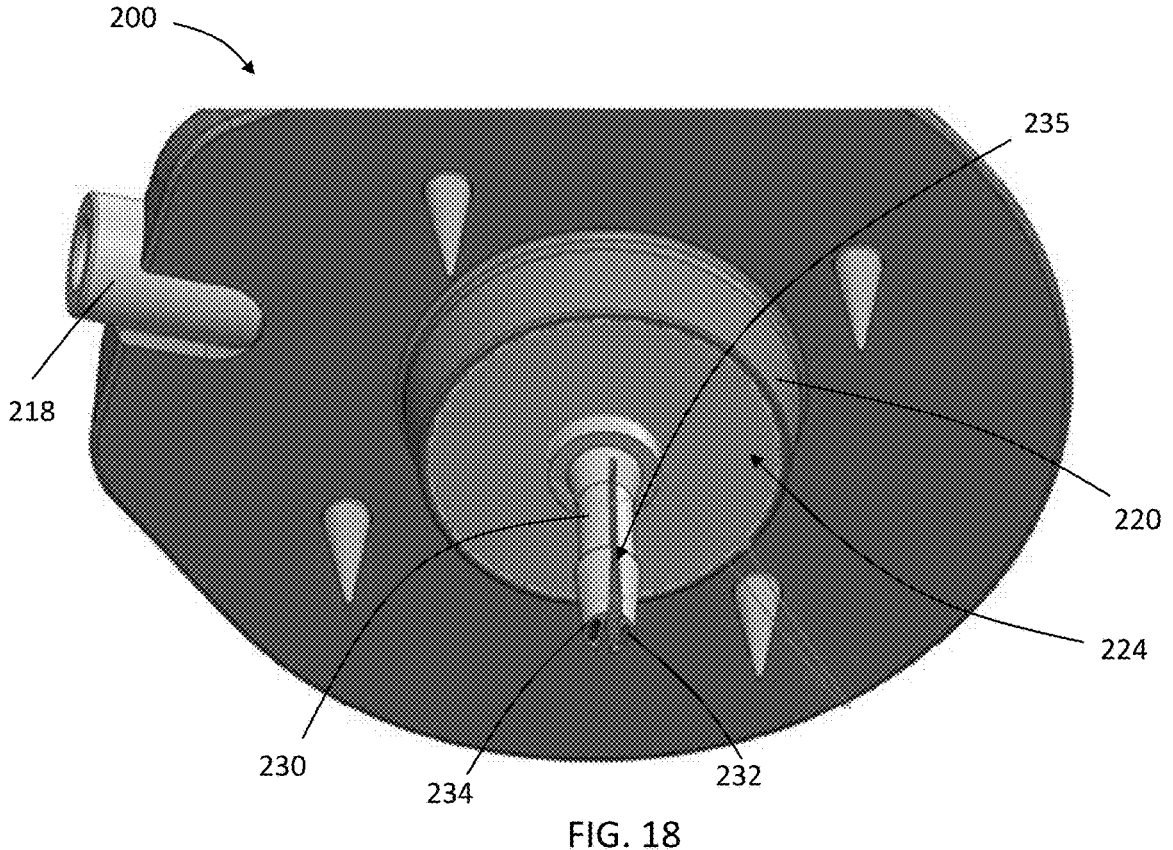

FIG. 18 is a schematic perspective view showing a bottom of an embodiment of an access port.

Figure 19:
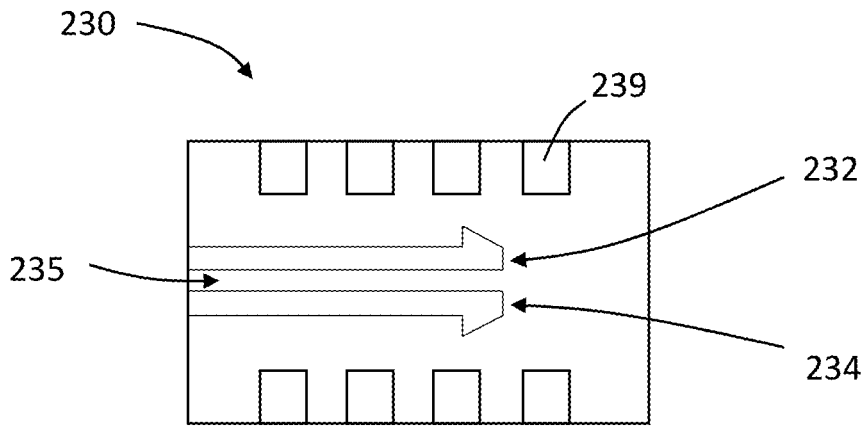

FIG. 19 is a schematic cross-sectional view of an embodiment of a catheter connector and interconnect.

Figure 20:
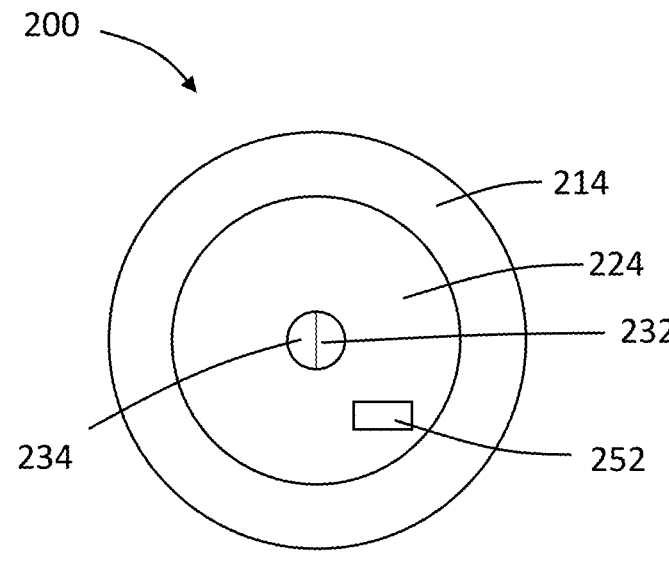

FIG. 20 is a schematic bottom view of an embodiment of an access port having an interconnect.

Figure 21:
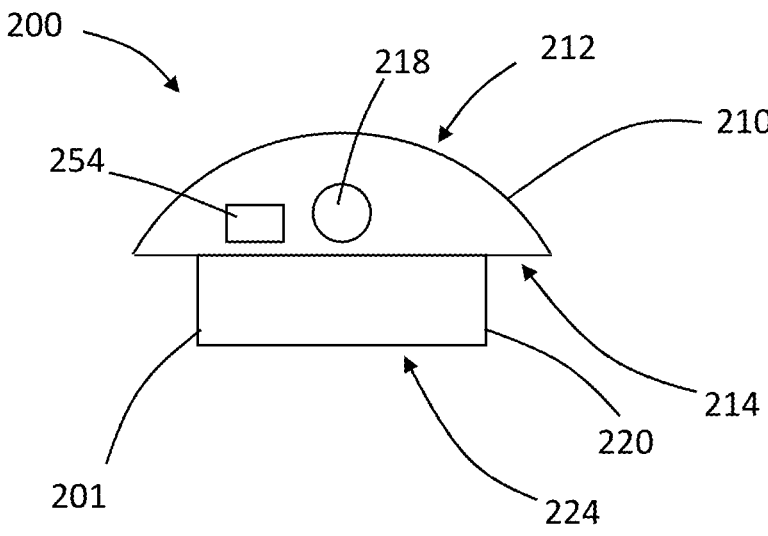

FIG. 21 is a schematic side view of an embodiment of an access port having an interconnect.

Figure 22:
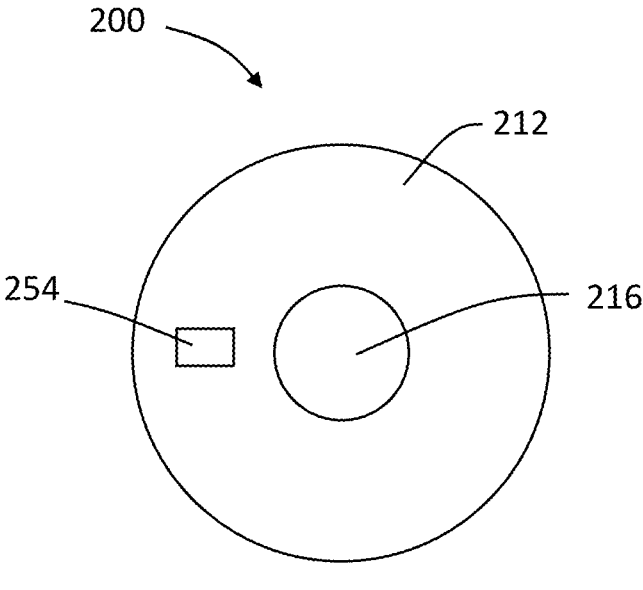

FIG. 22 is a schematic top view of an embodiment of an access port having an interconnect.

Figure 23:
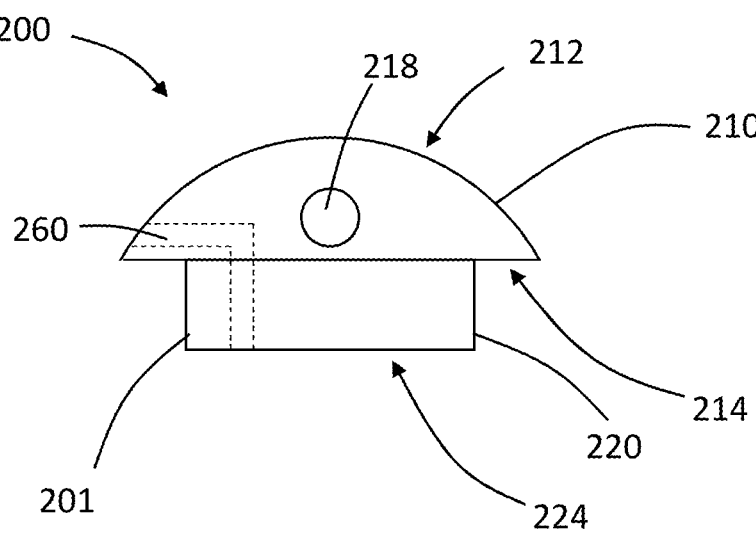

FIG. 23 is a schematic side view of an embodiment of an access port having a passageway.

Figure 24:
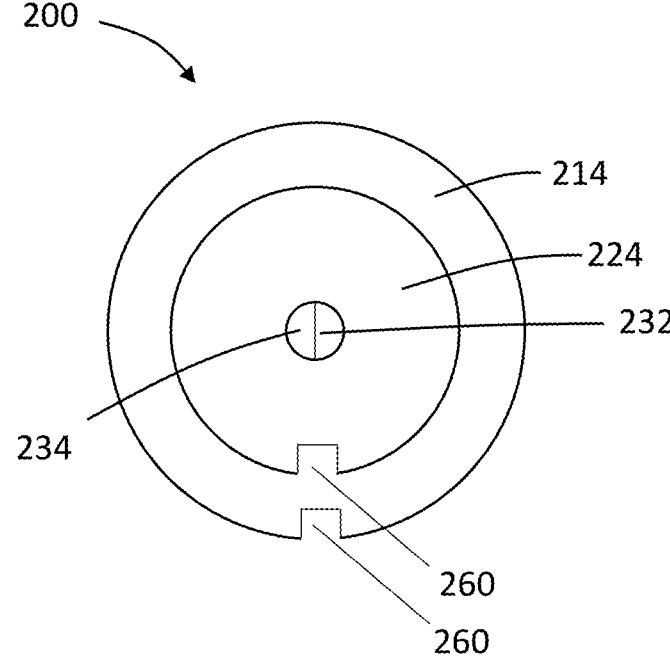

FIG. 24 is a schematic bottom view of an embodiment of an access port having a passageway.

Figure 25:
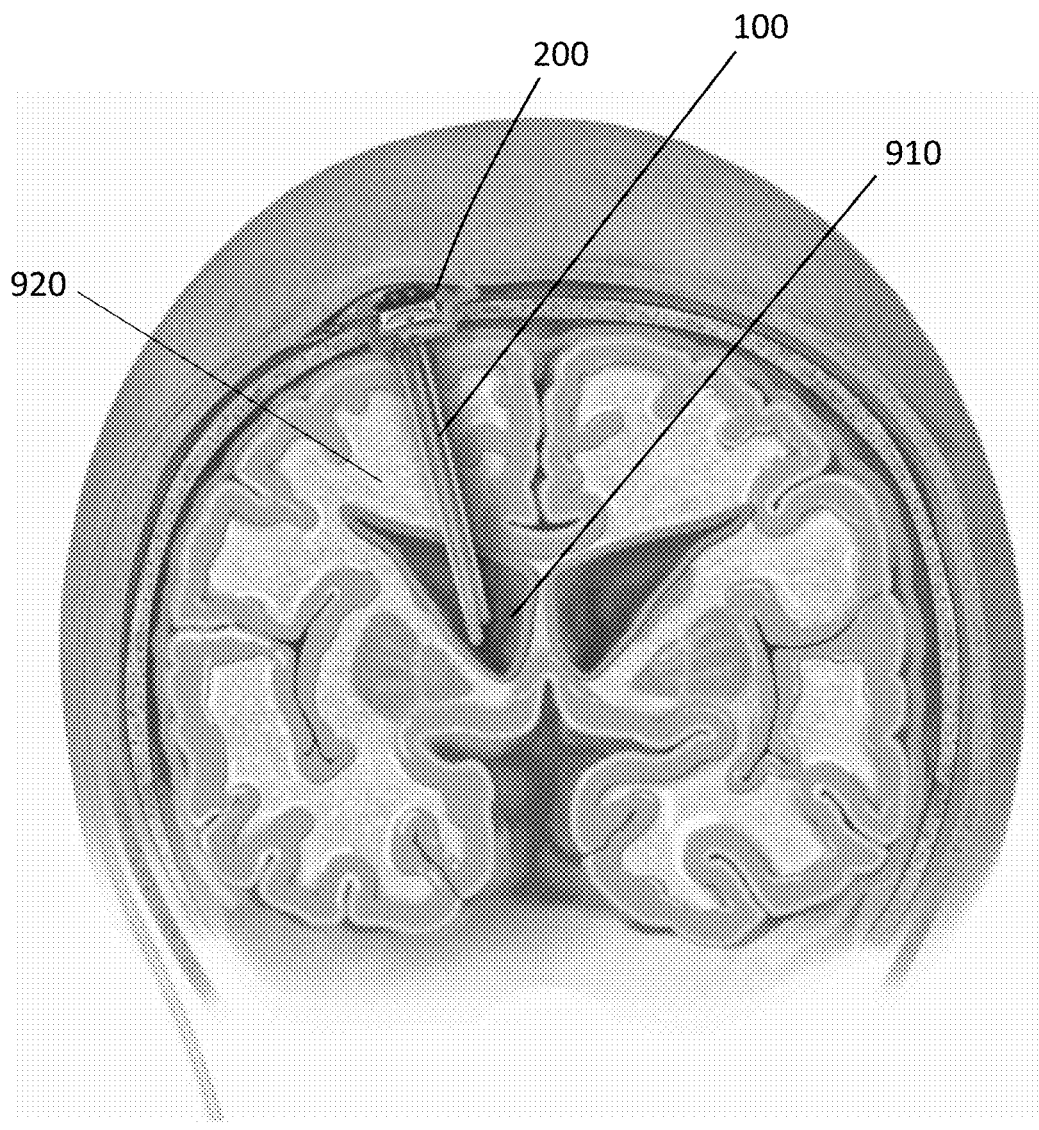

FIG. 25 is a schematic sectional view illustrating an embodiment of an access port and a catheter implanted in a subject.

Figure 26:
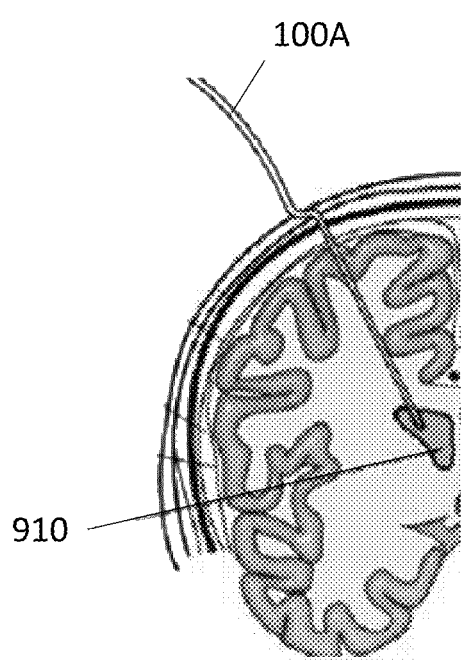

FIG. 26 is a schematic sectional view illustrating embodiment of an external ventricular drainage catheter and an intraparenchymal catheter implanted in a subject.

Figure 27A:
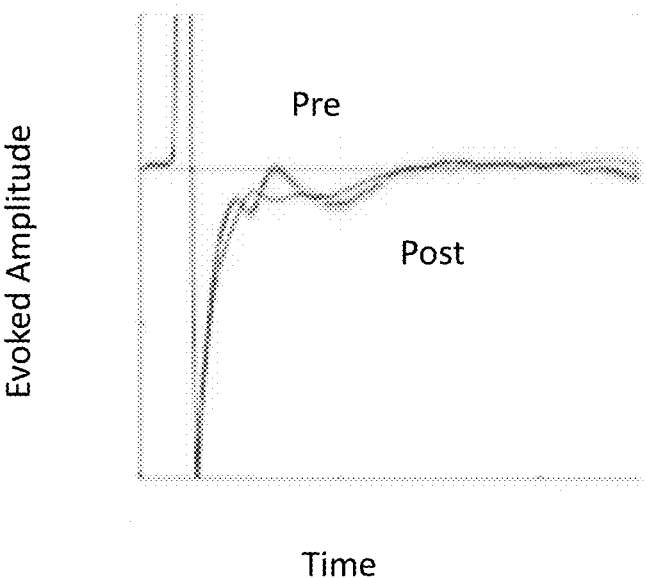
Figure 27B:
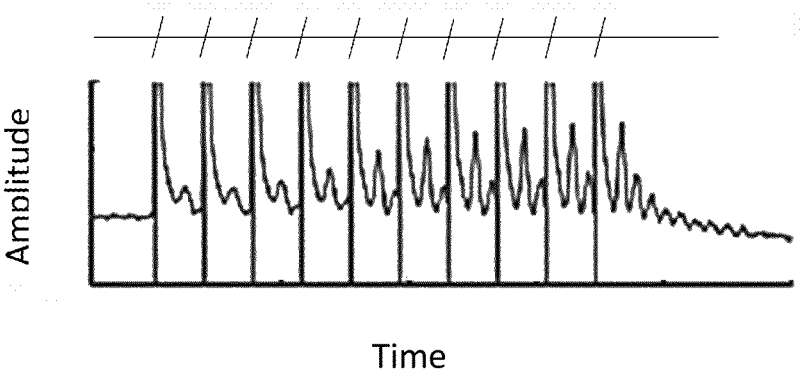

FIG. 27A and FIG. 27B show graphs illustrating evoked responses in the brain. FIG. 27A) Evoked responses were averaged over 30 seconds prior to (red) and after (blue) application of high frequency stimulation in the Anterior nucleus of the thalamus with parameters of 120 Hz, 2.5V and 300 microsecond duration. FIG. 27B) Evoked responses are used to detect the correct placement of DBS leads in Parkinson's. The evoked response seen in this figure is only observed in the subthalamic nucleus (STN) and disappears when the electrodes are placed in surrounding regions.

Figure 28:
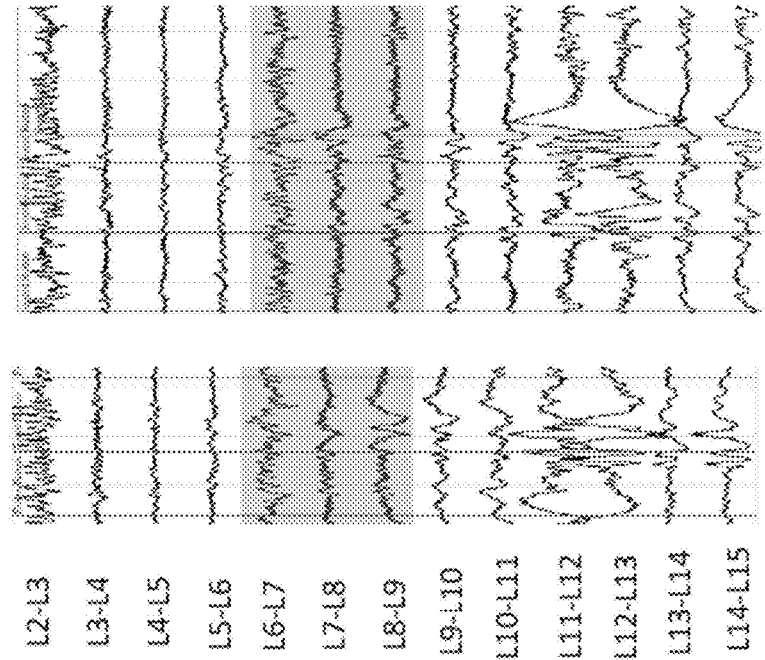
Figure 28:
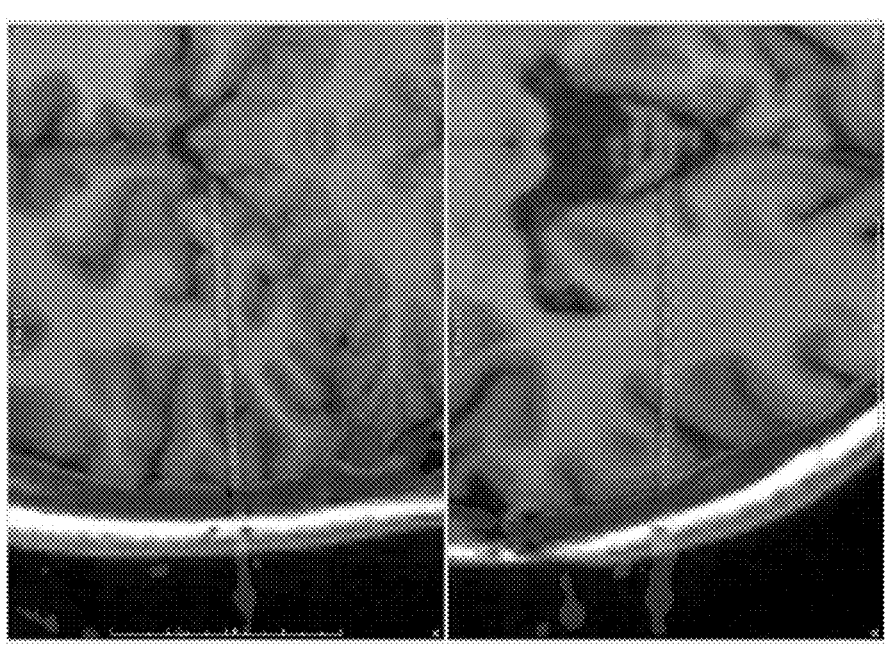

FIG. 28 are coronal and axial views of a catheter having a distal tip in a lateral ventricle and electrodes in white matter. Acute EEG recordings are shown on the right with numbering on electrodes corresponding to numbering on recording.

Figure 29:
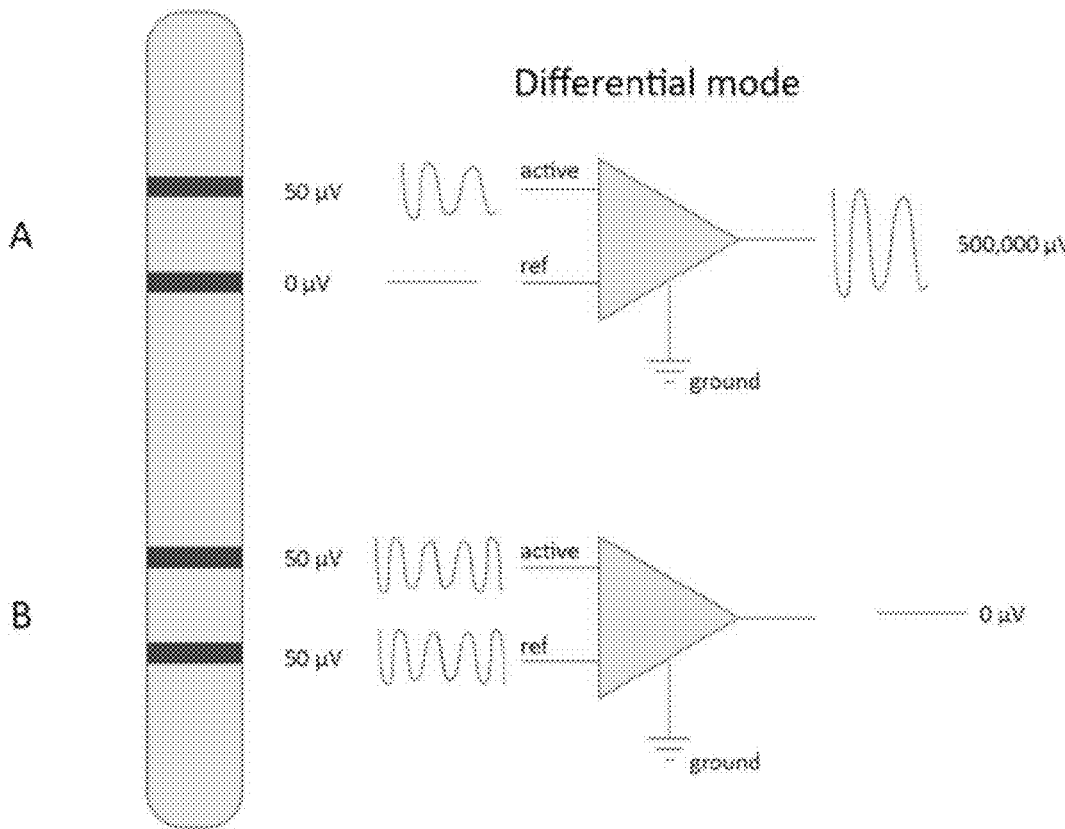

FIG. 29 is a schematic illustration of electrodes and signals in differential mode.

Figure 30:
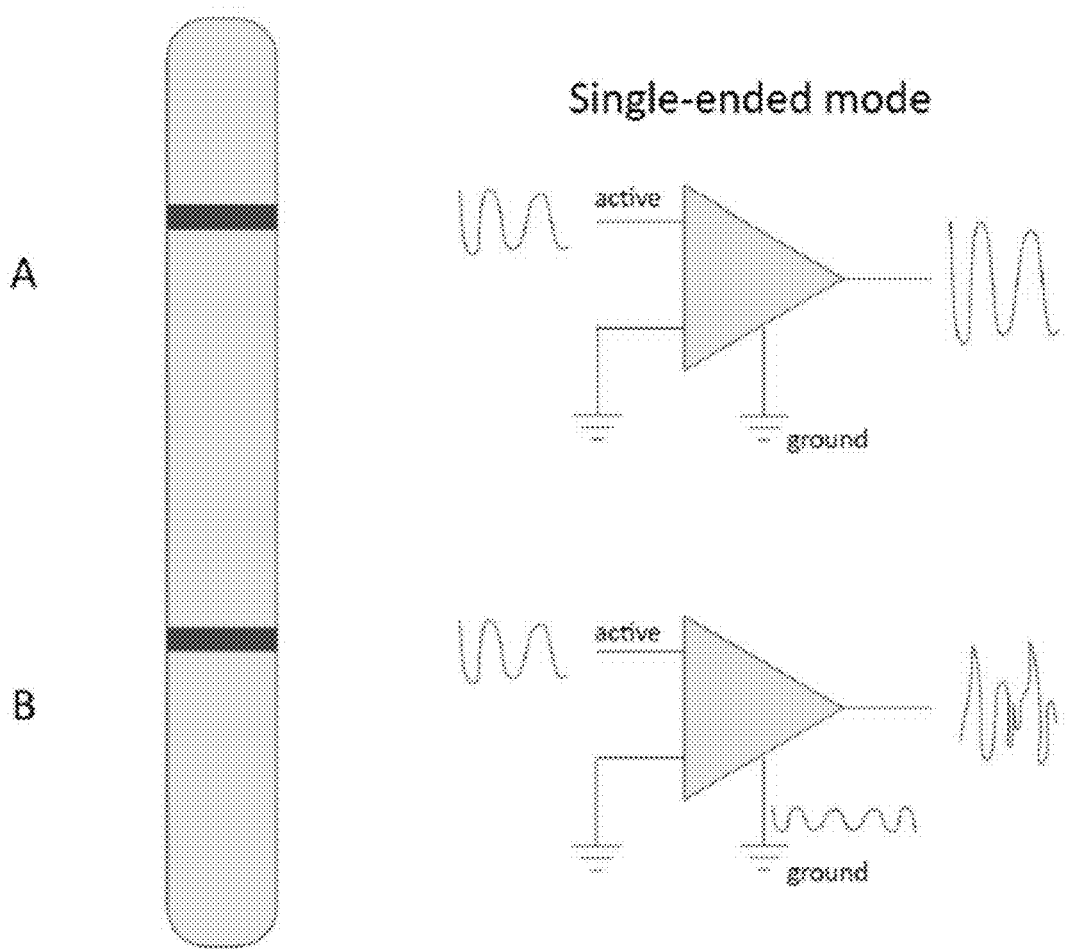

FIG. 30 is a schematic illustration of electrodes and signals in referential mode.

Figure 31:
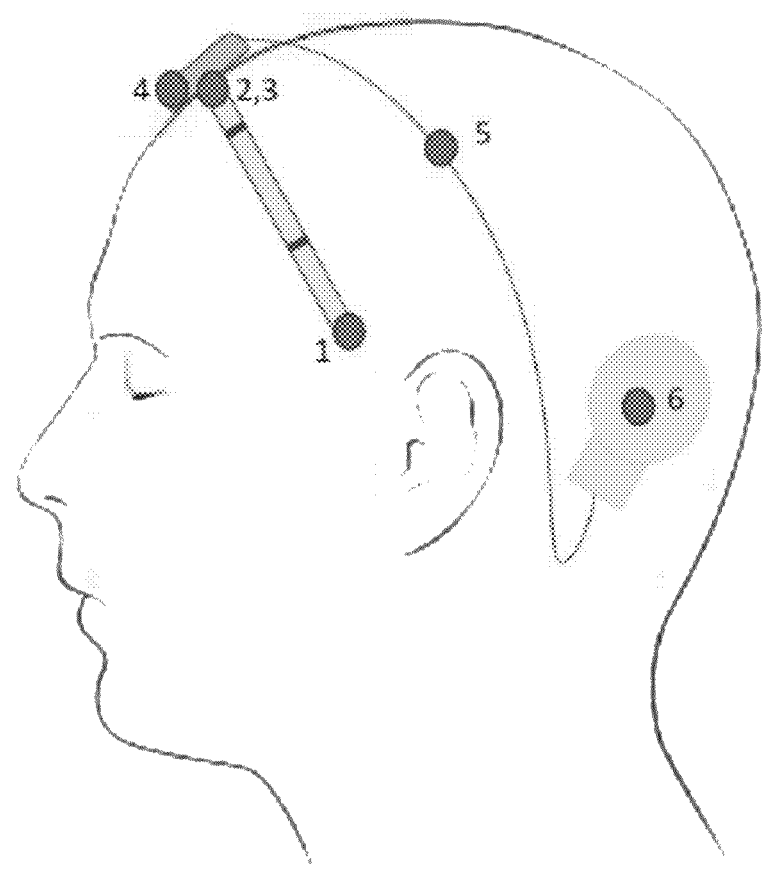

FIG. 31 is a schematic illustration of ground electrode placement that were evaluated.

8

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

Like numbers used in the figures refer to like components and steps. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components

DETAILED DESCRIPTION

The present disclosure relates to, among other things, devices and systems that include catheters for delivering therapeutic agents to a cerebrospinal fluid (CSF)-containing space of a subject or withdrawing CSF from the CSF-containing space and that include an electrode configured to be positioned white or grey matter of the brain. The electrodes may record electrical signals from the white matter or the grey matter. Preferably the electrode records the electrical signals from the white matter.

The electrode may be positioned relative to the catheter such that implanting the catheter so that the catheter may deliver fluid to, or withdraw fluid from, the CSF-containing space causes the electrode to be positioned in the white matter or the grey matter of the brain of the subject. The catheter may comprise the electrode or a lead may comprise the electrode. The lead may be secured relative to the catheter such that implanting the catheter results in the electrode being positioned in the white or grey matter.

High quality electrical signals relating to brain activity may be obtained by electrodes positioned in the white or grey matter, as opposed to on an external surface of the scalp. White matter of the brain is composed mainly of long-range myelinated axons, and serves as a preferred target for monitoring general electrical activity of the brain. The electrodes in the white matter may capture electrical activity associated with general brain state rather than merely capturing signals localized to small regions of the brain. The high-quality brain activity signals recorded by electrodes in white matter may facilitate interpretation, processing, and analysis of the signals, which may be used for any suitable reason. Grey matter of the brain is composed mainly of neuronal cell bodies. The electrodes in grey matter may primarily capture local field potentials, or electrical activity associated with local regions of brain. Recording activity within confined brain regions, or interactions between two or more grey matter regions may facilitate interpretation, processing, and analysis of the signals, which may be used for any suitable reason.

Simply capturing the recorded electrical signals provides a substantial advantage relative to current therapies that deliver therapeutic fluid directly to the brain or withdraw CSF from the brain, because such current therapies do not provide a mechanism for capturing such electrical signals. The recorded electrical signals may provide meaningful insight into brain states of subjects suffering from diseases of the brain that are being treated with therapeutic fluid or CSF drainage. Such brain states are not very well understood. Capturing the recorded electrical signals in subjects receiving treatment via a catheter placed in the brain without additional substantial surgical complexity or invasiveness may provide meaningful advancement in the understanding of brain states in general and brain states of patients suffering from brain diseases in particular.

The recorded electrical signals may be used to understand a current brain state or to predict a future brain state. Preferably, the electrical signals may be employed to modify and improve the therapeutic fluid delivery therapy or CSF drainage therapy. For example, the rate of infusion of therapeutic fluid may be adjusted based on data regarding the recoded electrical signals.

The devices, systems, and methods described herein may be employed in any suitable subject suffering from a brain disease. Non-limiting examples of diseases for which placement of a catheter in a brain may be warranted include Parkinson's disease, Alzheimer's disease, dementia, Amyotrophic Lateral Sclerosis, Huntington's disease, lysosomal storage diseases, post-traumatic stress disorder, anxiety, depression, brain tumors, autism, autism spectrum disorder, traumatic brain injury, closed head injury, spinal cord injury, stroke, multiple sclerosis, schizophrenia, anxiety, and epilepsy.

Any catheter that may be placed into a CSF-containing space of a subject for delivering fluid to, or withdrawing fluid from, the CSF-containing space may be used or modified in accordance with the teachings presented herein. Examples of such catheters include catheters associated with implantable infusion devices, CSF shunt or drainage catheters, catheters associated with Ommaya reservoirs or Rickman reservoirs, catheters associated with any suitable access port, and the like.

A catheter as described herein includes a proximal end, a distal end, a distal end portion including and in proximity to the distal end, and at least one lumen extending from the proximal end to the distal end portion. Preferably, the distal end is placed in a CSF-containing space. For purposes of differentiation from other catheters that may be described herein, a catheter configured for positioning of a distal end in a CSF-containing space will be referred herein as a CSF catheter.

CSF exits the foramen of Magendie and Luschka to flow around the brainstem and cerebellum. CSF flows within the subarachnoid space. CSF is produced in the ventricular system of the brain and communicates freely with the subarachnoid space via the foramen of Magendie and Luschka. The distal end of the catheter may be placed anywhere that the CSF is accessible. For example, the distal end of the catheter may be placed in communication with a *Cisterna magna*, a subarachnoid space, an intrathecal space, or a cerebral ventricle. Preferably, the distal end is placed in a cerebral ventricle. Preferably, the cerebral ventricle is a lateral cerebral ventricle.

The CSF catheter may be modified or adapted to include one or more recording electrodes as described herein. The one or more electrodes may be positioned on the CSF catheter a distance from the distal end such that the one or more electrodes would be placed in contact with white or grey matter of the brain if the distal end of the CSF catheter were at a suitable target location of the brain for therapeutic fluid delivery or CSF withdrawal (e.g., a CSF-containing space).

A lead that is separate from the CSF catheter may comprise the one or more electrodes. The lead may be coupled to the CSF catheter such that at least a portion of the lead is fixed relative to the CSF catheter. The lead may be fixed relative to the CSF catheter such that one or more electrodes of the lead may be positioned a distance from the distal end of the CSF catheter such that an electrode would be placed in contact with white or grey matter of the brain if the distal end of the CSF catheter were at a suitable target location of the brain for therapeutic fluid delivery or CSF withdrawal (e.g., a CSF containing space). For purposes of differentiation from other leads that may be described herein, a lead having an electrode configured to be positioned in white or grey matter of a brain of a subject will be referred herein as a brain lead.

The brain lead may be coupled to the catheter in any suitable manner. In some embodiments, the brain lead is coupled relative to the CSF catheter at the distal end portion of the CSF catheter, a mid-portion of the CSF catheter, and/or in proximity to the proximal end of the CSF catheter. Preferably, the brain lead is coupled relative to the CSF catheter at the distal end portion of the CSF catheter. Preferably, a distal portion of the brain lead is coupled to the distal end portion of the CSF catheter. By coupling a distal portion of the brain lead to a distal end portion of the CSF catheter, the distal portion of the brain lead may be pulled through brain tissue as the distal end portion of the CSF catheter is implanted and positioned in the CSF-containing space of the subject. Alternatively, a single implant procedure, e.g., implantation of the CSF catheter, results in implantation of both the CSF catheter and the brain lead.

In some embodiments, the brain lead is secured relative to the CSF catheter along a substantial length of the catheter or at multiple locations relative the CSF catheter. For example, the brain lead may be secured relative to the catheter over 50 percent or more of the length of the catheter, over 60 percent or more of the length of the catheter, over 70 percent or more of the length of the catheter, over 80 percent or more of the length of the catheter, or over 90 percent or more of the length of the catheter.

The brain lead may be secured relative to the catheter with adhesive, by bonding, via mechanical fixation, a combination thereof, or in any other suitable manner. In some embodiments, the brain lead is secured relative to the CSF catheter with a sleeve. The sleeve may be disposed over the brain lead and the CSF catheter. The sleeve may be elastomeric. The sleeve may be configured to press the brain lead against the CSF catheter when the sleeve is disposed over the CSF catheter. The sleeve may comprise windows configured to be positioned, or positioned, over the electrodes.

In some embodiments, a body of the CSF catheter defines an exterior groove configured to receive the brain lead. The groove may be configured to receive the brain lead via snap fit. In some embodiments, the CSF catheter comprises a groove and a sleeve, such an elastomeric sleeve, is placed about the brain lead and the CSF catheter to retain the brain lead in the groove of the CSF catheter.

A system or device as described herein may comprise a snap fit connector. The snap fit connector may engage one or both of the brain lead and the CSF catheter via snap fit engagement.

In some embodiments, the brain lead may be a currently available deep brain stimulation lead or may be a modified version of a deep brain stimulation lead. Currently available deep brain stimulation leads are available from Medtronic, Inc., Boston Scientific, Inc., and other manufacturers.

Preferably, the brain lead is coupled to the CSF catheter by a manufacturer. However, the brain lead may be coupled to the CSF catheter prior to implantation by, for example, a healthcare provider such as a surgeon. In such embodiments, the CSF catheter, the brain lead, or both the CSF catheter and the brain lead may comprise markings to facilitate proper alignment of the brain lead relative to the CSF catheter to ensure that, when the distal end of the CSF catheter is positioned in the CSF-containing space, the electrodes of the brain lead will be positioned in the white or grey matter.

The one or more electrodes, whether on the CSF catheter or a brain lead fixed relative to the CSF catheter, may be positioned any suitable distance from the distal end of the CSF catheter, depending in which CSF-containing space the distal end is placed. For example, at least one of the one or more electrodes may be positioned from about 0.5 centimeters to about 6 centimeters from a distal end of the CSF catheter, such as from about 1 centimeter to about 5 centimeters, or from about 2 centimeters to about 6 centimeters from the distal end of the CSF catheter.

The CSF catheter, or the brain lead that may be fixed relative to the CSF catheter, may comprise any suitable number of electrodes, such from about 1 electrode to about 64 electrodes. For example, the CSF catheter or the brain lead may contain 2 to 32 electrodes, such 2 to 16 electrodes, or 2 to 10 electrodes.

The electrodes may be longitudinally spaced relative to the CSF catheter at any suitable distance or interval. The electrodes may be evenly spaced or unevenly spaced. Preferably, at least some of the electrodes are evenly spaced. That is, the spacing between the electrodes relative to the length of the CSF catheter is preferably the same or substantially the same. As used herein, "substantially the same," in the context of electrode spacing means that distances do not vary by more than 10%, preferably by not more than 5%.

The spacing between electrodes may vary depending on electrode width, number of electrodes, and desired distance that the electrodes span. The electrodes may span any suitable distance relative to the length of the CSF catheter. For example, the electrodes may span a length of about 5 centimeters, such as about 4 centimeters.

The electrodes may have any suitable width. The electrodes may have the same or different widths. Preferably, the electrodes have the same width. As an example, the electrodes may have a width of from about 0.5 millimeters to about 2 millimeters, such as from about 0.7 millimeters to about 1.5 millimeters.

In some embodiments, all the electrodes are positioned such that they will be placed in white or grey matter of the brain when implanted. However, it is not necessary that all the electrodes be placed in the white or grey matter. If an electrode is not placed in white or grey matter, the recording from that electrode may continue to be captured and potentially ultimately ignored. Alternatively, recording from that electrode may be inactivated.

Preferably, a majority of the electrodes are configured to be placed in white or grey matter when the catheter is implanted. Preferably, at least 70% of the electrodes are placed in white or grey matter when the catheter is implanted.

Preferably, at least two electrodes are configured to be placed in white or grey matter when the catheter is implanted. When multiple electrodes record signals from white or grey matter, coherent changes in activity between electrodes may be a powerful way to track more global changes. In some embodiments, the excitable state of a neural network is determined by monitoring a small neuronal population. The more excitable the small neuronal population, the higher the probability for activity to propagate throughout the network causing an 'avalanche' of activity. Such monitoring may be valuable for general brain state monitoring and may be particularly valuable for monitoring a brain state to predict a seizure.

The electrodes and associated signal processing apparatus may be configured in any suitable manner. For example, the electrodes and associated signal apparatus may be configured in differential mode or referential mode.

In differential mode, the system comprises an active electrode, a reference electrode, and a ground. The signal difference between an active electrode and a reference electrode may be amplified. The reference electrode may be a common reference for more than one active electrode. The reference electrode is preferably positioned a substantial distance from an active electrode and from the ground. The catheter or brain lead comprises the active electrode. The catheter or brain lead may comprise the reference electrode. The reference electrode may be separate from the catheter or brain lead. In differential mode, the system may be configured to detect small differences between electrode pairs and may be less likely to be affected by large artifacts originating near the ground electrode. However, the system may not be particularly effective at detecting larger common signals.

Preferably, the system is configured to detect larger common signals. Larger common signals may be associated with an overall brain state or with a seizure.

To detect larger common signals, the system may be configured in referential mode, which may also be referred to as single-ended mode. Referential mode may use a single active electrode per amplifier. There may be more than one active electrode. In referential mode, the output of the active electrode is amplified relative to the ground electrode, as opposed to the reference electrode in differential mode. The ground is preferably placed a substantial distance from the active electrode, which may result in amplification of signals that affect larger parts of the brain. While being effective at detecting larger common signals, referential mode may be sensitive to artifacts. Proper placement of the ground electrode may mitigate some issues associated with artifacts.

In referential mode, the catheter or the brain lead associated with the catheter comprises the active electrode. The catheter or the brain lead associated with the catheter may comprise the ground electrode. The ground electrode may be separate from the catheter or brain lead. If the catheter or associated brain lead comprises the ground electrode, the ground electrode may be positioned near the distal end of the catheter, near a mid-portion of the catheter, or near the proximal end of the catheter. Preferably, the ground electrode is placed near the proximal end of the catheter.

The electrodes may be positioned on the catheter or on the brain lead associated with the catheter in any suitable manner. For example, the electrodes may extend around the circumference of the catheter or brain lead or may extend less than all the way around the circumference of the catheter or brain lead. For example, the electrodes may radially extend around the catheter or brain lead from about 90 degrees to about 270 degrees, such as from about 120 degrees to about 240 degrees, from about 150 degrees to about 210 degrees, or about 180 degrees. Each electrode may extend around the catheter or brain lead the same or a different amount. Preferably, each electrode extends around the catheter, or the brain lead, the same amount. Preferably, each electrode extends radially around the catheter, or the brain lead, about 180 degrees, or about half-way around the circumference of the catheter or the brain lead. In some embodiments, every other electrode along the length of the catheter or the brain lead faces in substantially the same direction. Each subsequent electrode may face a substantially opposite direction as the adjacent electrode.

The electrodes may be made of any suitable material. Suitable materials for implantable electrodes are well-known to those of skill in the art. Materials suitable for deep brain stimulation electrodes are suitable materials for electrodes of the catheters described herein. In some embodiments, the electrodes are made from platinum or a platinum iridium alloy.

The electrodes may have any suitable thickness. For example, the electrodes may have a thickness from about 100 microns to about 0.3 millimeters, such as from about 200 microns to about 0.2 millimeters. The electrodes may be formed from a foil.

Each electrode may be discretely electrically coupled to one or more electrical contacts. An electrical interconnect may comprise the contacts. For purposes of differentiating from other electrical interconnects described herein, an electrical interconnect that comprises a contact that is electrically coupled with an electrode configured to be placed in white or grey matter of a subject's brain is referred to herein as a brain signal electrical interconnect.

The brain signal electrical interconnect may allow for electrical connection with another device or cable for connection to another device. In some embodiments, a proximal end portion of the catheter forms the electrical interconnect, with the contact being disposed on, or exposed through, an external surface of the catheter. In some embodiments, the electrical interconnect is physically separate from the catheter. In some embodiments, a proximal end portion of the brain lead forms the electrical interconnect, with the contact being disposed on, or exposed through, an external surface of the brain lead.

Regardless of the location of the brain signal electrical interconnect, conductors may electrically couple the electrodes to the contact. Each electrode may be electrically coupled to a discrete contact by a conductor. If the proximal end portion of the catheter serves as the electrical interconnect, the conductors may extend within a body of the catheter, within a lumen of the catheter, or along an external surface of the catheter. If the proximal end portion of the brain lead serves as the electrical interconnect, the conductors preferably extend within a body of the brain lead.

If the electrical interconnect is physically separate from the catheter (and the catheter comprises the electrodes), the conductors may run along a length of the catheter for a distance and branch off from the catheter as a cable through which the conductors extend to the electrical interconnect. The conductors may extend within a body of the catheter, within a lumen of the catheter, or along an external surface of the catheter before branching off from the catheter. The wires may be braided or twisted in the cable to improve flexibility, strength, or flexibility and strength.

Referring now to FIGS. 1-4, embodiments of CSF catheters 100 are shown. The CSF catheters 100 have a proximal end 120 a distal end 111 at a distal end portion 110, and a lumen 172 extending from the proximal end 120 to the distal end 111. In some embodiments (not shown) the lumen 172 does not extend to the distal end 111, but rather the distal end portion 110 comprises openings (not shown) in communication with the lumen 172, 174 through which fluid may flow. The depicted CSF catheter 100 includes two lumens 172, 174, separated by a wall 180 that extends the length of the CSF catheter 100. However, the catheter 100 may have any suitable number of lumens.

The CSF catheter 100 has electrodes 130 positioned along a length of the catheter beginning at a distance D1 from the distal tip 111, such as about 0.5 centimeters to about 2 centimeters. The electrodes 130 may span a distance D2 along the length of the catheter 100, such as about 3 centimeters to about 5 centimeters.

Figure 1:
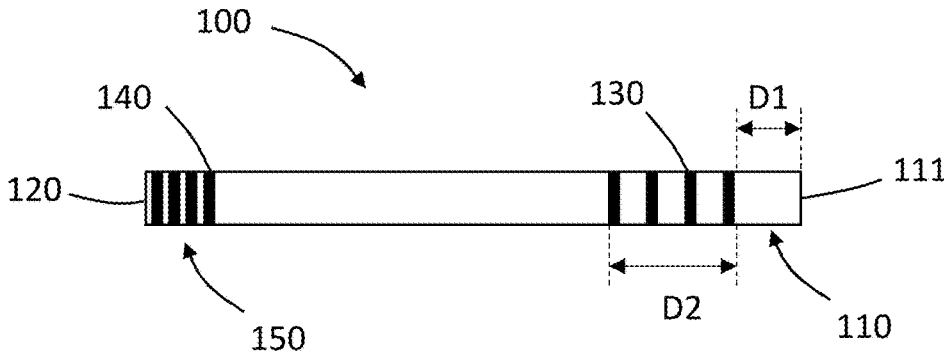
FIG. 1 is a schematic side view of an embodiment of catheter.

In the embodiment depicted in FIG. 1, contacts 140 are positioned around the circumference of the CSF catheter 100 near the proximal end 120, forming an electrical interconnect 150.

Figure 2:
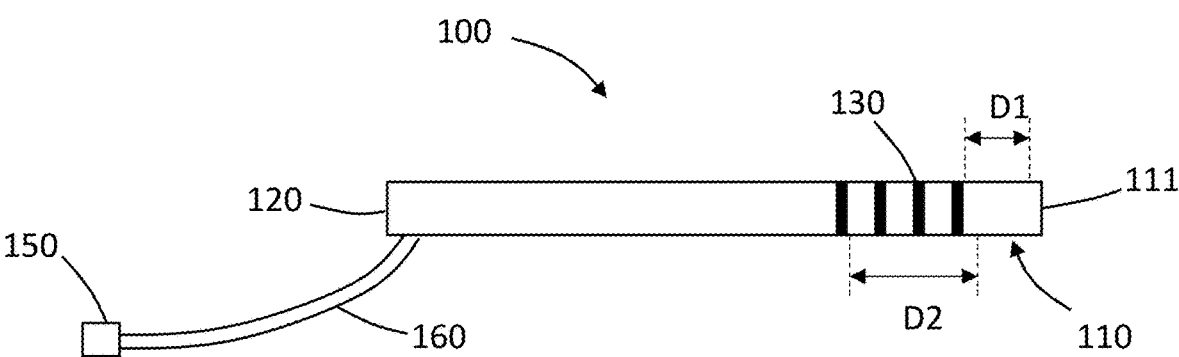
FIG. 2 is a schematic side view of an embodiment of catheter.
Figure 3:
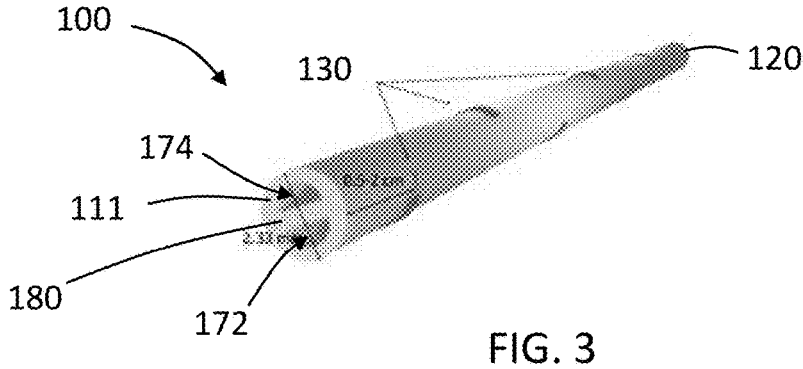
FIG. 3 is a schematic perspective view of an embodiment of a catheter.
Figure 4:
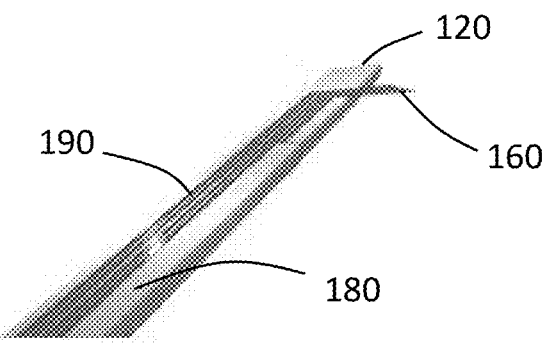
FIG. 4 is a schematic perspective cut-away view of an embodiment of a portion of a catheter.

In the embodiment depicted in FIG. 2, the interconnect 150 is physically separate from the CSF catheter 100. A cable 160 containing conductors 190 (as shown in FIG. 4) extends to the interconnect 150.

The conductors 190 electrically couple the electrodes 130 to the contacts 140 at the interconnect 150. In FIG. 4, the conductors 190 are shown running along the wall 180 separating the lumens and branching off the CSF catheter as a cable 160. However, the conductors 190 may run along the CSF catheter at any suitable location, such as along an exterior surface.

Referring now to FIGS. 5 to 10B, embodiments that include a CSF catheter 100, a brain lead 600, and/or a fixation element or means are shown. The brain lead 600 may be placed adjacent to the CSF catheter 100. The brain lead 600 may be coupled to the CSF catheter 100 such that when the distal end 111 of the CSF catheter 100 is positioned in a CSF-containing space of a subject, one or more electrodes 130 of the brain lead 600 are in contact with white or grey matter of the brain of the subject.

Electrodes 130 are positioned at a distal end portion 610 of the brain lead 600. The distal end 611 of the brain lead 600 may be positioned adjacent the distal end 111 of the CSF catheter 100 (as shown in FIG. 5) or may be positioned proximal to the distal end 111 of the CSF catheter 100 (as shown in FIG. 6).

Figures 5, 6:
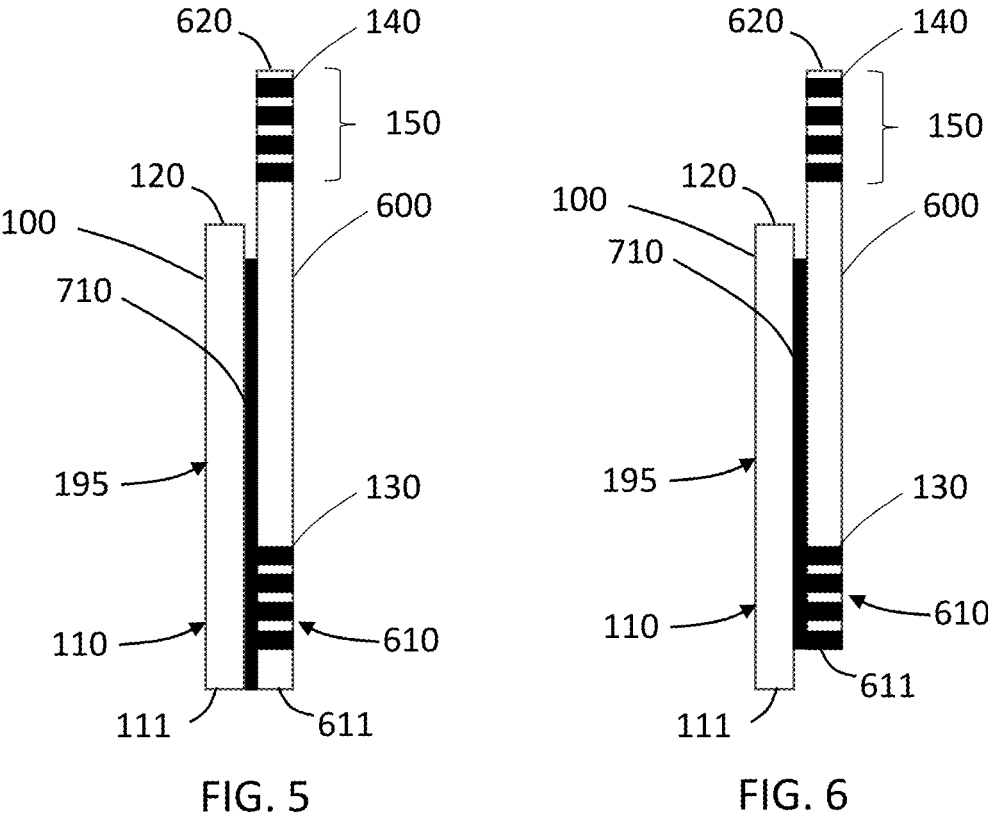
FIGS. 5-6 are schematic side views of embodiments of a lead coupled to a catheter via adhesive.

The brain lead 600 may be adhered to the CSF catheter 100 via adhesive 710 as shown in FIGS. 5-6. The adhesive 710 may be disposed in multiple locations along the CSF catheter 100 or may be disposed along a substantial portion of the CSF catheter 100 as shown in FIGS. 5-6. Preferably, the proximal end 120 of the CSF catheter 100 is not adhered to the brain lead 600 to facilitate connection to a catheter connector. This may also facilitate connection of the proximal end portion (in proximity to proximal end 620) of the lead to an interconnect to allow electrical connection between contacts 140 and a signal apparatus. The contacts 140 and body of the brain lead 600 may form an electrical interconnect 150 for electrically coupling to the signal apparatus interconnect or other suitable interconnect.

Figures 7A, 7B:
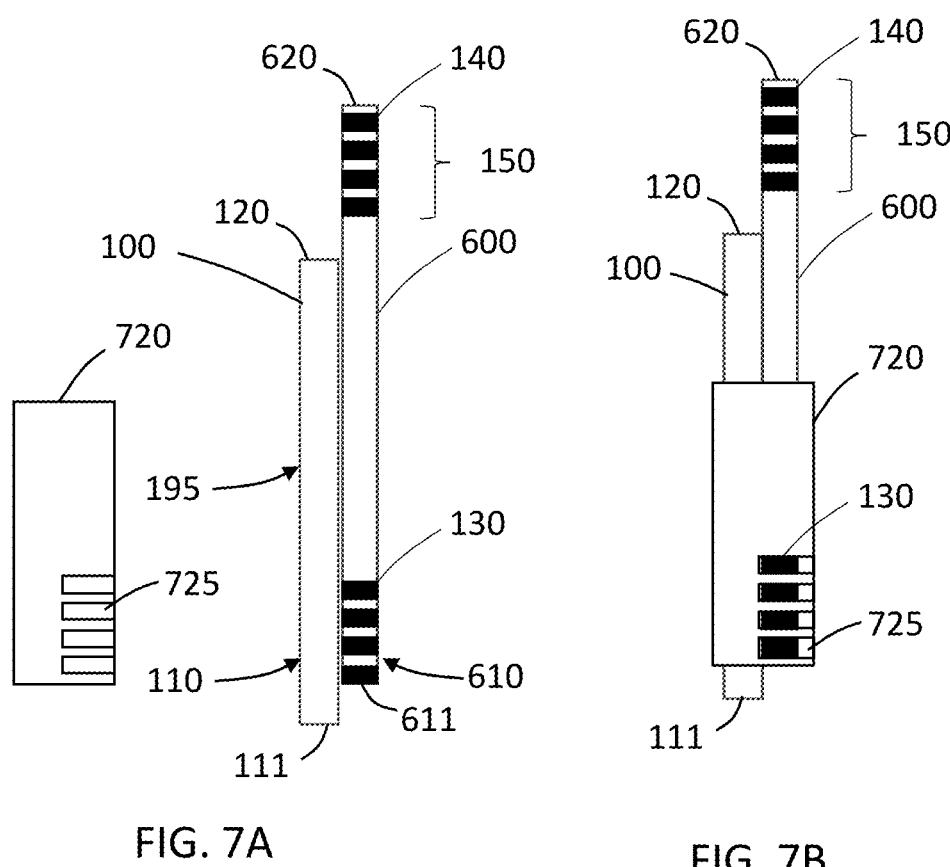
FIGS. 7A-B are schematic side views illustrating an embodiment of a lead, a catheter, and a sleeve configured to be (FIG. 7A) disposed about, or disposed about (FIG. 7B), the lead and the catheter.

FIGS. 7A-B illustrated a CSF catheter 100, a brain lead 600, and a sleeve 720. The sleeve 720 may be disposed about the brain lead 600 and CSF catheter 100 and may be configured to press the brain lead 600 against the CSF catheter 100. Preferably, the sleeve 720 is elastomeric. The sleeve 720 may define windows configured to be placed over electrodes 130. The windows 720 (lack of material) allow the electrodes 130 to electrically couple with, or electrically contact, the white or grey matter in which they are implanted. That is, the electrodes 130 may be exposed to the tissue through the windows 725.

While only one sleeve 720 is depicted in FIGS. 7A-B, more than one sleeve may be employed. The sleeve 720 may be disposed over any suitable portion or substantially all of the brain lead 600 and CSF catheter 600.

FIG. 8 illustrates a CSF catheter 100 having a body 198 having an exterior surface defining a groove 199 configured to receive a brain lead (not shown in FIG. 8). The groove may extend the length of CSF catheter 100 (from the proximal end 120 to the distal end 111) or any suitable portion of the length of the CSF catheter 100. The groove 199 or one or more portions thereof may be configured to engage the brain lead via snap fit engagement. In some embodiments, the brain lead is received by the groove 199 and a sleeve (not shown in FIG. 8) is disposed about the brain lead and the CSF catheter 100 to retain the brain lead in the groove 199.

FIG. 9 shows an embodiment of a snap fit connector 730 configured to receive a CSF catheter and a brain lead by snap fit engagement. The connector 730 comprises an opening 735 configured to engage the CSF catheter and an opening 739 configured to engage the brain lead. The connector 730 comprises deflectable elements 732, 736 that are configured to resiliently deflect as the CSF catheter or brain lead are inserted into openings 735, 739 and thus engage the CSF catheter and brain lead via snap fit engagement.

FIGS. 10A-B show an embodiment in which snap fit connectors 730A-C, which may be a snap fit connector as shown in FIG. 9, are used to fix a brain lead 600 relative to a CSF catheter 100. One or more snap fit connectors 730A-C(three depicted) may be used to engage the CSF catheter 100 and the brain lead 600. The snap fit connectors 730 may be formed of any suitable material. Preferably, the snap fit connectors 730 comprise a biocompatible hard plastic material. Examples of suitable biocompatible hard plastic materials included polyether ether ketone, polycarbonate, polypropylene, and the like.

Other suitable connectors may be formed from biocompatible hard plastics or biocompatible metallic materials.

The devices, systems, or devices and systems describe herein may include signal apparatus electrically coupled to the electrodes. For example, the signal apparatus may be electrically coupled to the electrodes via an electrical interconnect of, for example, a cable extending from the CSF catheter, at the proximal end portion of a catheter, or the proximal end portion of a brain lead associated with the CSF catheter. The signal apparatus may process, transmit, or process and transmit data regarding the signals recorded by the electrodes. The signal apparatus may comprise any suitable components, such as components configured to one or more of: amplify, digitize, filter, and transmit data regarding the electrical signals recorded by the electrodes. For example, the signal apparatus may comprise one or more of: an amplifier, an analog to digital converter, a band pass filter, an antenna, and a transmission coil.

The signal apparatus may be configured to sample the signals from the electrodes at any suitable frequency. For example, the signal apparatus may be configured to sample the signals at a frequency of about 100 hertz or greater, such as 1,000 Hertz or greater. Preferably, the signal apparatus is configured to sample the signals at a frequency of about 10,000 hertz or greater. The signal apparatus may process the signal at any suitable bit depth, 4 bits, 8 bits, 16 bits or greater.

The signal apparatus may be implanted in the patient at any suitable location. The signal apparatus may comprise a power source or may be wirelessly powered. If the signal apparatus is wirelessly powered, the signal apparatus preferably includes an inductive coil, solenoid, or other suitable components to be wirelessly powered by an external apparatus and to transmit data regarding the signals recorded by the electrodes to the external apparatus. The signal apparatus is preferably implanted at a location where it may inductively couple with the apparatus external. For example, the signal apparatus may be positioned under the scalp of the subject near an ear of the subject. Such positioning may allow the external apparatus to be comfortably worn on or around the ear of the subject to provide suitable inductive coupling to power the signal apparatus and to wirelessly transmit data regarding the signals recorded by the electrodes from the signal apparatus to the external apparatus. The external device may then transfer the data to the cloud or to another device, such as a smart phone, a personal computer, or the like, which may then transfer the data to a server, or the like.

In some embodiments, the CSF catheter or the brain lead associated with the CSF catheter comprises the signal apparatus.

In some embodiments, an implantable infusion device comprises the signal apparatus.

Referring now to FIGS. 11-14, various embodiments of CSF catheters 100 operably coupled to implantable infusion devices 400 are shown. In the depicted embodiments, the CSF catheters 100 comprise electrodes 130 for recording electrical signals in white matter. The electrodes 130 are electrically coupled to signal apparatus 300 configured to process, transmit, or process and transmit data regarding the electrical signals recorded by the electrodes 130. External apparatus 500 may be positioned relative to signal apparatus 300 such that the data may be transmitted wirelessly from the signal apparatus 30 to the external apparatus 500. The external apparatus 500 may be configured to wirelessly power the signal apparatus 300 in some embodiments.

For example and with reference to FIG. 11, the signal apparatus 300, which is coupled to electrodes 130 by conductors that run through cable 160 and through or along a portion of the CSF catheter 100, is implanted under the skin such that external apparatus 500 may wirelessly power and receive data from signal apparatus 300. For example and with reference to FIG. 12, the signal apparatus may be implanted under the subjects scalp near the ear. External apparatus 500 comprises an inductive coupling component 510 that may be positioned over the signal apparatus and comprises a processing component 520 operably coupled to the inductive coupling component 510. The processing component 520 may include, among other things, a rechargeable battery and a processor. The external apparatus 500 may transmit data received from signal apparatus 300, or a processed version thereof, to suitable secondary device, such as a smartphone, personal computer, tablet, modem, or the like through any suitable platform, such as low power Bluetooth. The secondary device may transmit data to the internet, where the data may be stored or retrieved by other computing devices as appropriate.

In the embodiment depicted in FIG. 13, an infusion catheter 410 extending from an implantable infusion device 400 to an access port 200 comprises the signal apparatus 300. The portion of the infusion catheter 410 comprising the signal apparatus 300 is preferably positioned at a location under the skin through which data regarding the signals recorded by the electrodes 130 may be transmitted to the external apparatus 500.

In the embodiment depicted in FIG. 14, the implantable infusion device 400 comprises the signal apparatus (not shown).

As indicated above, the CSF catheters described herein may be any suitable catheter, such as a catheter of an implantable infusion device, a catheter of a CSF shunt or drainage catheter, a catheter associated with an Ommaya or Rickman reservoir, or a catheter associated with an access port. For purposes of illustration, association of a CSF catheter with an access port will be described herein in more detail.

The devices, systems, or devices and systems described herein may include any suitable access port. The access port may be configured to be implanted below the scalp of the subject. The access port may comprise an opening configured to receive a needle inserted across the scalp of the subject. The access port may comprise a first catheter connector and a first fluid flow path extending from the opening to the first catheter connector. The proximal end of the catheter may be coupled to the first catheter connector such that the lumen of the catheter is placed in fluid communication with the first fluid flow path. The distal tip of the catheter may be implanted in a CSF-containing space of the brain of the subject such that the one or more electrodes are in the white matter.

A CSF catheter configured to couple to an access port implanted under the scalp may have any suitable length. Preferably, the length is sufficient to extend to a CSF-containing space, such as a cerebral ventricle. In some embodiments, the CSF catheter has a length from about 45 millimeters to about 80 millimeters. Preferably, the catheter has a length of about 60 millimeters to about 70 millimeters, more preferably from about 62 millimeters to about 68 millimeters within the cranium.

The needle may introduce fluid through a first fluid flow path of the access port and through the lumen of the catheter or may aspirate fluid from the CSF-containing space of the brain through the lumen of the catheter and the first fluid flow path.

At least a portion of the access port may be configured to be implanted in a burr hole in the skull of the subject, with a portion implanted above the skull.

The access port may comprise a second catheter connector and a second fluid flow path extending from the second catheter connector to the first catheter connector. In such embodiments, the CSF catheter may comprise a second lumen extending from the proximal end of the catheter to the distal end portion. When the proximal end of the CSF catheter is coupled to the first catheter connector, the second lumen may be placed in fluid communication with the second fluid flow path of the access port.

An implantable infusion device, a CSF drainage catheter, or the like may be operably coupled to the second fluid flow path of the access port via the second catheter connector. Any suitable implantable infusion device may be coupled to the second catheter connector. For example, the infusion device may be manually powered, electromechanically powered, chemically powered, or otherwise powered. In some examples, the infusion device may comprise a piston pump, a peristaltic pump, an osmotic pump, a plunger, or the like. Any suitable CSF drainage catheter may be coupled to the second catheter connector. For example, a distal portion of the CSF drainage catheter may be placed in a bladder or a peritoneal cavity or may extend external to the subject.

An access port having two isolated fluid flow paths as described above advantageously allows for therapeutic fluid to be continuously delivered, such as by an implantable infusion device, through the second fluid flow path while CSF is aspirated or another therapeutic fluid is delivered through the first fluid flow path. Similarly, if the second fluid flow path is used for CSF drainage, CSF may be aspirated, or a therapeutic fluid delivered, through the first fluid flow path without interrupting continuous CSF drainage through the second fluid flow path.

The second flow path may comprise a filter such as a microbial filter. A microbial filter may comprise a pore size of 0.45 microns or less, such as 0.22 microns or less or 0.2 microns or less. The first flow path preferably does not comprise a microbial filter. The second flow path may be used to sample CSF from the CSF-containing space of the subject. One purpose for sampling CSF is to determine whether an infection has occurred. If the first flow path comprises a microbial filter, an infectious microbe may be filtered (and not collected) and thus the presence of an infectious microbe may not be detected. In addition and over time, cells in the CSF and CSF proteins may accumulate on a microbial filter and may clog the filter. Accordingly, the first fluid flow path preferably does not comprise a microbial filter.

In embodiments where the cable carrying conductors that electrically couple the electrodes to the contacts of the interconnect branches off of the CSF catheter and the interconnect is physically separate from the CSF catheter or where a brain lead separate from the CSF catheter comprises the electrodes, the access port may define a passageway configured to receive the cable or lead. The passageway may extend from a bottom surface to a top surface or a side surface of the access port. In some embodiments, the passageway is of sufficiently large inner dimensions (e.g., width or diameter) to permit the interconnect of the cable or to permit the lead to be fed through the passageway. In some embodiments, the passageway may comprise a slot in an outer surface of the access port. The slot may be configured to receive the cable or lead.

In some embodiments, the access port comprises the electrical interconnect. For example, the electrical interconnect may be positioned at a top or side surface of the access port to facilitate connection with the signal apparatus or a lead extending to the signal apparatus. In such embodiments the CSF catheter, and brain lead if present, is preferably coupled to the access port by a manufacturer and the catheter, lead if present, and access port are constructed such that a portion of the cable or lead runs through the access port to the electrical interconnect.

In some embodiments, the access port comprises a first port interconnect configured to electrically couple to the electrical interconnect (e.g, of cable, proximal end portion of catheter, or proximal end portion of lead). The first port interconnect may be positioned at any suitable location of the access port, such as at a bottom surface of the access port. The access port may comprise a second port interconnect electrically coupled to the first port interconnect. The second port interconnect may be positioned at any suitable location of the access port. For example, the second port interconnect may be positioned at a top surface or side surface of the port or may extend from, or be tethered to, a top or side surface of the port.

The signal apparatus may be electrically coupled to the second port interconnect. For example, a signal apparatus lead having a lead interconnect may extend to the signal apparatus. The signal apparatus lead interconnect may be configured to electrically couple with the second port interconnect.

Additional details regarding suitable access ports (implantable cranial medical devices) and catheters that may be adapted for use herein are described in U.S. Provisional Patent Application No. 63/052,284, filed on 15 Jul. 2020, having a title of IMPLANTABLE CRANIAL MEDICAL DEVICE, naming Cerebral Therapeutics, Inc. as Applicant, and which provisional patent application is hereby incorporated herein by reference in its entirety to the extent that it does not conflict with the disclosure presented herein.

Reference is now made to FIGS. 15-17, which illustrate an example of an embodiment of an access port 200. The access port 200 comprises an upper flange portion 210 and a lower portion 220. The upper flange portion has a generally convex top surface 212 and a generally flat bottom surface 214. The upper flange portion 210 is configured to be positioned between a skull and a scalp of a subject when implanted, with the bottom surface 214 of the upper flange portion 210 configured to rest on a skull of a subject. The upper flange portion 210 has a height H_u and a width W_u. The height H_u of the upper flange portion 214 is sufficiently small to avoid skin erosion and substantial discomfort to the subject when implanted. The width W_u of the upper flange portion 214 is sufficiently large to rest on the skull around a burr hole.

The lower portion 220 has a bottom surface 224, a height H_l and a width W_l. The height H_l of the lower portion 220 is sufficiently small so that the bottom major surface 224 of the lower portion 220 does not extend substantially below the burr hole when implanted in a subject. Preferably, the bottom major surface 224 of lower portion 220 does not extend below the burr hole when implanted in a subject. The width W_l of the lower portion 220 is sufficiently small such that the lower portion 220 fits within the burr hole when implanted.

The upper flange portion 210 comprises a first opening 216 through which a needle may be inserted and a second catheter connector 218. The lower portion 220 has a first catheter connector defining a first opening 232 and a second opening 234. A first fluid flow path (not shown in FIGS. 15-17) extends within a housing 201 from the first opening 216 of the upper flange portion 210 to the first opening 232 of the lower portion 220. A second fluid flow path (not shown in FIGS. 15-17) extends within the housing 201 from the second catheter connector 218 of the upper flange portion 210 to the second opening 234 of the lower portion 220.

Reference is now made to FIG. 18, the first catheter connector 230 may include a slot 235 configured to receive a portion of a catheter that separates one lumen from another in a dual catheter. For example and with reference to FIG. 3, the wall 180 of the catheter 100 that separates the first lumen 172 from the second lumen 174 may be inserted into slot 235 of the first catheter connector 230 such that the first lumen 172 of the catheter 100 is placed in fluid communication with the first lumen 232 of the first catheter connector 230 and such that the second lumen 174 of the catheter 100 is placed in fluid communication with the second lumen 234 of the first catheter connector 230. FIG. 18 also illustrates an embodiment of a second catheter connector 218.

Referring now to FIG. 19, an alternative embodiment of a first catheter connector 230 is shown. As with the catheter connector 230 depicted in FIG. 18, the catheter connector 230 depicted in FIG. 19 includes a slot 230 separating extensions forming the first opening 232 and the second opening 234. The extensions comprise a barb feature configured to retain the catheter when inserted into the connector 230. The connector 230 also includes contacts 239 positioned within the receptacle such that when a catheter having proximal contacts is inserted into the receptacle to couple the catheter connector 230, the contacts 239 of the receptacle contact the proximal contacts of the catheter.

For example, if the proximal end 120 of the catheter 100 of FIG. 1 were inserted into the catheter connector of FIG. 19, the contacts 140 of the catheter 100 would contact and electrically couple with the contacts 239 of the receptacle. Thus, the catheter connector 230 depicted in FIG. 19 may also serve as an electrical interconnect. In such an embodiment, the proximal portion of the catheter may be stiffened and/or reinforced to facilitate insertion into the catheter connector. It will be understood that the catheter connector 239 depicted in FIG. 19 may include sealing elements (not shown) to prevent bodily fluid from shorting or otherwise interfering with the electrical contact.

Referring now to FIGS. 20-22, embodiments of access ports 200 having electrical interconnects are shown. The embodiment depicted in FIG. 20 corresponds to the embodiment depicted in FIG. 16. The embodiment depicted in FIG. 21 corresponds to the embodiment depicted in FIG. 15. The embodiment depicted in FIG. 22 corresponds to the embodiment depicted in FIG. 17. To the extent that a labeled component is not discussed regarding FIGS. 20-22, reference is made to the discussion above regarding FIGS. 15-17.

As shown in FIG. 20, the access port 200 may comprise a first port electrical interconnect 252 at the bottom major surface 224 of the access port 200. The first port electrical interconnect 252 may be configured to connect with an interconnect that is physically separate from a catheter (e.g., a cable or a lead). For example, the proximal end 120 of the catheter 100 of FIG. 2 may be coupled to the catheter connector to place a first lumen of the catheter 100 in fluid communication with the first opening 232 of the access port 200 and to place a second lumen of the catheter 100 in fluid communication with the second opening 234 of the access port 200. The interconnect 150 of FIG. 2 may be connected with the first port interconnect 252.

The access port 200 may include a second port interconnect 254 at a side surface (FIG. 21) or the top surface (FIG. 22) of the access port 200. The second port interconnect 254 may be electrically coupled to the first port interconnect 252 through conductors (not shown) running in through the access port. The second port interconnect 254 may be connected with a lead interconnect of a lead that is operably coupled to signal apparatus to place the signal electronics in electrical communication with the electrodes of the catheter.

Referring now to FIGS. 23-24, access ports 200 having passageways 260 for receiving cables (e.g. cable 160 of FIG. 2 or a brain lead) are shown. The embodiment depicted in FIG. 23 corresponds to the embodiment depicted in FIG. 15. The embodiment depicted in FIG. 24 corresponds to the embodiment depicted in FIG. 16. To the extent that a labeled component is not discussed regarding FIGS. 23-24, reference is made to the discussion above regarding FIGS. 15-16.

In the embodiment depicted in FIG. 23, the passageway 260 extends from the bottom major surface 224 of the access port 200 to the top surface 212 and exits towards the side of the access port 200. The inner dimensions (e.g., width or diameter) of the passageway 260 may be sufficiently large to allow an interconnect (e.g., interconnect 150 of FIG. 2) or brain lead to be fed through the passageway 260. Alternatively, a manufacturer may construct the access port 200 with the CSF catheter coupled to first catheter connector (not shown in FIG. 17) and the cable or lead fed through the passageway 260 such that the interconnect extends from the passageway 260 to the side of the port 200.

In the embodiment depicted in FIG. 24, the passageway 260 is a slot formed in an outer surface of the access port 200. The slot may extend through the lower portion and the upper flange portion of the port 200. The cable and interconnect or lead may be guided to be received in the slot 260 as the access port 200 and catheter are being implanted.

In the embodiments depicted in FIGS. 23-24, the access port 200 permits the cable and interconnect or lead to be positioned above the skull and under the scalp so that the signal apparatus may be easily connected.

In some embodiments (not shown), the interconnect (e.g., interconnect 150 shown in FIG. 2 or proximal end portion of a brain lead) is incorporated into a top or side surface of the access port.

Referring now to FIG. 25, a catheter 100 and access port 200 are shown implanted in a patient. The access port 200 is implanted under the scalp. A portion of the access port 200 is above the skull and a portion is in a burr hole. The catheter 100 extends from the access port 200 to a lateral ventricle 910. Electrodes (not shown) of the catheter 100 (or of a lead coupled to the catheter, not shown) are positioned in the white matter or grey of the brain 920. Preferably, the electrodes are positioned in the white matter.

Referring now to FIG. 26, an external ventricular drainage cranial catheter 100A is shown with its distal end implanted in a lateral ventricle 910. Electrodes (not shown) of the catheter 100A (or of a lead coupled to the catheter, not shown) are positioned in the white matter or grey of the brain. Preferably, the electrodes are positioned in the white matter. The CSF drainage catheter may be a ventriculoperitoneal shunt or other suitable CSF shunt.

While of skill in the art will readily understand methods that may be employed to the devices and systems described herein. A brief description of some of the methods contemplated herein are described below.

In some embodiments, a method comprises recording an electrical signal from white or grey matter of a brain of a subject and determining a brain state of the subject or predicting a future brain state of the subject based on the recorded electrical signal. Recording the electrical signal from the white or grey matter of the brain of the subject may comprise recording the signal from one or more recording electrodes positioned in the white or grey matter. The recording electrodes may be on a catheter configured to deliver fluid to, or withdraw fluid from, a brain of the subject or may be on a lead coupled to the catheter. The catheter may be configured to deliver fluid to, or withdraw fluid from, a brain of the subject. The catheter may be positioned to deliver fluid to, or withdraw fluid from, a CSF-containing space of the subject. The catheter may be positioned to deliver fluid to, or withdraw fluid from, a cerebral ventricle of the subject.

The method may comprise applying an electrical signal to the white or grey matter. Recording the electrical signal from the white or grey matter of the brain of the subject may comprise recording an electrical response evoked by the applied electrical signal. Monitoring an evoked response may advantageously reduce relatively high intrinsic noise that may be present when passively monitoring, which noise may occlude a desired signal. Active monitoring (i.e., recording an evoked response) may improve the signal to noise ratio relative to passive monitoring. The electrical signal may be applied at regular intervals and the changes in evoked response may be recorded.

FIGS. 27A-B are provided to illustrate the use of evoked response to determine brain state. Active brain responses can be obtained by stimulating the brain at regular intervals and recording the changes in evoked brain response. The morphology of the evoked response could be used to determine properties about the neural network being stimulated. FIG. 27A shows a schematic example where 2 Hz electrical stimulation is applied to the hippocampus for 30 sec prior to (Pre) and following (Post) high frequency (120 Hz) stimulation applied to the anterior nucleus in a patient with epilepsy. The morphology of the evoked response had two clear bumps, forming a sinewave-like shape. Following the high frequency electrical stimulation, the response flattens out. This indicates that the high frequency stimulation interfered with the brain's response and changed its excitability FIG. 27B shows another example where evoked responses are used to detect if an electrode has been correctly placed during implantation for Parkinson's disease. When stimulating the brain at 130 Hz, an evoked response is observed that increase in amplitude and then resonate at the termination of stimulation. This response is only observed when the electrodes are placed in the sub-thalamic nucleus and not in surrounding regions.

The method may comprise subjecting the subject to a provocation ("provoking the subject") and measuring a response to the provocation. For purposes of this disclosure, a measuring a response to a provocation will be referred to as measuring a "provoked response." A provocation may be a stimulus other than an electrical stimulus applied to the brain of a subject. A provocation may comprise, for example, a psychological or sensory stimulus associated with a disease from which the subject is at risk or is suffering. For example, the stimulus may be designed to treat or elicit a symptom of the disease. Examples of provocations include recall of a memory, an auditory stimulus, a visual stimulus, or a tactile stimulus.

As an example, a patient suffering from post-traumatic stress disorder (PTSD) may be asked to recall a traumatic memory, may be shown an image associated with a traumatic event, or the like. Electrical signals may be recorded by the one or more electrodes in the white or grey matter of the brain, and the provoked response may be monitored. The provoked response may be used to better understand changes in brain state or brain activity associated with the provocation. In some embodiments, delivery of therapeutic fluid through a lumen of the catheter may be altered based on the monitored provoked response.

As another example, a patient suffering from PTSD may undergo eye movement desensitization and reprocessing therapy (EMDR). EMDR is an interactive therapy in which a therapist directs the patient's eye movements while the patient is recalling traumatic event. Electrical signals may be recorded by the one or more electrodes in the white or grey matter of the brain, and the provoked response may be monitored. The provoked response may be used to better understand changes in brain state or brain activity associated with the provocation. In some embodiments, brain activity may be monitored when the subject recalls the traumatic event with or without concomitant eye movement. Insights may be gained regarding differences in brain state that may occur while the patient is undergoing EMDR relative to recalling a traumatic event. That is, EMDR may be an effective therapy for treating PTSD, but how such therapy affects the brain is not well understood. The methods and devices described herein may provide valuable insight into such therapies regardless of whether the therapies are directly associated with a therapy delivered through a lumen of a catheter as described herein.

As another example, a patient may be exposed to photic stimulation which may induce patients to have a seizure or manic electrophysiologic signature. The provoked response may be monitored, which may lead to better understanding neural links associated with such seizures and mania. Understanding these neural links can help develop therapies or use known therapies to modify progression of a manic prediction into mania and perform a rescue therapy.

In general, provocations may be used to identify electrical signals in the brain associated with the provoked response. Understanding such electrical signatures may facilitate improved therapy. By understanding the electrical signatures, brain activity events leading to such signatures may be determined, which may allow prediction of such events. By predicting such events, preventative therapy may be administered. Similarly, by understanding the nature of the signature electrical signal, and thus the ability to detect such signatures, recovery therapy may be administered more quickly following detection of a signature electrical signal.

In some embodiments, a method may comprise delivering fluid to, or withdrawing fluid from, a CSF-containing space of a brain of a subject, wherein the fluid is delivered or withdrawn through a first lumen of a catheter, the catheter comprising one or more electrodes positioned in white or grey matter of the brain or coupled to a lead comprising one or more electrodes positioned in white or grey matter of the brain. The method may also comprise recording an electrical signal from the white or grey matter via the one or more electrodes. The method may also comprise transmitting data regarding the recorded electrical signal to apparatus external to the subject. The method may comprise determining a brain state of the subject or predicting a future brain state of the subject based on the recorded electrical signal.

FIG. 28 shows an example of intracranial EEG recordings of the type that will be obtained by electrodes of the catheter. The left shows coronal and axial views of an electrode array in the white (L6-L9) and grey (L1-L5 and L10-L15) matter. Intracranial EEG recordings are shown on the right with numbering on electrodes corresponding to numbering on recording and the highlighted region showing white matter recordings. The signals represent changes in brain response as a subject performs a task (onset of task action is shown by red lines).

In some embodiments, a method includes monitoring the safety or effectiveness of the therapy delivered via a catheter or another therapy to which the subject is undergoing. Because the subject has a catheter comprising electrodes positioned to record electrical signals from white or grey matter implanted in their of the brain, the recorded electrical signals may be used to monitor any brain therapy that the subject is undergoing. Any procedure involving brain surgery presents risks. However, some procedures present more risk than others. For such risky procedures, monitoring safety may be particularly important. Safety may be monitored by monitoring electrical signals recorded by the one or more electrodes in the white or grey matter of the brain. For example, a recorded electrical signal having a signature associated with ischemia, necrosis, or other adverse event may be employed to alert a patient or health care provider to intervene. Preferably, the electrical signature may be detected before the subject presents with typically diagnosable symptoms, such as altered level of consciousness or focal neurological defect.

As an example, induced hypervolemia, hemodilution, and hypertension therapy ("triple H") therapy may be effective but may present risks. Triple H therapy may be used to treat cerebral vasospasm after subarachnoid hemorrhage. Although Triple H therapy has gained widespread acceptance, some still question its efficacy and significant morbidity remains. Use of a catheter having electrodes, or coupled to a lead having electrodes, positioned in the white or grey matter as described herein may allow for monitoring of brain activity of a subject undergoing triple H therapy. The monitored activity may be used not only to determine whether triple H therapy is effective but also to determine if the therapy is safe. If brain signatures predictive of an adverse event are detected, medical intervention may occur.

In some embodiments, a method comprises delivering a therapeutic fluid to a central nervous system (CNS) of a subject suffering from or at risk of a CNS disease, and recording an electrical signal from white or grey matter of a brain of the subject. The therapeutic fluid may be delivered via a CSF catheter. The electrical signal may be recorded from an electrode of the CSF catheter or from an electrode of a brain lead coupled to the CSF catheter. The method may include developing a deep neural network (DNN) associated with the subject or the disease.

By collecting high quality data derived from within the brain (iEEG) and Artificial Intelligence (AI) techniques, an effective subject- or disease-specific DNNs may be obtained. The DNN may be used for any suitable purpose. For example, the DNN may be used for patient management. The DNN may support the construction of a non-invasive symptom management and diagnostic tool for non-implanted patients.

Deep neural networks (DNNs) are a sub-field of machine learning which leverage a composition of many nonlinear functions to map input data into a new desired output domain. The parameters of these nonlinear functions are not directly designed by humans, but instead learned from vast quantities of data. This allows the continual learning and improvement of a DNNs performance through the collection of more high-quality data. DNNs have found widespread success across numerous domains that often match or surpass human performance on specific tasks. Initially, deep learning strategies may be developed for iEEG analysis associated with waking EEG classification for emotions, motor activity, cognitive activity, seizure detection, and sleep scoring including convolutional neural networks and recurrent neural networks. The initial strategies may utilize one or both of supervised and unsupervised training approaches. The course of sleep disturbances may include ongoing analysis with local field potentials from deep brain electrodes subject to ongoing analysis by modern machine learning techniques as well as classical methods such as support vector machine and decision tree methods.

Suitable AI methods for establishing DNNs are described in U.S. Provisional Patent Application No. 63/054,522, entitled MONITORING AND TREATMENT BASED ON CONTINUOUS INTRACRANIAL EEG ACTIVITY, filed on Jul. 21, 2020, and naming Cerebral Therapeutics, Inc. as an Applicant, which is incorporated herein by reference in its entirety to the extent that it does not conflict with the disclosure presented herein.

Use

Any suitable therapeutic fluid may be infused through a catheter described herein for treating a disease of the brain. The therapeutic fluid may comprise any suitable therapeutic agent. Preferably, the therapeutic agent is an agent for treating a disease of the brain. Examples of diseases of the brain include any diseases with pathology or dysfunction occurring in any component of the brain (including the cerebral hemispheres, diencephalon, brain stem, and cerebellum) or the spinal cord. Preferably, the devices and systems described herein are used to treat a disease of the brain that is resistant to treatment through systemic routes of administration, such as oral, intravenous, intramuscular, and intraperitoneal administration. The devices and systems described herein may also be used if a patient is at serious risk if direct central administration of a therapeutic fluid is not commenced.

The therapeutic fluid may be infused into the CSF or other brain region at any suitable rate. Preferably, flow rate into the brain is limited to 20 milliliters or less per day, such as 10 milliliters or less per day, or 5 milliliters per day or less. For example, the therapeutic fluid may be infused at a metered rate of 4 milliliters per day or less, such as 3 milliliters per day or less, 2 milliliters per day or less, or about 1 milliliter per day.

Withdrawal of CSF from the brain should be limited to 3,500 milliliters per day or less, preferably 200 milliliters per day or less.

The therapeutic fluid may comprise any suitable therapeutic agent. The therapeutic agent selected may depend on the disease being treated. The therapeutic fluid, such as a solution, may contain any suitable concentration of the therapeutic agent. The concentration of the therapeutic agent will depend on the therapeutic agent employed. In some embodiments, the therapeutic fluid is a solution comprising a therapeutic agent at a concentration in a range of from about 10 milligrams per milliliter to about 500 milligrams per milliliter, such as from about 50 milligrams per milliliter to about 450 milligrams per milliliter.

For purposes of illustration, a list of suitable anti-epileptic therapeutic agent that may be included in a therapeutic fluid, such as a solution, includes carbamazepine; tiagabine, levetiracetam; lamotrigine; pregabalin; fenfluramine; gabapentin; phenytoin; topiramate; oxcarbazepine; valproate; valproic acid; zonisamide; perampanel; eslicarbazepine acetate; lacosamide; vigabatrin; rufinamide; fosphenytoin; ethosuximide; phenobarbital; diazepam; lorazepam; clonazepam; clobazam; ezogabine; felbamate; primidone; acetazolamide; brivaracetam; clorazepate; ethotoin; mephenytoin; methsuximide; trimethadione; bumetanide; adenosine; and an adenosine a1 receptor agonist. In some embodiment, the therapeutic agent is valproic acid or a pharmacologically acceptable salt thereof. For purposes of the present disclosure, reference to a compound includes reference to salts, hydrates, solvates, and polymorphs thereof.

Examples of other therapeutic agents that may be included in a therapeutic fluid for treating or diagnosing a CNS disease include Edaravone (e.g., Radicava®) for Amyotrophic Lateral Sclerosis (ALS), Valbenazine (e.g., Ingrezza®)) for Tardive dyskinesia, Deuterabenazine (e.g., Austedo®) for Huntington's disease, Ocrelizumab (e.g., Ocrevus®) for Multiple sclerosis, Safinamide (e.g., Xadago®) for Parkinson's disease, Nusinersen (e.g., Spinraza®) for Spinal muscular atrophy (SMA), Daclizumab (e.g., Zinbryta®) for Multiple sclerosis, Pivavanserin (e.g., Nuplazid®) for Hallucinations and delusions associated with psychosis, Aripiprazole lauroxil (e.g., Aristada®) for Schizophrenia, Caripazine (e.g., Vraylar®) for Schizophrenia and bipolar disorder, Brexpiprazole (e.g., Rexulti®) for Schizophrenia, Peginterferon beta-la (e.g., Plegridy®) for Multiple sclerosis, Eslicarbazepine acetate (Aptiom®) for Epilepsy associated seizures, Flutemetamol F 18 (e.g., Vizamyl®) Radioactive diagnostic for Alzheimer's disease, Vortioxetine (e.g., Brintellix®) for Major depressive disorder, Dimethyl fumerate (e.g., Tecfidera®) for multiple sclerosis, and Gadoterate megumine (e.g., Dotarem®) for MRI-based brain imaging.

Another example of therapeutic agents that may be included in a therapeutic fluid is a Dominant Negative Tumor Necrosis Factor (DN-TNF) such as XPRO® 1595 and the like.

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. As used in this specification and the appended claims, the term "or" is generally employed in its sense including "and/or" unless the content clearly dictates otherwise. The term "and/or" means one or all the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the inventive technology.

Any direction referred to herein, such as "top," "bottom," "side," "upper," "lower," and other directions or orientations are described herein for clarity and brevity but are not intended to be limiting of an actual device or system. Devices and systems described herein may be used in a number of directions and orientations.

As used herein, "providing" a device or system means manufacturing the device or system, assembling the device or system, purchasing the device or system, or otherwise obtaining the device or system.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must).

The words "include," "including," and "includes" indicate open-ended relationships and therefore mean including, but not limited to. Similarly, the words "have," "having," and "has" also indicated open-ended relationships, and thus mean having, but not limited to. Similarly, the terms "comprise" and "comprising" indicate open-ended relationships, and thus mean comprising, but not limited to. The terms "consisting essentially of" and "consisting of" are subsumed within the term "comprising." For example, a catheter comprising tubing may be a catheter consisting of tubing. The term "consisting essentially of" means a recited list of one or more items belonging to an article, kit, system, or method and other non-listed items that do not materially affect the properties of the article, kit, system, or method.

The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a catheter connector may be configured to place a lumen of a catheter in fluid communication with a fluid path, even when the catheter is not connected to the catheter connector).

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

The invention is defined in the claims. However, below there is provided a non-exhaustive list of non-limiting examples. Any one or more of the features of these examples may be combined with any one or more features of another example, embodiment, or aspect described herein.

Example Ex1 A device or system for delivering fluid to or removing fluid from a cerebrospinal fluid (CSF)-containing space of a brain and for recording electrical activity from white or grey matter in the brain, the device or system comprising: (i) a CSF catheter comprising a proximal end, a distal end portion, and a first lumen extending from the proximal end to the distal end portion; and (ii) an electrode positioned a distance from a distal end of the CSF catheter such that the electrode would be placed in contact with white or grey matter of the brain if the distal end of the CSF catheter were positioned in the CSF-containing space.

Example Ex2 The device or system of Ex1, wherein the electrode is positioned a distance from about 0.5 centimeters to about 6 centimeters to the distal end of the CSF catheter.

Example Ex3 The device or system of Ex2 wherein the electrode is positioned a distance from about 1 centimeter to about 5 centimeters to the distal end of the CSF catheter.

Example Ex4 The device or system of Ex1, wherein the electrode is positioned a distance from about 2 centimeters to about 6 centimeters to the distal end of the CSF catheter.

Example Ex5 A device or system for delivering fluid to or removing fluid from a cerebrospinal fluid (CSF)-containing space of a subject and for recording electrical activity from white or grey matter in a brain of the subject, the device or system comprising: (i) a CSF catheter comprising a proximal end, a distal end portion, and a first lumen extending from the proximal end portion to the distal end portion; and (ii) an electrode positioned relative to the CSF catheter at a distance from about 0.5 centimeters to about 6 centimeters to a distal end of the CSF catheter.

Example Ex6 A device or system according to Ex5, wherein the electrode is positioned from about 1 centimeter to about 5 centimeters from the distal end of the catheter.

Example Ex7 A device or system according to Ex5, wherein the electrode is positioned from about 2 centimeters to about 6 centimeters from the distal end of the catheter.

Example Ex8 The device or system of any one of Ex1 to Ex7, wherein the CSF catheter comprises the electrode.

Example Ex9 The device or system of any one of Ex1 to Ex7, further comprising a brain lead, wherein the brain lead comprises the electrode and wherein the brain lead is coupled to the CSF catheter.

Example Ex10 The device or system of Ex9, wherein the brain lead is coupled relative to the CSF catheter at the distal end portion of the CSF catheter.

Example Ex11 The device or system of Ex9 or Ex10, wherein the brain lead is coupled to the CSF catheter in proximity to a mid-portion of the CSF catheter.

Example Ex12 The device or system of any one of Ex9 to Ex11, wherein the brain lead is coupled to the CSF catheter in proximity to the proximal end of the CSF catheter.

Example Ex13 The device or system of any one of Ex9 to Ex12, wherein the brain lead is secured to the CSF catheter along a substantial length of the CSF catheter.

Example Ex14 The device or system of any one of Ex9 to Ex13, wherein the brain lead is secured to the CSF catheter with adhesive.

Example Ex15 The device or system of any one of Ex9 to Ex14, wherein the brain lead is mechanically fixed relative to the CSF catheter.

Example Ex16 The device or system of any one of Ex9 to Ex15, comprising a sleeve disposed over the brain lead and the CSF catheter.

Example Ex17 The device or system of any one of Ex9 to Ex16, comprising a sleeve, wherein the sleeve is configured to be disposed over the brain lead and the CSF catheter.

Example Ex18 The device or system of Ex16 or Ex17, wherein the sleeve is elastomeric and configured to press the brain lead against the CSF catheter when the sleeve is disposed over the brain lead and the catheter.

Example Ex19 The device or system of any one of Ex16 to Ex18, wherein the sleeve comprises a window positioned over, or configured to be positioned over, the electrode.

Example Ex20 The device or system of any one of Ex9 to Ex19, wherein the CSF catheter defines a groove and wherein the brain lead is received in the groove or is configured to be received in the groove.

Example Ex21 The device or system of Ex20, wherein the groove engages, or is configured to engage, the brain lead via snap fit.

Example Ex22 The device of system of any one of Ex9 to Ex21, further comprising a snap fit connector, wherein the CSF catheter and brain lead are engaged by, or are configured to be engaged by, the snap fit connector.

Example Ex23 The device or system of any one of Ex1 to Ex22, wherein the electrode would be placed in contact with the white or grey matter of the brain if the distal end of the CSF catheter were positioned in a lateral cerebral ventricle.

Example Ex24 The device or system of any one of Ex1 to Ex23, comprising one to sixty-three additional electrodes.

Example Ex25 The device or system of any one of Ex1 to Ex24, comprising a brain signal electrical interconnect, wherein the brain signal electrical interconnect comprises a contact electrically coupled to the electrode, and comprises one to sixty-three additional contacts each discretely electrically coupled to one of the one to sixty-three additional electrodes if present.

Example Ex26 The device or system of Ex25, wherein the CSF catheter comprises the brain signal electrical interconnect.

Example Ex27 The device or system of Ex25 comprising the brain lead according to Ex9, wherein the brain lead comprises the brain signal electrical interconnect.

Example Ex28 The device or system of Ex27, wherein the brain signal electrical interconnect is in proximity to a proximal end of the brain lead.

Example Ex29 The device or system of Ex25, wherein the CSF catheter comprises the electrode and wherein the brain signal electrical interconnect is physically separate from the CSF catheter.

Example Ex30 The device or system of Ex29, further comprising a cable extending from the CSF catheter to the brain signal electrical interconnect, wherein the cable comprises a conductor electrically connecting the electrode to the contact.

Example Ex31 The device or system of any one of Ex1 to Ex30, further comprising an access port having a first fluid flow path in communication with the first lumen of the CSF catheter or having a connector configured to secure the CSF catheter such that first lumen is in communication with the first fluid flow path.

Example Ex32 The device or system of Ex31, wherein the access port is configured to be implanted below a scalp.

Example Ex33 The device or system of Ex32, wherein at least a portion of the access port is configured to be implanted over a burr hole.

Example Ex34 The device or system of Ex32 or Ex33, wherein at least a portion of the access port is configured to be implanted in the burr hole.

Example Ex35 The device or system of any one of Ex31 to Ex34, wherein the access port defines a passageway configured to receive the cable of the device or system according to Ex30.

Example Ex36 The device or system of any one of Ex31 to Ex34, comprising the brain lead, wherein the access port defines a passageway configured to receive the brain lead.

Example Ex37 The device or system of Ex35 or Ex36, wherein the passageway extends though the access port from a bottom surface to a top surface or to a side surface.

Example Ex38 The device or system of any one of Ex35 to Ex37, wherein passageway has a sufficiently large inner dimensions for the electrical interconnect to be fed through the passageway.

Example Ex39 The device or system of Ex38, wherein the passageway comprises a slot in an outer surface of the access port.

Example Ex40 The device or system of any one of Ex31 to Ex39, wherein the access port comprises a first port interconnect configured to electrically couple to the brain signal electrical interconnect of any one of Ex26 to Ex30.

Example Ex41 The device or system of Ex40, wherein the access port comprises a second port interconnect, wherein the second port interconnect is electrically coupled to the first port interconnect.

Example Ex42 The device or system of any one of Ex1 to Ex41, further comprising signal apparatus for processing, transmitting, or processing and transmitting data regarding the signals recorded by the electrode.

Example Ex43 The device or system of Ex42, wherein the signal apparatus is configured to be implanted in a patient.

Example Ex44 The device or system of Ex42 or Ex43, further comprising an implantable infusion device, wherein the implantable infusion device comprises the signal apparatus.

Example Ex45 The device or system of any one of Ex42 to Ex44, further comprising an external apparatus configured to receive transmitted data from the signal apparatus.

Example Ex46 The device or system of any one of Ex42 to Ex45, wherein the signal apparatus is electrically coupled to, or configured to be electrically coupled to, the second port interconnect according to Ex41 or the brain signal interconnect according to any one of Ex26 to Ex30.

Example Ex47 The device or system of Ex46, further comprising a signal apparatus lead comprising a signal apparatus lead interconnect, wherein the signal apparatus lead is electrically coupled to the signal apparatus.

Example Ex48 The device or system of Ex47, wherein the signal apparatus lead interconnect is configured to electrically couple with the electrical interconnect or the second port interconnect or the brain signal interconnect of any one of Ex23 to Ex29.

Example Ex49 The device or system of any one of Ex1 to Ex48, wherein the CSF catheter comprises a second lumen extending from the proximal end to the distal end portion.

Example Ex50 The device or system of Ex45, comprising an access port according to any one of Ex31 to Ex41, wherein the access port defines a second fluid flow path in fluid communication or configured to be placed in fluid communication with the second lumen of the CSF catheter.

Example Ex51 The device or system of Ex50, wherein the access port is configured to be operably coupled with an implantable infusion device such that therapeutic fluid from the implantable infusion device may be infused through the second fluid flow path and the second lumen of the CSF catheter.

Example Ex52 The device or system of Ex51, wherein the second fluid flow path comprises a microbial filter.

Example Ex53 The device or system of Ex52, wherein the first fluid flow path is free from a microbial filter.

Example Ex54 The device or system of any one of Ex50 to Ex53, wherein the access port is configured to connect to a drainage catheter such that CSF from the CSF-containing space may be drained through the second lumen of the CSF catheter, the second fluid path of the access port, and through a drainage lumen of the drainage catheter.

Example Ex55 The device or system of any one of Ex1 to Ex54, wherein the CSF catheter has a length from about 45 millimeters to about 80 millimeters within the cranium.

Example Ex56 The device or system of any one of Ex1 to Ex54, wherein the CSF catheter has a length from about 60 millimeters to about 70 millimeters within the cranium.

Example Ex57 The device or system of any one of Ex1 to Ex54, wherein the CSF catheter has a length from about 62 millimeters to about 68 millimeters within the cranium.

Example Ex58 A method comprising: (i) recording an electrical signal from white or grey matter of a brain of a subject; and (ii) determining a brain state of the subject or predicting a future brain state of the subject based on the recorded electrical signal.

Example Ex59 The method of Ex58, wherein recording the electrical signal from the white or grey matter of the brain of the subject comprises recording the signal from an electrode positioned in the white or grey matter.

Example Ex60 The method of Ex59, wherein the electrode is on a catheter positioned to deliver fluid to, or withdraw fluid from, a brain of the subject.

Example Ex61 The method of Ex59, wherein the catheter is positioned to deliver fluid to, or withdraw fluid from, a CSF-containing space of the subject.

Example Ex62 The method of Ex61, wherein the catheter is positioned to deliver fluid to, or withdraw fluid from, a cerebral ventricle of the subject.

Example Ex63 The method of Ex59, wherein the electrode is on a lead, and wherein the lead is coupled to a catheter.

Example Ex64 The method of Ex63, wherein the catheter is positioned to deliver fluid to, or withdraw fluid from, a brain of the subject.

Example Ex65 The method of Ex63, wherein the catheter is positioned to deliver fluid to, or withdraw fluid from, a CSF-containing space of the subject.

Example Ex66 The method of Ex64, wherein the catheter is positioned to deliver fluid to, or withdraw fluid from, a cerebral ventricle of the subject.

Example Ex67 The method of any one of Ex58 to Ex66, further comprising:

provoking the subject, wherein recording the electrical signal from the white or grey matter of the brain of the subject comprises recording a provoked electrical response.

Example Ex68 The method of Ex63, wherein provoking the subject comprises applying an electrical signal to the white or grey matter of the subject.

Example Ex69 A method comprising: (i) delivering fluid to, or withdrawing fluid from, a CSF-containing space of a brain of a subject, wherein the fluid is delivered or withdrawn through a first lumen of a CSF catheter; and (ii) recording an electrical signal from the white or grey matter via an electrode.

Example Ex70 The method of Ex69, wherein the electrode is fixed at a position relative to a distal end of the CSF catheter.

Example Ex71 The method of Ex69 or Ex70, wherein the CSF catheter comprises the electrode.

Example Ex72 The method of Ex69 or Ex70, wherein a lead comprises the electrode, and wherein the lead is secured relative to the CSF catheter.

Example Ex73 The method of any one of Ex69 to Ex72, wherein the catheter is positioned to deliver fluid to, or withdraw fluid from, a cerebral ventricle through the first lumen.

Example Ex74 The method of any one of Ex69 to Ex73, further comprising transmitting data regarding the recorded electrical signal to apparatus external to the subject.

Example Ex75 The method of any one of Ex69 to Ex74, further comprising determining a brain state of the subject or predicting a future brain state of the subject based on the recorded electrical signal.

Example Ex76 The method of any one of Ex69 to Ex75, further comprising provoking the subject, wherein recording the electrical signal from the white or grey matter of the brain of the subject comprises recording a provoked electrical response.

Example Ex77 The method of Ex76, wherein provoking the subject comprises applying an electrical signal to the brain of the subject.

Example Ex78 A method according to Ex77, wherein the signal is applied by the electrode positioned in white or grey matter of the brain.

Example Ex79 A device or system comprising: (A) an implantable access port, the access port comprising: (ii) an opening accessible by a needle when the access port is implanted; (iii) a first catheter connector; (iv) a second catheter connector; (v) a first fluid flow path extending from the opening to the first catheter connector; and (vi) a second fluid flow path extending from the second catheter connector to the first catheter connector; (B) a CSF catheter coupled to, or operably couplable to, the first catheter connector, the CSF catheter comprising a proximal end, a distal end portion, and first and second lumens extending from the proximal end to the distal portion of the CSF catheter; and (C) an electrode, wherein the first lumen is in communication with the first fluid flow path and the second lumen is in communication with the second fluid flow path when the proximal end of the CSF catheter is coupled to the first catheter connector, wherein the CSF catheter has a length such that a distal end is configured to extend to a CSF-containing space of a subject when the access port is implanted, wherein the electrode is positioned a distance from the distal end of the CSF catheter such that the electrode is positioned in white or grey matter of a brain of the subject when the access port is implanted and the distal end of the CSF catheter is positioned in the CSF-containing space.

Example Ex80 The device or system of Ex79, wherein the second fluid flow path comprises a microbial filter.

Example Ex81 The device or system of Ex79 or Ex80, wherein the first fluid flow path is free of a microbial filter.

Example Ex82 The device or system of any one of Ex79 to Ex81, wherein the access port is configured to be implanted under a scalp of a subject.

Example Ex83 The device or system of any one of Ex79 to Ex82, wherein the CSF catheter comprises the electrode.

Example Ex84 The device or system of any one of Ex79 to Ex82, comprising a lead, wherein the lead comprises the electrode.

Example Ex85 The device or system of Ex84, wherein the lead is secured relative to the CSF catheter.

Example Ex86 The device or system of any one of Ex79 to Ex85, comprising signal apparatus electrically coupled to, or configured to electrically couple to, the electrode.

Example Ex87 The device or system of Ex86, wherein the signal apparatus is configured to be implanted under the scalp of the subject in proximity to an ear.

Example Ex88 The device or system of Ex86, wherein the CSF catheter comprises the signal apparatus.

Example Ex89 The device or system of Ex86, further comprising an implantable infusion device operably coupled to the second fluid flow path, wherein the implantable infusion device comprises the signal apparatus.

Example Ex90 The device or system according to any one of Ex86 to Ex89, wherein the signal apparatus is configured to process, transmit, or process and transmit data regarding electrical signals recorded by the electrode.

Example Ex91 The device or system of Ex90, further comprising external apparatus configured to receive data transmitted by the signal apparatus.

Example Ex92 The device of Ex91, wherein the external apparatus is configured to wirelessly power the signal apparatus.

Example Ex93 A method comprising: (A) providing a device or system comprising: (i) an implantable access port comprising: an opening accessible by a needle when the access port is implanted; a first catheter connector; a second catheter connector; a first fluid flow path extending from the opening to a first catheter connector; and a second fluid flow path extending from the second catheter connector to the first catheter connector; (ii) a CSF catheter coupled to, or operably couplable to, the first catheter connector, the CSF catheter comprising a proximal end, a distal end portion, first and second lumens extending from the proximal end to the distal portion of the CSF catheter, wherein the first lumen is in communication with the first fluid flow path and the second lumen is in communication with the second fluid flow path when the proximal end of the catheter is coupled to the first catheter connector, and wherein the CSF catheter has a length such that a distal end is configured to extend to a CSF-containing space of a subject when the access port is implanted; and (iii) an electrode positioned a distance from the distal end of the CSF catheter such that the electrode is positioned in white or grey matter of a brain of the subject when the access port is implanted and the distal end of the CSF catheter is positioned in the CSF-containing space; (B) implanting the device or system such that the proximal end of the CSF catheter is coupled to the first catheter connector, the first lumen of the catheter is in communication with the first fluid flow path of the access port, the second lumen of the CSF catheter is in communication with the second fluid flow path of the access port, the distal end of the CSF catheter is positioned in the CSF-containing space of the subject, and the electrode is positioned in the white or grey matter of the brain of the subject; and (C) recording an electrical signal from the white or grey matter via the one or more electrodes.

Example Ex94 The method of Ex93, wherein the access port is configured to be implanted under a scalp of the subject.

Example Ex95 The method of Ex93 or Ex94, wherein the CSF catheter comprises the electrode.

Example Ex96 The method of Ex93 or Ex94, wherein a lead comprises the electrode, and wherein the lead is secured relative to the CSF catheter.

Example Ex97 The method of any one of Ex93 to Ex96, wherein the distal end of the catheter is positioned in a cerebral ventricle.

Example Ex98 The method of any one of Ex93 to Ex97, comprising transmitting data regarding the recorded electrical signal to apparatus external to the subject.

Example Ex99 The method of any one of Ex93 to Ex98, comprising determining a brain state of the subject or predicting a future brain state of the subject based on the recorded electrical signal.

Example Ex100 The method of any one of Ex93 to Ex99, comprising provoking the subject, wherein recording the electrical signal from the white or grey matter of the brain of the subject comprises recording a provoked electrical response.

Example Ex101 The method of Ex100, wherein provoking the subject comprises applying an electrical signal to the brain of the subject.

Example Ex102 The method of Ex101, wherein the signal is applied by the electrode positioned in white matter or grey of the brain.

Example Ex103 The method of any one of Ex93 to Ex102, comprising infusing a therapeutic fluid through the second fluid flow path of the access port and through the second lumen of the catheter.

Example Ex104 The method of Ex103, wherein the second lumen is in communication with a cerebral ventricle.

Example Ex105 The method of Ex103 or Ex104, wherein the rate at which the therapeutic fluid is infused is altered based on data regarding the recorded electrical signal.

Example Ex106 The method of any one of Ex93 to Ex105, wherein the subject is at risk of or suffering from epilepsy, a head injury, stroke, subarachnoid hemorrhage, hydrocephalus, or brain infection.

Example Ex107 The method of Ex106, wherein the therapeutic fluid infused according to any one of Ex103 to Ex105 comprises an antiepileptic agent.

Example Ex108 The method of Ex107, wherein the antiepileptic agent comprises valproic acid or a pharmaceutically acceptable salt thereof.

Example 109 A method comprising: (i) implanting a catheter such that a distal end is positioned in a cerebrospinal fluid (CSF)-containing space of a brain of a subject, wherein implanting the catheter causes an electrode to be placed in contact with white matter or grey matter of the brain; (ii)

infusing therapeutic fluid into the CSF-containing space, or withdrawing CSF from the CSF containing space, via a lumen of the catheter; and (iii) recording an electrical signal from the white or grey matter via the electrode.

Example Ex110 The method of Ex109, wherein the catheter comprises the electrode.

Example Ex111 The method of Ex109, wherein a lead comprises the electrode.

Example Ex112 The method of Ex111, comprising securing a portion of the lead to the catheter.

Example Ex113 The method of Ex111 or Ex112, comprising securing a distal portion of the lead to the catheter.

Example Ex114 The method of any one of Ex111 to Ex113, comprising securing a mid-portion of the lead to the catheter.

Example Ex115 The method of any one of Ex111 to Ex114, comprising securing a proximal portion of the lead to the catheter.

Example Ex116 The method of any one of Ex111 to Ex115, comprising securing the lead to the catheter along a substantial length of the catheter.

Example Ex117 The method of any one of Ex111 to Ex116, wherein securing the lead to the catheter comprises adhering the lead to the catheter.

Example Ex118 The method of any one of Ex111 to Ex117, wherein securing the lead to the catheter comprises mechanically fixing the lead to the catheter.

Example Ex119 The method of any one of Ex111 to Ex117, wherein securing the lead to the catheter comprises disposing a sleeve over the lead and the catheter.

Example Ex120 The method of Ex119, wherein the sleeve is elastomeric and configured to press the lead against the catheter when the sleeve is disposed over the lead and the catheter.

Example Ex121 The method of Ex119 or Ex120, wherein the sleeve comprises a window and the method comprises positioning the window over the electrode.

Example Ex122 The method of any one of Ex111 to Ex121, wherein the catheter defines a groove configured to receive the lead and wherein the method comprises disposing the lead in the groove.

Example Ex123 The method of Ex122, wherein the groove is configured to engage the lead via snap fit and the method comprises snaping the lead into the groove.

Example Ex124 The method of any one of Ex111 to Ex123, further comprising snapping the lead and the catheter into a snap fit connector.

Example Ex125 The method of any one of Ex109 to Ex124, wherein recording the electrical signal comprises recording an electrical signal from the white matter of the brain.

Example Ex126 The method of any one of Ex109 to Ex125, further comprising determining a brain state of the subject or predicting a future brain state of the subject based on the recorded electrical signal.

Example Ex127 The method according to any one of Ex109 to Ex126, further comprising: provoking the subject, wherein recording the electrical signal from the white or grey matter of the brain of the subject comprises recording a provoked electrical response.

Example Ex128 The method of Ex127, wherein provoking the subject comprises applying an electrical signal to the white or grey matter.

Example Ex129 The method of Ex128, wherein applying the electrical signal comprises applying the electrical signal via the electrode.

Example Ex130 The method of Ex128, wherein applying the electrical signal comprises applying an electrical signal via a stimulating electrode that is different than the electrode recording the electrical signal from the white or grey matter.

Example Ex131 The method of any one of Ex109 to Ex130, comprising positioning the distal end of the catheter in a cerebral ventricle.

Example Ex132 The method of Ex131, wherein the cerebral ventricle is a lateral ventricle.

Example Ex133 The method of any one of any one of Ex109 to Ex132, comprising infusing fluid into the CSF-containing space through a first lumen of the catheter, and withdrawing CSF from the CSF-containing space through a second lumen of the catheter.

Example Ex134 The method of any one of Ex109 to Ex133, wherein infusing fluid into the CSF-containing space comprises passing the fluid through a filter.

Example Ex135 The method of Ex134, wherein the filter is a microbial filter.

Example Ex136 The method of any one of Ex109 to Ex135, wherein withdrawing the fluid from the CSF-containing space comprises withdrawing the fluid without passing the fluid through a filter.

Example Ex137 The method of any one of Ex109 to Ex136, further comprising transmitting data regarding the recorded electrical signal to apparatus external to the subject.

Example Ex138 The device, system, or method of any one of Ex1 to Ex137, wherein the catheter (e.g., the cranial catheter) is an external ventricular drainage catheter or a ventriculoperitoneal shunt.

EXAMPLES

Provided below are non-limiting examples that illustrate some aspects of the present disclosure.

Example 1—Electrode Placement and Configuration

Electrode placement and configurations were evaluated to determine signal strength and signal to noise ratio. Differential and referential configurations were evaluated.

In differential mode, the system comprises an active electrode, a reference electrode, and a ground. The signal difference between an active electrode and a reference electrode is preferably positioned a substantial distance from an active electrode and from the ground.

For a system as described herein, a differential mode recording may be achieved using four electrode (two electrodes per amplifier) and an additional ground electrode.

A schematic diagram illustrating signals in differential mode is shown in FIG. 29. In differential mode, the system may be configured to detect small differences between electrode pairs and may be less likely to be affected by large artifacts originating near the ground electrode (FIG. 29-A). However, the system may not be particularly effective at detecting larger common signals (FIG. 29-B).

To detect larger common signals, the system may be configured in referential mode, which may also be referred to as single-ended mode. Referential mode may use a single active electrode per amplifier. In referential mode, the output of the active electrode is amplified relative to the ground electrode, as opposed to the reference electrode in differential mode. The ground is preferably placed a substantial distance from the active electrode, which may result in amplification of signals that affect larger parts of the brain.

A schematic diagram illustrating signals in referential mode is shown in FIG. 30. While being effective at detecting larger common signals such as seizures (FIG. 30-A), referential mode may be sensitive to artifacts (FIG. 30-B). Proper placement of the ground electrode may mitigate some issues associated with artifacts.

To detect larger scale common signals, which may be more indicative of brain state, it is recommended to use referential mode recording while mitigating the effects of ground signal noise by careful consideration of electrode placement.

FIG. 31 is a schematic illustration of ground electrode placement that were considered. The six placements correspond to (1) on a CSF catheter at a distal end, (2) on the CSF catheter near an access port, (3) on the underside of the access port, (4) outside near the access port, (5) along a signal apparatus lead near a connector, and (6) on the signal apparatus behind the ear.

Table 1 compares the potential placement of the ground electrode and assigns a score (higher scores are considered better) for each of the locations relative to rejection of muscle artifact and movement, electrostatic and electromagnetic interference (ESD and EMC), recording area, signal level (amplitude), signal to noise ratio, and potential for large signal clipping (overload). Differential mode is shown for comparison.

TABLE 1

Scores for placement of ground electrode-differential and referential mode

| Mode | EEG | Gn | G loc | Msc | Mvt | ESD | EMC | Reg | Sig | S/N | Over | Score |
|------|-----|-----|-------|-----|-----|-----|-----|-----|-----|-----|------|-------|
| Diff | 4 | 0 | — | 5 | 5 | 5 | 5 | 1 | 1 | 1.0 | 5 | 32.0 |
| Ref | 2 | 1 | 1 | 5 | 5 | 5 | 5 | 2 | 2 | 2.0 | 5 | 39.0 |
| Ref | 2 | 1 | 2 | 5 | 5 | 4 | 4 | 4 | 5 | 4.7 | 4 | 53.0 |
| Ref | 2 | 1 | 3 | 5 | 1 | 1 | 1 | 4 | 4 | 2.4 | 3 | 36.2 |
| Ref | 2 | 1 | 4 | 3 | 3 | 1 | 1 | 5 | 3 | 1.4 | 1 | 31.2 |
| Ref | 2 | 1 | 5 | 2 | 3 | 1 | 1 | 5 | 3 | 1.2 | 1 | 29.6 |
| Ref | 2 | 1 | 6 | 2 | 4 | 1 | 1 | 5 | 4 | 1.9 | 1 | 33.6 |
| Score Weights | | | | 1 | 1 | 1 | 1 | 3 | 1 | 3 | 1 | |

Mode: Diff (differential), Ref (referential), EEG: number of EEG electrodes, Gn: number of ground electrodes, G loc: location of ground electrode (see FIG. 31 and text above), Msc: Muscle artifact immunity, Mvt: electrode movement immunity, ESD: ESD immunity, EMC: EMC immunity, Reg: Recording region, Sig: Signal level, S/N: Signal-to-noise ratio, Over: Overload immunity, Score: Overall score.

electrode may be amplified. The reference electrode may be a common reference for more than one active electrode. The Based on the information above, referential mode with the ground electrode placed on the CSF catheter (or on brain lead associated with the CSF catheter) near the access port (location 2 of FIG. 30) is recommended to detect larger scale changes, such as brain state.

Example 2—Post-Traumatic Stress Disorder (PTSD)

The devices and systems disclosed herein may be used to treat or monitor any suitable disease. For purposes of illustration, treatment of PTSD and monitoring of electrical signals is discussed in more detail. A patient suffering from PTSD may be diagnosed according to criteria provided in DSM-5 (American Psychiatric Association. (2013). *Diagnostic and statistical manual of mental disorders* ($5^{th}$ ed.). https://doi.org/10.1176/appi.books.9780890425596). The DSM-5 is incorporated herein by reference to the extent that it does not conflict with the disclosure presented herein.

Additional information regarding treatment and monitoring of PTSD and development of a PTSD DNN is described in U.S. Provisional Patent Application No. 63/166,705, filed on Mar. 26, 2021 and U.S. Provisional Patent Application No. 63/172,313, filed on Apr. 8, 2021, which applications are hereby incorporated herein in their respective entireties to the extent that they do not conflict with the disclosure presented herein.

High quality intracranial brain electroencephalography (iEEG) data may be obtained from PTSD patients employing the systems and devices described herein. The data may be used to better understand PTSD. The data may be used to monitor a state of the disease (such as severity), a state of the patient, or the like. The data may be used to direct, enhance, or direct and enhance PTSD therapy. The PTSD therapy may include one or more of cognitive therapy, psychological therapy, and pharmacological therapy.

Treatment of PTSD may include administration of a therapeutic agent us directly to CSF of a patient employing the devices and systems described herein. For example, the therapeutic agent may be administered to a cerebral ventricle. Administering to a cerebral ventricle enables delivery of the therapeutic agent adjacent to the specific region or regions of the brain responsible for severe traumatic memory recall. Such therapy may diminish the frequency, the severity, or the frequency and severity of PTSD intrusive memory recall from the hippocampus/basolateral amygdala memory neurons.

Any suitable therapeutic agent may be used to treat PTSD. For example, the therapeutic agent may be a selective serotonin reuptake inhibitor, an antihypertensive agent, or an antiepileptic agent. An example of a suitable antiepileptic agent is valproate or valproic acid. An example of a suitable form of valproate is sodium valproate.

The devices and systems described herein include catheters for delivering therapeutic agents to the CSF or delivering therapeutic agents to the CSF and for withdrawing CSF from the brain. A catheter may include one or more electrodes configured to be positioned within or close to white matter of the brain, grey matter of the brain, or white matter and grey matter of the brain. In addition or alternatively, a medical lead separate from a catheter may include one or more electrodes configured to be positioned within or close to white matter of the brain, grey matter of the brain, or white matter and grey matter of the brain. Preferably, the medical lead is configured to be coupled to, or is coupled to, a catheter so that implantation of the catheter results in implantation of the lead, if the catheter is implanted in the brain. That is, it is preferable that only one surgical procedure is performed to place the lead and the catheter. The electrodes may record electrical signals from within the brain.

By placing the electrodes within or in proximity to brain tissue, such as white matter or grey matter, less "noisy" signals may be obtained than with scalp-based EEG recordings. Such higher quality signals may facilitate interpretation of data recorded by the electrodes.

Preferably, the catheter comprises multiple lumens. A first lumen may be used, for example, to withdraw CSF from the brain, and a second lumen may be used, for example, to deliver a therapeutic fluid to the brain. The withdrawn CSF may be used to monitor disease or therapy progression, as well as monitor brain state, which may be used to, for example, adjust the rate of delivery of the therapeutic agent.

In addition or alternatively, data recorded by the electrodes may be used to monitor disease or therapy progression, as well as monitor a current brain state or predict a future brain state. The rate of delivery of the therapeutic fluid may be adjusted based on data recorded by the electrodes.

The combination of analysis of withdrawn CSF and data recorded by the electrodes may result in substantially improved therapy and therapeutic outcomes than analysis of either one alone.

Examples of studies that may be done are now provided. Overview of Potential Pilot Study An implantable central nervous system (CNS) drug administration system and iEEG monitoring device may be implanted in 15 subjects with severe PTSD. In Aim 1, these subjects may receive a site specific therapeutic and may be included in the development of a novel iEEG PTSD focused database for symptom management which may be utilized for the development of a non-invasive PTSD diagnostic in the second aim.

In Aim 1, delivery of therapeutic through the minimally invasive central nervous system (CNS) drug administration system and iEEG monitoring device may be used to demonstrate initial clinical efficacy (improvement in the Clinician Administered PTSD Scale (CAPS-5) B Criterion, the standardized PTSD clinical questionnaire measure) and to collect PTSD specific implantable iEEG data.

In Aim 2, a PTSD DNN, trained on implanted iEEG data from the pilot clinical study, may be applied to a cohort of severe un-implanted PTSD subjects. Artificial intelligence (AI) may form the basis for iEEG analysis emphasizing those deep learning strategies initially shown most helpful for waking EEG classification for emotions, motor activity, cognitive activity, seizure detection and sleep scoring associated with an ongoing epilepsy trial. The course of sleep disturbances, a primary symptom of PTSD, may include ongoing analysis with local field potentials from deep brain electrodes subject to ongoing analysis by modern machine learning techniques as well as classical methods such as support vector machine and decision tree methods. Availability of both deep white matter and well as cortical recordings may facilitate control for brain state non-homogeneity during sleep states.

Significance and/or Uniqueness of the Proposed Effort

A primary significance of the work proposed resides in the development and utilization of novel treatment and unique brain data collection methods and, analytic strategies in subjects and novel treatments in a population with serious, treatment resistant PTSD. There are four major areas of significance in this realm:

1) EEG may be continuously recorded from locations within the brain (iEEG) while PTSD subjects reside at home going about routine life experiences. This may permit collection of brain as well as behavioral data including spontaneous symptom eruption obviating the artificial laboratory environment used in previous studies. Such recordings in a normal environment to identify the physiological signature of brain state changes accompanying a major mental disorder have never been previously possible outside of an artificial laboratory environment. The baseline recording period may permit establishment of normative values for sleeping, waking and changes associated with symptom onset.

2) PTSD symptomatic episodes, self-identified by subjects when they occur using, for example, a cell phone app, may be recognized immediately. EEG changes accompanying these PTSD symptomatic episodes as well as data preceding, accompanying, and following treatment may thus be isolated. Leveraging this critical data, a PTSD DNN may be developed using the latest deep learning techniques and AI strategies, with goals including identifying those specific brain state changes accompanying PTSD symptomatic episodes, as well as early brain state changes preceding and most probably predicting symptomatic episodes. A key goal is using an AI EEG DNN to reliably identify the specific neurophysiological altered PTSD brain states.

3) Following the baseline recording period, systematic treatment with ICV valproate may begin with individualized dose escalation until symptomatic episodes no longer occur or dose limiting side effects occur. This ICV treatment protocol is unique, with a goal of symptom control in a patient population previously non-responsive to treatment. Ongoing long term follow-up EEG recordings may determine possible resolution of previously identified waking and sleep abnormalities with restoration of normative values with effective treatment related symptom control, facilitating controlled dose reduction with ongoing physiological monitoring. This approach has never before been possible due to the inability to collect long term, high quality iEEG data. A second goal is initiating intraventricular drug delivery to minimize abnormal PTSD memory recall from the hippocampus.

4) Once EEG signatures described in (3) above have been obtained, AI analytic strategies may be utilized with surface EEG and other physiological measures (e.g. activity counts, heart rate and variability, skin conductance measures) with a goal of identifying non-invasive physiological measures capable of measuring and predicting PTSD related symptoms. Such measures have never been previously identified or described and represent a major scientific advance that could well be applied to other behavioral disturbances and their accompanying altered brain states, such as mood disorders and substance misuse, which also represent major problems for both military and civilian populations.

Site-Specific Hippocampal/Amygdala Drug Treatment for severe PTSD is novel and builds on work in minimally invasive epilepsy drug treatment. iEEG data is a novel application for PTSD, may expand on foundational non-invasive EEG and epilepsy work, and may facilitate unique novel clinical and product development strategy to further the targeted search for useful PTSD electrophysiologic biomarkers.

The combined PTSD approach offers the potential for patients with severe, non-remitting symptoms to receive treatment and resume normal life activities. An effective treatment and diagnostic may also benefit the family members who bear witness to the profound ongoing suffering and reduced quality of life of PTSD patients. A non-invasive diagnostic will not only enable triage and rapid diagnosis, but may resolve transparency issues, inform more invasive treatments, reduce PTSD stigma and prevalence, and improve outcomes for the full spectrum of PTSD sufferers.

Additional relevance of a reliable and effective treatment strategy is found in the diminution in adverse consequences and costs associated with untreated or inadequately treated PTSD in a number of biological domains. Depression and substance abuse are common comorbidities with PTSD, aggravated by continuation of PTSD symptoms. Chronic PTSD may be accompanied by increases in inflammatory markers including interleukin 6, interleukin 1$\beta$, TNF$\alpha$, and interferon $\gamma$ levels, supporting low grade inflammation with adverse pathophysiological implications including decreased neurogenesis leading to brain volume loss, impairment in memory formation and consolidation, and acceleration of aging via reactive oxygen species mediated exacerbation of telomere dysfunction and cell senescence, which could explain the association between PTSD and aging. PTSD is also accompanied by increases in REM sleep without atonia, a harbinger of REM behavior disorder with its associated increases in risk for future neurodegenerative disease.

Another PTSD related issue relates to risk factors for development of symptomatic PTSD in response to stress. In fact, only a minority of severely stressed individuals develop PTSD, approximately 20-30% being worse case. The other 70-80% of individuals do not develop PTSD after experiencing similar stress. Identification of those at risk beforehand would be very helpful in terms of decreasing incidence of PTSD and associated social, medical, and military costs. Two major risk factors for development of PTSD in response to stress are socioeconomic status (SES), and early childhood experience. The risk for developing PTSD in recent military veterans is higher than that of the civilian population following major traumatic stress, and SES is a major factor separating military from civilian populations.

The enhanced treatment approach has the potential to enhance recovery rates and quality of life patients suffering from PTSD.

The development of such new strategies for identification and modulation of brain states accompanying other significant behavioral disorders such as mood disorders, anxiety disorders, problems associated with substance misuse and related issues may have wide ranging impact in terms of early identification and treatment before disorders become chronic and disabling.

This PTSD study may evaluate if the test drug and devices are safe and effective for the study population and if the iEEG recordings may be useful with AI in identifying and detecting key biomarkers for the core symptoms of PTSD. The primary goal of this preliminary study is to evaluate if the intervention shows promise of efficacy for patients with PTSD. A positive outcome would provide evidence of lessened distress related to traumatic memory recall. Patients may experience a reduction in the frequency of intrusive and aversive memory recall, in the distress produced by aversive memory recall, or reduced persistence of such episodes of aversive memory recall.

Another goal of this preliminary study is to examine the impact of the intervention on sleep phenomenology related to PTSD. A positive outcome may provide evidence that the intervention is associated with reduced frequency of disrupted sleep, reduced frequency and/or severity of nightmares, and reduced impact of nightmares on daily function.

In addition, this preliminary study may examine whether the severity of other chronic comorbid conditions is altered after starting the intervention, including symptoms of anxiety and depression.

This study also aims to use an AI PTSD DNN to identify EEG biomarkers of core PTSD symptoms (spontaneous traumatic memory recall, frequency of recall, level of distress, sleep symptoms). In particular, the goal is to determine whether these EEG biomarkers provide a sensitive and specific objective index of the therapeutic impact of the intervention. A related goal is to examine the timing of changes in potential EEG biomarkers in relation to changes in physical activity and heart rate. Specifically, the goal will be to test the predictive value of changes in these measures for the onset of new episodes of aversive memory recall. This information may prove valuable in designing early interventions that may prevent subsequent flashback/panic episodes and reduce the burden of PTSD overall.

After providing informed consent, patients may be screened for inclusion/exclusion criteria and all patients may continue their prescribed, orally-administered PTSD and other concomitant medications throughout the trial. Clinical assessments, adverse events, PTSD diary, concomitant medications, blood samples and cerebral spinal fluid will be collected and reviewed at designated time points. MRI Scan and ECG may also be performed at baseline and study completion. Subjects may have the surgery and any dose changes and pharmacokinetic sampling performed in an inpatient setting.

After completion of the surgery implant, subjects may participate in a 4-6 month baseline during which the focus will be on collecting behavioral, EEG and other physiological data which may characterize their mood states (electrophysiologic data and autocurate rating of their mood state) and identify episodes of spontaneous PTSD memory recalls including depersonalization, overwhelming dread associated with those recalls, and nightmares.

Over the next month, the ICV Valproate dose may be introduced and escalated over four weeks, if tolerated, or stopped earlier upon establishment of a subject's maximum tolerated dose (MTD). After establishing a patient's MTD, delivery of ICV Valproate may continue at the MTD for three months during the dosing Evaluation Period and compared with baseline.

During each week of the dose escalation, during the Primary Evaluation Period and Long-Term Follow-up, patients may have 24 hours a day EEG recording which includes sleep stage, circadian and ultradian rhythm calculations along with activity monitoring, heart rate and variability. Psychometric assessments will be performed on a scheduled basis.

A high-quality EEG database on PTSD patients analyzable using cutting edge Artificial Intelligence (AI), may be important to making diagnostic advancement in this field. The long-term EEG data for such database and AI models may only be accessible through invasive approaches, which is feasible and potentially beneficial to severe patients when the collection of this data is coupled with a low-risk therapeutic drug infusion.

This PTSD approach builds on Cerebral Therapeutics, Inc.'s active drug (reformulated ICV valproate, CT 010) and catheter development (ICVRx) programs for severe epilepsy, a long-term brain iEEG epilepsy data set, and the documented success of more aggressive therapies in subsets of severe psychiatric patients. High-quality brain iEEG data collected while providing site-specific medication treatment of severe PTSD patients may be foundational toward building a non-invasive AI based predictive diagnostic. The non-invasive PTSD diagnostic may function on lower-quality non-invasive data from severe PTSD patients, later expanding to non-invasive data sets for diagnosis of mild and moderate PTSD patients.

Prophetic Protocol

The following prophetic example provides a summary of a trial protocol that may be employed to evaluate the principles described herein.

Test drug: Cerebral Therapeutics—Sodium Valproate for ICV use 90 mg/ml (CT 010)

Test Infusion pump: Tricumed—IP 2000V Implantable Pump

Catheter/access port: Cerebral Therapeutics—ICVRx Smart Implantable ICV Catheter Study Indication: Treatment-resistant PTSD Synopsis: Evaluate if the Test Drug (CT 010) and Devices (IP 2000V and ICVRX Smart) are safe and effective for the Study Population and if the ICVRx Smart Catheter will be useful in identifying and detecting key biomarkers for the core symptoms of PTSD. The study will first have an enrollment period when screening is completed, followed by device implantation, followed by a PTSD symptom monitoring period, followed by Investigational Product dose escalation, followed by the primary evaluation period which is followed by the Long-Term Follow up.

Patient population inclusion criteria: Female or Male patients between age 18-70 that are diagnosed with PTSD as defined by the Diagnostic and Statistical Manual fifth edition (DSM-5). Treatment resistance may be defined by the persistence of at least moderate clinical symptoms despite adequate treatment (dose, duration and compliance) with three modalities, including a) selective serotonin reuptake inhibitors, b) cognitive behavioral therapy, c) other classes of medications and/or psychotherapy. Patients should exhibit moderate-to-severe forms of the disease as measured by Clinician Administered PTSD Scale (CAPS) scores ≥50. The PTSD should be chronic, non-remitting PTSD with duration >2 years. Patients should have the capacity to provide informed consent and comply with all evaluations and protocols and ability to attend study appointments. Patients should meet inclusion criteria for at least one of symptoms listed below. All symptoms need not be present for enrollment: (i) Unwanted memories occurring >20 times per month at enrollment baseline; (ii) Dissociative Reactions Flashbacks occurring >3 times per month at enrollment baseline.

Patient population exclusion criteria: (i) patients with past or current psychosis or mania; (ii) history of schizophrenia, schizoaffective disorder, psychotic depression or bipolar 1 disorder; (iii) history of at most mild Traumatic Brain Injury (Physician evaluation, VA Traumatic Brain Injury Screening Tool (VATBIST)198), (iv) active neurologic disease including epilepsy, Parkinson's disease, multiple sclerosis, Alzheimer's disease, other dementias, etc.; (v) alcohol or substance dependence or abuse in the last 6 months, excluding caffeine and nicotine; (vi) active suicidal intent or suicide attempt within the last 2 years; (vii) contraindication to CT or MRI; (viii) likely to relocate or move out of the country during the study's 3 year duration; (ix) presence of a neurological or other medical condition that significantly increases the risk of the surgical procedure; (x) currently pregnant (as determined by history and serum HCG) or lactating; for females of reproductive potential: use of highly effective contraception for at least 1 month prior to screening and agreement to use such a method during study participation; (xi) obstruct sleep apnea-(Initial study exclude with AAHI>10 or 15).

Study goal: (i) A primary goal of is to evaluate if the intervention shows promise of efficacy for patients with PTSD. A positive outcome would provide evidence of lessened distress related to traumatic memory recall. Patients may experience a reduction in the frequency of intrusive and aversive memory recall, in the distress produced by aversive memory recall, or reduced persistence of such episodes of aversive memory recall. (ii) Another goal is to examine impact of the intervention on sleep phenomenology related to PTSD. A positive outcome would provide evidence that the intervention is associated with reduced frequency of disrupted sleep, reduced frequency and/or severity of nightmares, and reduced impact of nightmares on daily function. In addition, this preliminary study will examine whether the severity of other chronic co-morbid conditions is altered after starting the intervention, including symptoms of anxiety and depression. (iii) In addition, the study may identify EEG biomarkers of core PTSD symptoms (spontaneous traumatic memory recall, frequency of recall, level of distress, sleep symptoms, etc.). In particular, the goal is to determine whether the EEG biomarker provides a sensitive and specific objective index of the therapeutic impact of the intervention. (iv) A related goal is to examine the timing of changes in potential EEG biomarkers in conjunction in relation to changes in physical activity and heart rate. Specifically, the goal will be to test the predictive value of changes in these measures for the onset of new episodes of aversive memory recall. This information may prove valuable in designing early interventions that may prevent subsequent flashback/panic episodes and reduce the burden of PTSD overall.

Study design: (i) After providing informed consent, patients may be screened for inclusion/exclusion criteria and all patients may continue their prescribed, orally administered PTSD and other concomitant medications throughout the trial. Clinical assessments, AEs, PTSD diary, concomitant medications, blood samples and CSF may be collected and reviewed at designated time points. MRI Scan, and ECG will also be performed at baseline and study completion. (ii) subjects may have the surgery, any dose change and pharmacokinetic sampling performed in an inpatient setting. (iii) After completion of the surgery implant, subjects may participate in a four-to-six-month baseline during which the focus will be on collecting behavioral and EEG and other physiological data which may characterize their mood states (electrophysiologic data and autocurate rating of their mood state) and identify episodes of spontaneous PTSD memory recalls including depersonalization, overwhelming dread associated with those recalls, and nightmares. (iv) Over the next month, the ICV Valproate dose may be introduced and escalated over four weeks (50, 100, 150 and 200 mgs/day of ICV Valproate), if tolerated, or stopped earlier upon establishment of a subject's maximum tolerated dose (MTD). The MTD for each patient may be determined based on the highest dose tolerated without experiencing a dose-limiting AE. After establishing a patient's MTD, delivery of ICV Valproate may continue at the MTD for three months during the dosing Evaluation Period and compared with baseline. (v) Continuously, during each week of the dose escalation, during the PEP (Primary Evaluation Period) and LTFU (Long Term Follow-up), patients may have 24 hours a day EEG recording which includes sleep stage, circadian and ultradian rhythm calculations along with activity monitoring, heart rate and variability. Psychometric assessments may be performed on a scheduled basis and may include CAPS, BDI, BAI Columbia-Suicide Severity Rating Scale (C-SSR) (McCall) (scale for active suicide ideation), and PSQI (Pittsburgh Sleep Quality Index). (vi) As patients may have failed multiple meds and therapy, patients may have medication changes limited and documented during the study at the treating physician and medical monitor discretion to limit patient's severe symptom exacerbation.

Objectives (endpoints): (i) Evaluation of therapy related Serious Adverse Events and Unanticipated Adverse Device Effects related to procedure, drug and/or device. (To be determined: SAFTEE, UKU, MADRS). (ii) Reduction in CAPS PTSD Score that is meaningful (by 30-50% PTSD) CAPS B1 (Memories), B2 (Daytime Flashbacks) and B3 (Nightmares) sub score particularly to improvement. Need to decide one and three months. (iii) Global Secondary Endpoints and Comorbidity: (a) Difference in cognition, (b) Patient Global Impression of Change (PGIC) (1-7, high better), (c) Clinical Global Impact of Change (CGIC) (1-7, low better), (d) Patient Health Questionnaire 9-item Depression scale (PHQ-9), (0-27), (e) Quality of Life Inventory (QOLI), (−6 to 6), (f) PCL-5 20 item self-report (20 DSM-5 symptoms of PTSD), (g) Beck Depression and Anxiety Inventories (BDII-II; BAI) 20 item self; (iv) Sleep Secondary Endpoints: (a) Improvement in objective sleep markers including: (1) N3 Slow wave Delta sleep (quantitate), Total REM sleep (quantitate), (2) Change in sleep spindle frequency (Wang2020), Sleep total Sleep Time (TST), Increased Sleep Efficiency (SE), Sleep Latency (SL), Increased Total Sleep Times, and Sleep spectral changes (including increased delta power suggesting increased homeostatic sleep drive, decreased beta/gamma power suggesting decreased hyperarousal state) (Wang2020 #2), (3) Pittsburgh Sleep Quality Index (PSQI), 0-21), and (4) Decreased REM interruptions (Habakawau); (v) EEG Bio-Markers Comparison at differing dose levels & versus baseline including: (a) Non AI Gamma Band, (b) P300; (v) AI Features Example 3—Traumatic Brain Injury Traumatic brain injury (TBI) remains a leading cause of disability and death in children and adults in their most productive years. It is also a leading cause of morbidity and mortality in the military. Every year an estimated 1.6 million head injuries occur in the US. TBI affects three out of every 1,000 Americans annually, accounting for as many as 60,000 deaths and an estimated 70,000 to 90,000 individuals with chronic neurological disabilities. The economic consequences of these injuries are enormous in terms of lost productivity and medical care costs. The direct and indirect costs of TBI in the US are estimated to be $48.3 billion annually. Survivor costs account for $31.7 billion and fatal brain injuries amount to another $16.6 billion. While the last two decades of research has resulted in a greater understanding of the physiological and cellular events leading to secondary neuronal injury, and methods to characterize changes in cerebral blood flow and intracranial pressure have modestly improved, there remains a profound lack of brain functional measurement tools starting at the time of acute injury through rehabilitation which provide objective metrics to guide treatment decisions in patients with severe TBI.

Management of severe TBI and associated elevated intracranial pressure (ICP) typically necessitates placement of an externalized ventricular drain (EVD). This implant accesses the ventricle via a flexible tube and drains cerebral spinal fluid (CSF) to lower ICP. This procedure, common in neurosurgical practice, is a cornerstone of evidence-based care for patients presenting with severe traumatic closed head injury. Each year, approximately 23,000 EVDs are placed in the US and 4,000 (or 17%) are placed for presumed severe closed head injury.

Patients with EVDs typically go through a two-week period of intensive care during which the patient is often intubated and aggressive multisystem care is focused on preserving life and brain function. These patients typically remain in the hospital for another two or so while caregivers attempt to find placement in a long-term or rehabilitation facility. Challenging behavioral presentations are nearly universal, as is use of psychotropic medications to manage them. A common course is for patients to move from an inpatient setting into at least a year of nursing care or rehabilitation, depending on the level of consciousness, cognition, language, and behavioral disturbance. Despite the obvious criticality of the evolving brain injury, physicians lack objective data regarding brain physiology and function, relying instead on clinical observation and, when possible, self-report to inform treatment decisions. Beginning with the acute onset of injury through the first year of recovery, the clinical challenges evolve, starting with the elevated intracranial pressure, extending to sleep disturbance in the ICU, additional behavioral and sleep challenges in the post-extubation hospitalization period, and later focus on the cognitive, impulse control, and behavioral challenges that interfere with occupational, speech, and physical therapy that, nonetheless, are key to optimizing brain outcomes over the first year To date, while EVDs are surgically implanted in thousands of patients with TBI, they have been employed and designed to date solely to lessen ICP. Current EVD devices provide no information about brain physiology and function despite the great need for objective biomarkers of evolving brain states and despite the fact that EVD devices are already being located physically implanted in patients' brains.

Monitoring of electrical brain signals may include obtaining high quality intracranial brain electroencephalography (iEEG) data from TBI patients. The data may be used to better understand TBI. The data may be used to monitor a state of the disease (such as severity), a state of the patient, or the like. The data may be used to direct, enhance, or direct and enhance TBI therapy. The TBI therapy may include one or more of cognitive therapy, psychological therapy, pharmacological therapy, and ventricular drainage.

CSF may be drained through the use of a drainage catheter having an opening placed in a cerebral ventricle to an opening located outside of the CSF space, such as external to the patient. CSF drainage may reduce ICP.

The CSF drainage catheter may contains one or more electrodes for recording signals from the patient's brain. One or more electrodes of the drainage catheter may be configured to be positioned within or close to white matter of the brain, grey matter of the brain, or white matter and grey matter of the brain. In addition or alternatively, a medical lead separate from a drainage catheter may include one or more electrodes configured to be positioned within or close to white matter of the brain, grey matter of the brain, or white matter and grey matter of the brain. Preferably, the medical lead is configured to be coupled to, or is coupled to, a drainage catheter so that implantation of the drainage catheter results in implantation of the lead, if the drainage catheter is implanted in the brain. That is, it is preferable that only one surgical procedure is performed to place the lead and the drainage catheter. The electrodes may record electrical signals from within the brain.

By placing the electrodes within or in proximity to brain tissue, such as white matter or grey matter, less "noisy" signals may be obtained than with scalp-based EEG recordings. Such higher quality signals may facilitate interpretation of data recorded by the electrodes.

Data recorded by the electrodes may be used to monitor disease or therapy progression, as well as monitor a current brain state or predict a future brain state. Electrical biomarkers may be identified. Such objective biomarkers of disturbed brain function in TBI can provide both targets for therapeutic interventions and valid metrics by which to evaluate the impact of modifications and tailoring of current available treatment strategies. This is especially important because the neuropsychiatric disturbances in TBI frequently compromise the reliability and validity of self-report. Treatment strategies guided by objective biomarkers may result in superior outcomes and shorter treatment periods in intensive care units, hospital, and rehabilitation settings.

Additional information regarding treatment and monitoring of TBI and development of a TBI DNN is described in U.S. Provisional Patent Application No. 63/223,629, filed on Jul. 20, 2021, which application is hereby incorporated herein in its entirety to the extent that it does not conflict with the disclosure presented herein.

Examples of studies that may be done are now provided.
Overview of Potential Pilot Study Collection of high quality, continuous iEEG data may occur during clinician management of TBI. A first step may be focus on epileptiform and sleep stage detection (high risk and frequent complications for these patients). A second may be to expand the data scope applying labeling strategies with the continuous iEEG during the course of their recovery to identify patterns of brain electrical activity that reflect abnormal brain states and/or covary with behavioral disturbance.

In initial phases after injury, detection of undiagnosed epileptiform conditions and sleep disorders may be prioritized using conventional techniques combined with AI methods. As is demonstrated in an epilepsy iEEG pilot data section, advanced AI-DNN methods may subsequently be applied to drive the identification of potential biomarkers, emphasizing and building on application of those deep learning strategies shown most helpful for EEG classification of sleep stages and epileptiform activity. This approach may be expanded from sleep and epileptiform activity to iEEG-DNNs linked to specific disturbances in emotion, motor activity, or cognition. The characterization of sleep disturbances, which may evolve with closed head injury, may include longitudinal analysis of local field potentials from deep brain electrodes using modern machine learning techniques, as well as classical methods, such as support vector machine and decision tree methods. The availability of recordings from both cortical and deep white matter regions may facilitate control for brain state non-homogeneity during sleep states.

During the subsequent phases of recovery, in addition to providing iEEG objective biomarkers of sleep and epileptiform disturbance, it is postulated that the iEEG-DNN approach may provide objective biomarkers useful in the diagnosis and ultimately the management of behavioral disturbances, such as agitation, inattention, or disorientation. Behavioral disturbance in the TBI patient are often incompletely or poorly controlled with psychotropics. Since the iEEG can be continuously collected and because the iEEG implant can remain in the patient even after the EVD has been removed, the TBI DNN strategy can then be expanded over the longer course of recovery to explore the potential of biomarker identification for a variety of neuropsychiatric complications, including sleep disturbances, agitation, PTSD, suicidal and impulsive behaviors.

Detecting EEG sleep and epileptiform activity patterns using an extremely more capable iEEG collecting implant may enable more accurate and clinically meaningful assessment of change in these domains. Given our knowledge of sleep architecture and the nature of epileptiform activity, disturbances in these domains are likely analyzable based on iEEG analysis alone. However, the development of TBI iEEG DNNs may be important for many brain dysfunctions, such as agitation, suicidality, or attentional dysfunction which may require linkage between the brain data and behavioral manifestations. Tagging strategies may be used for such linkage by an experienced AI data analytic and specific PTSD psychiatry team.

Cerebral Therapeutics, Inc. has previously analyzed a pilot data set from a unique epilepsy cohort with just this type of data analytic approach and was able to recognize sleep stages and epileptiform discharges comparable with the proposed modified iEEG ventriculostomy.

In Aim 1, a minimally invasive ventriculostomy catheter and iEEG monitoring device may be used in a pilot study of 20 severe TBI participants to demonstrate potential clinical utility (effective CSF drainage and quality sleep and EEG data captured as compared with scalp EEG data capture). In Aim 1, specific iEEG data signatures for epileptiform activity and sleep disturbance will be generated. The iEEG device acquisition system may record from 2x electrodes distributed over a intracranial depth of approximately 4x cm, with the signals externally digitized (250 Hz sampling rate). This arrangement may produce approximately 0.095 Gigabyte of data per day per patient (about 3 GB per month per patient). The internalized system may be compatible with routine use of ventriculostomy and externalized iEEG capture and digitalization technology may be wearable, and ergonomically and unobtrusively designed, to support cloud-based data transfer.

In Aim 2, the pilot study findings may be expanded to include preliminary application of TBI DNN strategy to the domains of agitation, cognitive impairment, and, when appropriate, PTSD or suicidal ideation. Just as innovation and advanced analytic techniques may be applied to the iEEG data, state-of-the-art methods may be applied when "labelling" contemporaneous behavioral events. The behavior collection strategies may include analysis of video recordings, nursing and caregiver daily reports, medications and their administration times, continuous recording of ongoing physiology (e.g., heart rate, respiration, etc.) and, when feasible, self-report of subjective states and objective task performance.

After successfully addressing Aims 1-2, the follow-on stages of development of the may proceed, progressing towards commercialization and full regulatory (e.g., FDA) clearance. Specifically, this may mean conducting an appropriately powered and controlled clinical trial demonstrating the clinical utility and safety of the technology and iEEG analyses. The design and implementation of a current Phase 2b epilepsy trial conducted by Cerebral Therapeutics, Inc. may be helpful to model an approach for the proposed TBI patient investigation.

A primary significance of the proposed research resides in the collection and utilization of unique brain data and novel analytic strategies to develop biomarkers in a population with severe TBI. There are four major areas of significance in this realm:

1) The collection of high-quality brain data, built upon solid experience with acquisition and analysis of intraventricular sleep and epilepsy continuous iEEG, has never been routinely obtained in patients with severe brain injury, either acutely or over the long-term over the course of their brain injury and recovery. Acquiring these key data provides an unparalleled opportunity for the field: unique high-quality, in the brain, objective data by which to investigate the optimal delivery of rehabilitation interventions and prescriptions (i.e., frequency, intensity, timing, and type), as well as to investigate the comparative effectiveness of standard of care and novel intervention strategies. The functional brain data gap is not unique among brain diseases to severe TBI. However, what is unparalleled is the opportunity to access and analyze these unique brain data with minimal or no added risk and tremendous possibility of gain for patients and the field. Thousands of such patients have EVDs implanted to reduce ICP. Yet, these EVDs currently provide no information about brain physiology or function.

2) During the acute and first weeks of treatment, the continuous iEEG data may be used to monitor for epileptiform activity and sleep disruption. Sleep disturbance and epileptiform activity following TBI are well known to disrupt recovery, impacting on symptom manifestation and behavioral changes, and the management of sleep disturbance and epileptiform activity can be improved upon in many severe TBI patients. Once EEG signatures described in (1) above have been obtained, AI DNN analytic strategies may be utilized and compared with surface EEG and other physiological measures (e.g., activity counts, heart rate and variability, skin conductance measures and others) to initially test sensitivity and specificity in detecting and predicting sleep disturbances and indicators of seizure activity. Based on the much higher quality data, it is expected that the biomarkers identified with ciEEG and AI DNN detection may demonstrate stronger sensitivity and specificity than scalp EEG.

3) After the first 4-6 weeks phase, the iEEG data may continue to be collected, along with additional monitoring for attentional challenges and anxiety symptoms which may trigger oral medication intervention to help patients improve their post-injury course. Similar iEEG and DNN AI techniques and strategies may be applied as in Aim 1, but at this point with tagging to specific behavioral states (e.g., agitation) or subjective states (PTSD, suicidality).

4) Objective biomarkers in TBI of abnormal brain states and behavioral disturbances have never been previously identified and could radically alter clinical management by providing objective and outcome relevant endpoints. This data-driven, empirical strategy represents a major scientific advance that could be applied to other forms of behavioral disturbance and their accompanying altered brain states, such as mood disorders and substance misuse, which also represent major problems for both military and civilian populations.

What is claimed is:
1. A device or system for delivering fluid to or removing fluid from a cerebrospinal fluid (CSF)-containing space of a brain and for recording electrical brain state activity from white or grey matter in the brain, the device or system comprising:

a CSF catheter comprising a proximal end, a distal end portion, and a first lumen extending from the proximal end to the distal end portion; and a brain lead extending from and coupled to the CSF catheter by a snap fit connector comprising at least one deflectable element configured to resiliently deflect as at least one of the brain lead or the CSF catheter is inserted, the brain lead comprising an electrode positioned a distance from the distal end of the CSF catheter such that the electrode is configured to contact white or grey matter of the brain when the distal end of the CSF catheter is placed in the CSF-containing space;

signal processing electronics configured to operably couple to the brain lead and to record electrical activity detected by the electrode and to determine a brain state or to predict a future brain state; and an external apparatus configured to wirelessly receive signals associated with the recorded electrical activity from the signal processing electronics.

2. The device or system of claim 1, wherein the CSF-containing space is a lateral ventricle.

3. The device or system of claim 2, wherein the electrode is positioned a distance from about 0.5 centimeters to about 6 centimeters to the distal end of the CSF catheter.

4. The device or system of claim 2, wherein the electrode is positioned a distance from about 1 centimeter to about 5 centimeters to the distal end of the CSF catheter.

5. The device or system of claim 2, wherein the electrode is positioned a distance from about 2 centimeters to about 6 centimeters to the distal end of the CSF catheter.

6. The device or system of claim 1, wherein the brain lead is coupled relative to the CSF catheter at the distal end portion of the CSF catheter.

7. The device or system of claim 1, wherein the brain lead is secured to the CSF catheter along a substantial length of the CSF catheter.

8. The device or system of claim 1, comprising a brain signal electrical interconnect, wherein the brain signal electrical interconnect comprises a contact electrically coupled to the electrode through the brain lead.

9. The device or system of claim 8, wherein the CSF catheter comprises the brain signal electrical interconnect.

10. The device or system of claim 8, wherein the brain lead comprises the brain signal electrical interconnect.

11. The device or system of claim 8, wherein the brain signal electrical interconnect is physically separate from the brain lead.

12. The device or system of claim 11, further comprising a cable extending from the brain lead to the brain signal electrical interconnect, wherein the cable comprises a conductor electrically connecting the electrode to the contact.

13. The device or system of claim 1, further comprising an access port having a first fluid flow path in communication with the first lumen of the CSF catheter or having a connector configured to secure the CSF catheter such that first lumen is in communication with the first fluid flow path.

14. The device or system of claim 13, wherein the access port is configured to be implanted below a scalp.

15. The device or system of claim 14, wherein at least a portion of the access port is configured to be implanted over a burr hole.

16. The device or system of claim 14, wherein at least a portion of the access port is configured to be implanted in a burr hole.

17. The device or system of claim 1, further comprising an implantable infusion device, wherein the implantable infusion device comprises at least a portion of the signal processing electronics.

18. The device or system of claim 1, wherein the cranial catheter is an external ventricular drainage catheter or a ventriculoperitoneal shunt.

19. The device or system of claim 1, wherein the signal processing electronics are further configured to apply brain stimulative electrical signals to a stimulating electrode coupled to the CSF catheter.

20. The device or system of claim 1, wherein the signal processing electronics are further configured to wirelessly transmit the signals to the external apparatus through a portion of a scalp.

21. The device or system of claim 1, wherein the external apparatus is further configured to wirelessly power the signal processing electronics using inductive coupling.

22. The device or system of claim 1, wherein the brain lead is coupled to the CSF catheter by a snap fit connector comprising a first opening and a second opening.

23. The device or system of claim 22, wherein the second opening is symmetrical to the first opening.

24. The device or system of claim 22, wherein the first opening is configured to engage the brain lead and the second opening is configured to engage the CSF catheter.

25. The device or system of claim 1, wherein the brain lead is coupled to the CSF catheter by a sleeve.

26. The device or system of claim 1, wherein the snap fit connector comprises a first set of deflectable elements and a second set of deflectable elements.

27. The device or system of claim 26, wherein the first set of deflectable elements is configured to engage the brain lead and the second set of deflectable elements is configured to engage the CSF catheter.

28. A device or system comprising:

an implantable access port, the access port comprising:

an opening accessible by a needle when the access port is implanted;

a first catheter connector;

a second catheter connector;

a first fluid flow path extending from the opening to the first catheter connector; and a second fluid flow path extending from the second catheter connector to the first catheter connector;

a CSF catheter coupled to, or operably couplable to, the first catheter connector, the CSF catheter comprising a proximal end, a distal end portion, and first and second lumens extending from the proximal end to the distal portion of the CSF catheter;

a brain lead extending from and coupled to the CSF catheter by a snap fit connector comprising at least one deflectable element configured to resiliently deflect as at least one of the brain lead or the CSF catheter is inserted, the brain lead comprising an electrode configured to detect electrical activity determinative of a brain state or predictive of a future brain state, wherein the first lumen is in communication with the first fluid flow path and the second lumen is in communication with the second fluid flow path when the proximal end of the CSF catheter is coupled to the first catheter connector, wherein the CSF catheter has a length such that a distal end is configured to extend to a CSF-containing space of a subject when the access port is implanted, wherein the electrode is positioned a distance from the distal end of the CSF catheter and configured to be positioned in white or grey matter of a brain of the subject when the access port is implanted and the distal end of the CSF catheter is positioned in the CSF-containing space;

signal processing electronics configured to operably couple to the brain lead and to record electrical activity detected by the electrode and to determine a brain state or to predict a future brain state; and an external apparatus configured to wirelessly receive signals associated with the recorded electrical activity from the signal processing electronics.

29. The device or system of claim 28, wherein the signal processing electronics are further configured to apply brain stimulative electrical signals to a stimulating electrode coupled to the CSF catheter.

30. The device or system of claim 29, wherein the stimulating electrode is the brain lead electrode.

31. The device or system of claim 28, wherein the second fluid flow path comprises a microbial filter.

32. The device or system of claim 28, wherein the signal processing electronics are further configured to wirelessly transmit the signals to the external apparatus through a portion of a scalp of the subject.

33. The device or system of claim 28, wherein the external apparatus is further configured to wirelessly power the signal processing electronics using inductive coupling.

* * * * *